United States Patent [19]

Broxmeyer et al.

[11] Patent Number: 6,165,459
[45] Date of Patent: Dec. 26, 2000

[54] METHODS FOR SUPPRESSING MYELOID CELLS WITH CHEMOKINES

[75] Inventors: Hal E. Broxmeyer; Scott Cooper; Charles Mantel; Li Lu, all of Indianapolis, Ind.

[73] Assignee: Indiana University Foundation, Indianapolis, Ind.

[21] Appl. No.: 08/474,536

[22] Filed: Jun. 7, 1995

Related U.S. Application Data

[63] Continuation of application No. 08/094,685, Jul. 20, 1993, abandoned, which is a continuation-in-part of application No. 07/987,638, Dec. 9, 1992.

[51] Int. Cl.⁷ ............................ A61K 38/19; A61K 38/20
[52] U.S. Cl. ............................ 424/85.2; 424/85.1; 514/2; 514/8; 514/12; 514/885
[58] Field of Search ............................ 514/2, 8, 12, 885; 424/85.1, 85.2

[56] References Cited

U.S. PATENT DOCUMENTS 5,306,709   4/1994   Gewirtz ................................ 514/12

OTHER PUBLICATIONS

Oh et al. (1991) J. of Immunol. vol 147, No. 9, p. 2978–2983.
Broxmeyer et al J. Immunol. 147 pp. 2586–94 Oct. 1991.
Wolfe et al The Faseb J. 3 pp 2565–73 Dec. 1989.
Bennett et al. Biochem Biophys Res Comm. vol. 101 pp 88–95 1981.
Webster's Ninth New Collegiate Dictionary, p 1198 Merrion–Webster Inc., Springfield Mass (1983).
Broxmeyer, et al., "The Production of Myeloid Blood Cells and Their Regulation During Health and Disease", *CRC Crit. Rev. Oncol/Hematol.*, vol. 8, p. 173 (1988).
Broxmeyer, "Biomolecule–cell Interactions and the Regulation of Myelopoiesis, An Update", in Murphy Jr. (ed): *Concise Reviews in Clinical and Experimental Hematology*, Dayton, Ohio, Alpha Med Press, p. 119 (1992).
Broxmeyer, "Suppressor Cytokines and Regulation on Myelopoiesis: Biology and Possible Clinical Uses", *Amer. J. Ped. Hematol/Oncol.*, vol. 14, p. 22 (1992).
Wolpe, et al., "Macrophages Secrete A Novel Heparin–Binding Protein with Inflammatory and Neutrophil Chemokinetic Properties", *J. Exp. Med.*, vol. 167, p. 570 (1980).
Davatelis, et al., "Cloning and Characterization of a cDNA for Murine Macrophage Inflammatory Protein (MIP), a Novel Monokine with Inflammatory and Chemokinetic Properties", *J. Exp. Med.*, vol. 167, p. 1939 (1988).
Graham et al., "Identification and Characterization of an Inhibitor of Hematopoietic Stem Cell Proliferation", *Nature*, vol. 334, p. 442 (1990).
Broxmeyer, et al., "Enhancing and Suppressing Effects of Recombinant Murine Macrophage Inflammatory Proteins on Colony Formation in vitro by Bone Marrow Myeloid Progenitor Cells", *Blood*, vol. 76, p. 1110 (1990).

Bodine, et al., "Effects of Hematopoietic Growth Factors on the Survival of Primitive Stem Cells in Liquid Suspension Culture", *Blood*, vol. 78, p. 914 (1991).
Broxmeyer, et al., "Macrophage Inflammatory Protein (MIP)–1β Abrogates the Capacity of MIP–1α to Suppress Myeloid Progenitor Cell Growth", *J. Immunol.*, vol. 147, p. 2586 (1991).
Maze, et al., "Myelosuppressive Effects in vivo of Purified Recombinant Murine Macrophage Inflammatory Protein–1 Alpha", *J. Immunol.*, vol. 149, p. 1004 (1992).
Dunlop, et al., "Demonstration of Stem Cell Inhibition and Myeloprotective Effects of SCI/rhMIP–1α in vivo", *Blood*, vol. 79, p. 2221 (1992).
Lord, et al., "Macrophage–Inflammatory Protein Protects Multipotent Hamatopoietic Cells from the Cytotoxic Effects of Hydroxyurea in vivo", *Blood*, vol. 79, p. 2605 (1992).
Oh, et al., Identification of Cell Surface Receptors for Murine Macrophage Inflammatory Protein–1α, *J. Immunol.*, vol. 147, p. 2978 (1991).
Fahey, et al., "Macrophage Inflammatory Protein 1 Modulates Macrophage Function", *J. Immunol.*, vol. 148, p. 2764 (1992).
Wolpe, et al., "Macrophage Inflammatory Proteins 1 and 2: Members of a Novel Superfamily of Cytokines", *FASEB J.*, vol. 3, p. 2565 (1989).
Oppenheim, et al., "Properties of the Novel Proinflammatory Supergene 'Intercrine' Cytokine Family", *Ann. Ref. Immunol.*, vol. 9, p. 617 (1991).
Schall, "Biology of the Rantes/Sis Cytokine Family", *Cytokine*, vol. 3, pp 165 (1991).
Lu, et al., "Characterization of Adult Human Marrow Hematopoietic Progenitors Highly Enriched by Two–Color Sorting with My10 and Major Histocompatibility (MHC) Class II Monoclonal Antibodies", *J. Immunol.*, vol. 139, pp. 1823 (1987).
Tekamp–Olson et al., "Cloning and Characterization of cDNAs for Murine Macrophage Inflammatory Protein 2 and Its Human Homologues", *J. Exp. Med.*, vol. 172, pp. 911 (1990).
Broxmeyer, et al., "Effect of Murine Mast Cell Growth Factor (c–kit Proto–oncogene Ligand) on Colony Formation by Human Marrow Hematopoietic Progenitor Cells", *Blood*, vol. 77, pp. 2142 (1991).
Gewirtz et al., "Inhibition Of Human Megakaryocytopoiesis in Vitro by Platelet Factor 4 (PF4) and a Synthetic COOH–Terminal PF4 Peptide", *J. Clin. Invest.*, vol. 83, pp. 1477–1486 (1989).

(List continued on next page.)

*Primary Examiner*—Prema Mertz
*Attorney, Agent, or Firm*—Woodard, Emhardt, Naughton, Moriarty & McNett

[57] ABSTRACT

Described are preferred processes and compositions for suppressing myeloid cells in mammals. Preferred processes and compositions involve the use of chemokines in synergistic combinations or while they are substantially completely in monomeric form (i.e. substantially free from their polymerized or aggregated forms).

22 Claims, 28 Drawing Sheets

OTHER PUBLICATIONS

Sherry, et al., "Resolution of the Two Components of Macrophage Inflammatory Protein 1, and Cloning and Characterization of One of Those Components, Macrophage Inflammatory Protein 1β", *J. Exp. Med.*, vol. 168, p. 2251 (1988).

Jaffe et al., Culture of human endothelial cells derived from umbilical veins. Identification by morphologic and immunologic criteria, *J. Clin. Invest.* 52:2745 (1973).

Tsao et al., Clonal Growth of normal human epidermal keratinocytes in a defined medium, J. Cell. Physiol. 110:219 (1983).

Wright et al., Tumor–promoting phorbol esters stimulate C3b and C3b' receptor–mediated phagocytosis in cultured human monocytes, *J. Exp. Med.* 156:1149 (1982).

Scotchler et al., Cleavage of single amino acid residues from purified resin with hydrogen chloride and hydrogen fluoride, J. Org. Chem. 35:3151 (1970).

Pfaff et al., Antibodies against a preselected peptide recognize and neutralize foot and mouth disease virus, *EMBO* (Eur. Mol. Biol. Organ.) J. 1:869 (1982).

Matsuura et al., Baculovirus expression vectors :the requirements for high level expression of proteins, including glycoproteins, *J Gen Virol*, 68:1233 (1987).

Schragger et al., Tricine–sodium docecyl sulfate polyacrylamide gel electrophoresis for the separation of proteins in the range from 1 to 100 kDa, *Anal Biochem*, 166:368 (1987).

Dreyfuss et al., Physical changes in cytoplasmioc messenger ribonucleoproteins in cells treated with inhibitors of mRNA transcription, *Mol Cell Biol* 4, 415–423 (1984).

Towbin et al., Electrophoretic transfer of proteins from polyacrylamide gels to nitrocellulose sheets: Procedure and some applications, *Proc Natl Acad Sci USA*, 76:4350 (1979).

Webb et al., Expression of proteins using recombinant baculoviruses, *Technique* 2: 173 (1990).

Sanger et al., DNA sequencing with chain–terminating inhibitors, *Proc Natl Acad Sci USA*, 74:5463 (1977).

Sarris et al., Immunofluorescent localization and immunochemical determination of Cyclophilin–A with specific rabbit antisera, *Transplantation*, 54:904 (1992).

Saiki et al., Primer–directed enzymatic amplification of DNA with a thermostable DNA polymerase, *Science*, 239:487 (1988).

Luster et al., Biochemical characterization of a g Interferon–inducible cytokine (IP–10), *J Exp Med*, 166:1084 (1987).

Studier et al., Use of T7 polymerase to direct expression of cloned genes, *Methods in Enzymology*, 185:60 (1990).

Lindley et al., Synthesis and expression in *Escherichia coli* of the gene encoding monocyte–derived neutrophil–activating factor: Biological equivalence between natural and recombinant neutrophil–activating factor, *Proc Natl Acad Sci USA*, 85:9199 (1988).

Bradford, A rapid and sensitive method for the quantitation of microgram quantities of protein utilizing the principle of protein–dye binding, *Anal Biochem*, 72:248. (1976).

Hewick et. al., A gas–liquid solid phase peptide and protein sequenator. J Biol Chem, 256:7990 (1981).

Tempst et al., Examination of automated polypeptide sequencing using standard phenyl isothiocyanate reagent and subpicomole high–performance liquid chromatographic analysis, *Anal Biochem*, 183:290 (1989).

Bennett et al., Calcium–dependent polymerization of lactoferrin, *Biochem. Biophys. Res. Comm.*, 101:88 (1981).

A

B

Percent Progenitors in Cycle

Progenitors per Organ

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 27
        (B) TYPE: Nucleotide
        (C) STRANDEDNESS: Single
        (D) TOPOLOGY: Linear (ii) MOLECULE TYPE: Primer -continued (iii) SEQUENCE DESCRIPTION: SEQ ID NO:1:

GGATCCATGG TACCTCTCTC TAGAACC                27

(2) INFORMATION FOR SEQ ID NO:2:

(i) SEQUENCE CHARACTERISTICS:
        (A) LENGTH: 28
        (B) TYPE: Nucleotide
        (C) STRANDEDNESS: Single
        (D) TOPOLOGY: Linear (ii) MOLECULE TYPE: Primer (iii) SEQUENCE DESCRIPTION: SEQ ID NO:2:

GGATCCATGG TTAAGGAGAT CTTTTAGA               28

(2) INFORMATION FOR SEQ ID NO:3:

(i) SEQUENCE CHARACTERISTICS:
        (A) LENGTH: 31
        (B) TYPE: Nucleotide
        (C) STRANDEDNESS: Single
        (D) TOPOLOGY: Linear (ii) MOLECULE TYPE: Primer (iii) SEQUENCE DESCRIPTION: SEQ ID NO:3:

GGATCCATGG TTATGGATTC AGACATCTCT T           31

METHODS FOR SUPPRESSING MYELOID CELLS WITH CHEMOKINES

REFERENCE TO RELATED APPLICATION

This application is a continuation of application Ser. No. 08/094,685, filed Jul. 20, 1993, now abandoned, which is a continuation-in-part of U.S. patent application Ser. No. 07/987,638 filed Dec. 9, 1992, now pending, which is hereby incorporated herein by reference.

BACKGROUND

The present invention resides generally in the field of regulation of myeloid cells such as stem cells or progenitor cells. More particularly, the present invention relates to the suppression of myeloid cells using chemokines.

As further background, accessory cell-derived cytokines regulate proliferation/differentiation of hematopoietic stem and progenitor cells in vitro and in vivo. See, Broxmeyer, et al., "The Production of Myeloid Blood Cells and Their Regulation During Health and Disease", *CRC Crit. Rev. Oncol/Hematol.*, Vol. 8, p. 173 (1988); and Broxmeyer, "Biomolecule-cell Interactions and the Regulation of Myelopoiesis, An Update", in Murphy Jr. (ed): *Concise Reviews in Clinical and Experimental Hematology*, Dayton, Ohio, Alpha Med Press, p. 119 (1992). Cytokines can have stimulating, enhancing, and/or suppressing activities mediated either directly on stem/progenitor cells and/or indirectly on accessory cells.

A number of cytokines have been implicated in negative regulation. See, Broxmeyer, et al., "The Production of Myeloid Blood Cells and Their Regulation During Health and Disease", supra; Broxmeyer, "Biomolecule-cell Interactions and the Regulation of Myelopoiesis, An Update", supra; and Broxmeyer, "Suppressor Cytokines and Regulation on Myelopoiesis: Biology and Possible Clinical Uses", *Amer. J. Ped. Hematol/Oncol.*, Vol. 14, p. 22 (1992). Suppression can be mediated by biological molecules termed cytokines, such as macrophage inflammatory protein (MIP)-1α, a heparin binding protein originally identified by its capacity to cause a localized inflammatory reaction after injection into the footpads of C3H/HeJ mice. See, Wolpe, et al., "Macrophages Secrete A Novel Heparin-Binding Protein with Inflammatory and Neutrophil Chemokinetic Properties", *J. Exp. Med.*, Vol. 167, p. 570 (1980); Davatelis, et al., "Cloning and Characterization of a cDNA for Murine Macrophage Inflammatory Protein (MIP), a Novel Monokine with Inflammatory and Chemokinetic Properties", *J. Exp. Med.*, Vol. 167, p. 1939 (1988); and Sherry, et al., "Resolution of the Two Components of Macrophage Inflammatory Protein 1, and Cloning and Characterization of One of Those Components, Macrophage Inflammatory Protein 1β", *J. Ext. Med.*, Vol. 168, p. 2251 (1988).

MIP-1α, but not a closely related family member MIP-1β suppressed proliferation of a subset of murine (mu) stem cells (day 12 colony forming-unit-spleen (CFU-S)) ex vivo and mu colony forming unit-A (an apparently early progenitor cell) (see, Graham et al., "Identification and Characterization of an Inhibitor of Hematopoietic Stem Cell Proliferation", *Nature*, Vol. 334, p. 442 (1990)), as well as mu and human (hu) growth-factor stimulated multipotential (CFU-GEMM), erythroid (BFU-E) and granulocyte macrophage (CFU-GM) progenitor cells (see, Broxmeyer, et al., "Enhancing and Suppressing Effects of Recombinant Murine Macrophage Inflammatory Proteins on Colony Formation in vitro by Bone Marrow Myeloid Progenitor Cells", *Blood*, Vol. 76, p. 1110 (1990)) in vitro. Suppressive effects of MIP-1α were apparent on more immature populations of progenitors which were stimulated to proliferate by a combination of two or more early acting growth stimulating cytokines. See, Broxmeyer, et al., "Enhancing and Suppressing Effects of Recombinant Murine Macrophage Inflammatory Proteins on Colony Formation in vitro by Bone Marrow Myeloid Progenitor Cells", *Blood*, Vol. 76, p. 1110 (1990); and Bodine, et al., "Effects of Hematopoietic Growth Factors on the Survival of Primitive Stem Cells in Liquid Suspension Culture", *Blood*, Vol. 78, p. 914 (1991). These effects appeared to be directly on the progenitors themselves. See, Broxmeyer, et al., "Macrophage Inflammatory Protein (MIP)-1β Abrogates the Capacity of MIP-1α to Suppress Myeloid Progenitor Cell Growth", *J. Immunol.*, Vol. 147, p. 2586 (1991). MIP-1α did not suppress proliferation of the more mature progenitors which were stimulated to proliferate by a single cytokine. See, Broxmeyer, et al., "Enhancing and Suppressing Effects of Recombinant Murine Macrophage Inflammatory Proteins on Colony Formation in vitro by Bone Marrow Myeloid Progenitor Cells", supra; and Broxmeyer, et al., "Macrophage Inflammatory Protein (MIP)-1β Abrogates the Capacity of MIP-1α to Suppress Myeloid Progenitor Cell Growth", supra.

MIP-1α has recently been shown to have in vivo suppressive effects on cycling rates of CFU-S, CFU-GEMM, BFU-E and CFU-GM when administered to mice (see, Maze, et al., "Myelosuppressive Effects in vivo of Purified Recombinant Murine Macrophage Inflammatory Protein-1 Alpha", *J. Immunol.*, Vol. 149, p. 1004 (1992); Dunlop, et al., "Demonstration of Stem Cell Inhibition and Myeloprotective Effects of SCI/rhMIP-1α in vivo", *Blood*, Vol. 79, p. 2221 (1992); and Lord, et al., "Macrophage-Inflammatory Protein Protects Multipotent Hamatopoietic Cells from the Cytotoxic Effects of Hydroxyurea in vivo", *Blood*, Vol. 79, p. 2605 (1992)), and in this context was myeloprotective for the drugs cytosine arabinoside (see, Dunlop, et al., supra) and hydroxyurea (see, Lord, et al., supra.) MIP-1β was not myelosuppressive in vivo. See, Maze, et al., supra.

MIP-1α also inhibited proliferation of an unstimulated cytotoxic T-cell line, CTLL-R8 (see, Oh, et al., Identification of Cell Surface Receptors for Murine Macrophage Inflammatory Protein-1α", *J. Immunol.*, Vol. 147, p. 2978 (1991)), and modulated macrophage function, including induction of the release of tumor necrosis-factor, interleukin (IL)-1α and IL-6 in vitro. See, Fahey, et al., "Macrophage Inflammatory Protein 1 Modulates Macrophage Function", *J. Immunol.*, Vol. 148, p. 2764 (1992). MIP-1β, when present in excess compared to MIP-1α in vitro, blocked both the suppressive effects of MIP-1α on myeloid progenitors (see, Broxmeyer, et al., "Macrophage Inflammatory Protein (MIP)-1β brogates the Capacity of MIP-1α to Suppress Myeloid Progenitor Cell Growth", supra), and the cytokine-inducing effects of MIP-1α on macrophages. See, Fahey, et al., supra.

MIP-1α and MIP-1β are members of a larger family of molecules variously termed small inducible proteins, intercrine cytokines (see, Wolpe, et al., "Macrophage Inflammatory Proteins 1 and 2: Members of a Novel Superfamily of Cytokines", *FASEB J.*, Vol. 3, p. 2565 (1989); Oppenheim, et al., "Properties of the Novel Proinflammatory Supergene 'Intercrine' Cytokine Family", *Ann. Ref. Immunol.*, Vol. 9, p. 617 (1991); and Schall, "Biology of the Rantes/Sis Cytokine Family", *Cytokine*, Vol. 3, pp 165 (1991)), and more recently, chemokines. They are linked by amino acid homology, chromosome location and the presence in their primary sequence of 4 position invariant cysteine residues. The hu MIP-1 family, located on chromosome 17 and having a c-c motif, includes MIP-1α (=LD78), MIP-1β (=Act 2), Macrophage Chemotactic and Activating Factor (MCAF= muJE) and RANTES. The hu MIP-2 family located on chromosome 4 and having a c-x-c motif, includes GRO-α (also called melanoma growth stimulating factor=muKC), MIP-2α (=GRO-β), MIP-2β (=GRO-γ), Platelet Factor 4 (PF4), Interferon Inducible Protein-10 (IP-10), IL-8 (=neutrophil activating peptide (NAP)-1), and NAP-2 (which derives from platelet basic protein an its derivatives connective tissue activating peptide III and β-thromboglobulin).

SUMMARY OF THE INVENTION

One preferred embodiment of the present invention provides a process for suppressing myeloid cells in a mammal. The process comprises administering to a mammal for which such suppression is desired a synergistic combination of chemokines which suppress myeloid cells.

Another preferred embodiment of the present invention provides a process for suppressing myeloid cells in a mammal. The process comprises administering to a mammal for which such suppression is desired at least one chemokine which suppresses myeloid cells substantially in monomeric form.

Another preferred embodiment of the present invention provides a process for suppressing myeloid cells in a mammal. The process comprises administering to a mammal for which such suppression is desired an effective amount of at least one chemokine selected from the group consisting of Macrophage Inflammatory Protein-2α (MIP-2α), Platelet Factor 4 (PF4), Interleukin-8 (IL-8) and Macrophage Chemotactic and Activating Factor (MCAF).

Another preferred embodiment of the present invention provides a process for suppressing myeloid cells in a mammalian bone marrow cell population stimulated by multiple growth stimulating cytokines (such as a combination of colony stimulating factors, or one or more colony stimulating factors with another cytokine such as Steel Factor, c-kit ligand) in a culture medium. The process comprises including in said cell population a synergistic combination of at least two chemokines which suppress myeloid cells.

Still another preferred embodiment of the invention provides a composition which comprises a mammalian bone marrow cell population stimulated by multiple growth stimulating cytokines in a culture medium and having suppressed myeloid cells by a synergistic combination of at least two chemokines which suppress myeloid cells.

Another preferred embodiment of the present invention provides a process for blocking the myelosuppressive activity of IL-8 or PF4, comprising blocking said myelosuppressive activity with an effective amount of a chemokine selected from the group consisting of MIP-2β and GRO-α.

Still another preferred embodiment of the invention provides a composition for suppressing myeloid cells which comprises at least one chemokine which suppresses myeloid cells substantially in monomeric form.

A still further preferred embodiment of the invention provides a composition for suppressing myeloid cells which comprises a synergistic combination of chemokines which suppress myeloid cells.

Advantageously, when using synergistic combinations of chemokines in methods of the invention, the chemokines are effective at concentrations far below those necessary when the chemokines are used individually. Likewise, when compositions containing the chemokines predominantly in monomeric form are used, far less of the chemokine material needs to be used to achieve advantageous suppression of myeloid cells.

Methods and compositions of the present invention thus provide myeloprotectant effects which can be used in conjunction with therapies which may adversely affect myeloid cells. For example, administration of chemokines according to the invention, e.g. by injection into the mammal to undergo therapy, can place myeloid cells in a myeloprotected, slow-cycling state. Cell damage caused by subsequent radiation therapy or chemotherapy using cell-cycle active drugs, such as cytosine arabinoside and hydroxyurea, can thereby be reduced.

Methods and compositions of the invention also provide myelosuppressive effects which can be used in the treatment of disorders such as leukemia that cause hyperproliferative myeloid cell states or of disorders causing hypoproliferative myeloid cell states. Administration of chemokines according to the invention, e.g. by injection intraveneously or subcutaneously, can suppress proliferation of myeloid cells, or can block suppression of myeloid cells.

Methods and compositions of the invention also provide for suppressed or suppression-blocked myeloid cell populations which can be used in ex vivo therapies or in studies of disorders such as leukemia or of side-effects such as those resulting from radiation- or chemo-therapy, e.g. in this regard in the screening of agents or therapies for their adverse or modulative effects on myeloid cells.

Additional embodiments, objects and advantages of the invention will be apparent from the description herein.

DESCRIPTION OF THE FIGURES

FIGS. 3A, 3B, and 3C: Influence of chemokines, alone and in combination, on colony formation by: FIG. 1A) CFU-GM, FIG. 1B) BFU-E, and FIG. 1C) CFU-GEMM in low density bone marrow cells stimulated by GM-CSF and SLF for CFU-GM, and by Epo and SLF for BFU-E and CFU-GEMM. The key for symbols is to the right of each of the graphs. The symbols in the graph are each inclusive of the mean plus SEM bars. In some cases points were so close together that they clustered into one pattern, the most striking of which is shown for the combinations of chemokines at 1.0 ng+1.0 ng each in the key to the far right.

FIG. 6A) diluted in PBS to a final concentration of >20 ng/ml and eluted with PBS, and FIG. 6B) both diluted and eluted in ACN. Superose-12 columns (Parmacia, Uppsala) were pre-equilibrated with appropriate buffers, 0.2 ml sample (7 µg MIP-1α) was injected, and columns were eluted at a flow rate of 0.5 ml/min. Protein elution was continuously monitored by absorption at 280 nm wavelength using FPLC system (Pharmacia). Columns were calibrated for molecular weight using a marker kit from Bio Rad (Richmond, Calif.). Calibration was done independently in each buffer. Quantitation of MIP-1α (FIG. 6C) was accomplished by immuno-blotting of SDS-PAGE-separation 8 KD samples with anti-MIP-1α antibodies and subsequent densitometry. Lanes 1 to 5 contain respectively 0.1, 0.5, 1.0, 2.0, and 3.0 ng/ml MIP-1α from stock solutions in ACN. Lanes 6 and 7 respectively contain $10_{-3}$ and $10^{-2}$ dilutions of polymerized MIP-1α from the peak in FIG. 6A. Lanes 8 and 9 respectively contain $10^{-1}$ dilution and undiluted monomeric MIP-1α from the portion of A that corresponds to the peak in FIG. 6B. After densitometric scanning, peak areas of lanes 1 to 5 were plotted against rmuMIP-α concentrations to generate standard curves (FIG. 6C) from which concentrations of MIP-1α, such as those in lanes 6 to 9 were extrapolated ($r^2$=0.95). For western blot analysis, MIP-1α samples were boiled for 5 min. in SDS sample buffer containing 2 mer-captoethanol and subjected to 15% SDS-PAGE. Proteins resolved on the gel were transblotted onto Immunobilon-P membrane (Millipore Corp., Bedford Mass.) and visualized by staining.

In FIG. 9A, $BDF_1$ mouse marrow cells were pulse-treated with either control (McCoy's) medium or high specific activity tritiated thymidine ($^3$HTdr, 50 uCi/ml, specific activity: 20 Ci/mmol) for 30 min. at 37° C. prior to washing cells 2× and plating cells in the presence of control diluent (ACN) or 0.1 ng/ml monomeric rmuMIP-1α. In FIG. 9B, marrow cells were pulsed for 30 min. at 37° C. first with either control (McCoy's) medium, diluent (ACN), $^3$HTdr, or MIP-1α and washing cells 2×. Pulsed cells were plated in the presence of diluent of 0.1 ng monomeric rmuMIP-α/plate. Decrease in colony formation after pulse exposure of cells to high specific activity $^3$HTdr estimates of the percent of CFU-GM in DNA synthesis (S)-phase of the cell cycle at the time of pulse exposure. Cells in FIG. 9A were stimulated by 100 U/ml rmuGM-CSF, or 100 U/ml rmuGM-CSF plus 50 ng/ml rmuSLF. Cells in part B were stimulated by GM-CSF plus SLF. Colonies and clusters (3–40 cells/group) are expressed per $7.5\times10^4$ cells/plate. Two experiments are shown and similar results were seen also in one other experiment.

FIGS. 12A, 12B and 12C: Time sequence analysis of the effects of a single i.v. injection of MIP-α (8 ng) on percentages of: FIG. 12A) CFU-GM, FIG. 12B) BFU-E, and FIG. 12C) CFU-GEMM in cycle in the bone marrow and spleen of C3H/HeJ mice. Results are averages of 2 experiments in which a total of 6 mice were individually assessed per group. The % progenitors in cycle are based on colony numbers of cells treated with McCoy's medium which ranged from 44–72 for marrow and 71–110 for splenic CFU-GM, from 19–42 for marrow and 30–75 for splenic BFU-E, and from 12–27 for marrow and 17–36 for splenic CFU-GEMM. Significant % change from diluent control: *p<0.01; **p 0.001; other numbers are not significantly different from control, p>0.05.

FIGS. 13A, 13B and 13C: Time sequence analysis of the effects of a single i.v. injection of monomeric rmuMIP-1α (8 ng) on absolute numbers of: FIG. 13A) CFU-GM, FIG. 13B) BFU-E, and FIG. 13C) CFU-GEMM in the bone marrow and spleen of C3H/HeJ mice. Significant change from control diluent: *p<0.01; **p<0.001; other numbers are not significantly different from control, p>0.05.

FIG. 16A) CFU-GM; FIG. 16B) BFU-E; FIG. 16C) CFU-GEMM. CFU-GM were plated in the presence of rGM-CSF (100 U/ml) and rSLF (50 ng/ml). CFU-GEMM and BFU-E were plated in the presence of rEpo (1 U/ml) and rSLF (50 ng/ml). Results are given as the mean±SEM and reflect 3 separate experiments with rIP-10, and 2–3 experiments for the other chemokines. Percent change from control designates suppression and was based on control colony numbers for CFU-GM (59±2 to 106±7), BFU-E (58±4 to 105±2), and CFU-GEMM (37±3 to 68±1). Most symbols in the graphs are smaller than the SEM, which was always ≦12% of the mean percent change.

DESCRIPTION

Figure 1:
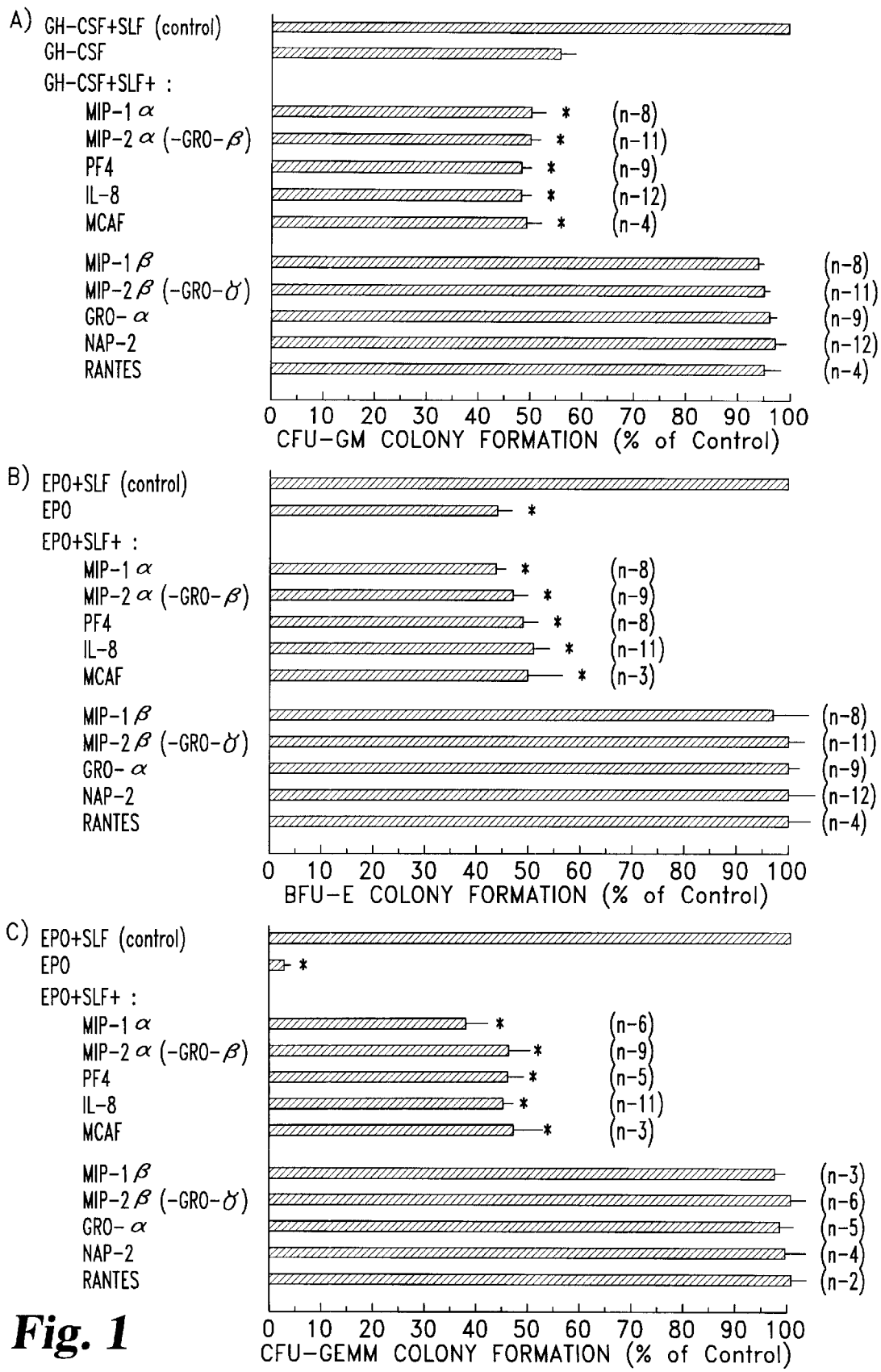
FIGS. 1A, 1B, and 1C: Influence of chemokine molecules on colony formation by FIG. 1A) CFU-GM, FIG. 1B) BFU-E, and FIG. 1C) CFU-GEMM in $10^5$ low density normal human bone marrow cells. Control colony numbers for CFU-GM plated in the presence of GM-CSF plus SLF, and for BFU-E and CFU-GEMM plated in the presence of Epo plus SLF were respectively: 130±13 (mean±1 SEM, range: 59 to 197 for 13 marrows), 83±11 (range: 45 to 162 for 11 marrows), and 38±6 (range: 11 to 71 for 11 marrows). "*" designates significant change, p<0.01 compared to control values; other values were not significantly different from control, p>0.05. n in parenthesis designates the number of different test marrows studied.

For the purposes of promoting an understanding of the principles of the invention, reference will now be made to preferred embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention pertains.

The following abbreviations are used herein: MIP, macrophage inflammatory protein; MCAF, macrophage chemotactic and activating factor; PF4, platelet factor 4; IL, interleukin; NAP, neutrophil activating peptide; IP, Interferon Inducible Protein; CFU-GEMM, multipotential progenitor cell; BFU-E, erythroid progenitor cell; CFU-GM, granulocyte macrophage progenitor cell; CSF, colony stimulating factor(s); GM, granulocyte macrophage; Epo, erythropoietin; NALDT$^-$, non-adherent low density T-lymphocyte depleted; mu, murine; hu, human; r, recombinant; CFU-S, colony forming unit spleen, a subset of the pluripotent stem cells; LD, low density; SLF, steel factor.

The present invention provides compositions and methods for suppressing myeloid cells. In this regard, as used herein, the term "suppress" and its derivatives are meant to refer to decreasing the proliferation of myeloid cells and/or increasing the percentage of myeloid cells which are in the slow-cycling phase.

Several aspects of the invention involve the administration of chemokines or combinations of chemokines to mammals. It will be understood that the chemokines or their combinations can be administered in suitable pharmaceutical preparations. Such pharmaceutical preparations may include, for example, pharmaceutically acceptable carriers such as inert solid diluents or fillers, sterile aqueous solution and various organic solvents. Pharmaceutical compositions formed by combining a chemokine or chemokines according to the invention and the pharmaceutically acceptable carriers are then easily administered in a variety of dosage forms such as injectable solutions.

For parenteral administration, solutions of the protein in oils such as sesame or peanut oil, aqueous propylene glycol, or in sterile aqueous solution (desirably isotonic) may be employed. These aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The preparations of the present invention may be used in conjunction with a variety of chemotherapy agents. Some classes of agents include alkylating agents such as nitrogen mustards, ethylenimines and methylmelamines, alkyl sulfonates, nitrosoureas, triazenes and the like; antimetabolites such as folic acid analogs, pyrimidine analogs, in particular fluorouracil and cytosine arabinoside, and purine analogs and the like; natural products such as vinca alkaloids, epipodophyllotoxins, antibiotics, enzymes and biological response modifiers; and miscellaneous products such as platinum coordination complexes, anthracenedione, substituted urea such as hydroxyurea, methyl hydrazine derivatives, adrenocorticoid suppressants and the like. See for example, Goodman and Gilman's *The Pharmacological Basis of Therapeutics,* 8th edition, Pergamon Press, section XII.

The chemotherapy agents are administered orally, intravenously, intramuscularly, intrapleurally or intraperitoneally at doses based on the body weight and degree of disease progression of the patient, and may be given in one, two or even four daily administrations. Dosages range from about 0.5 mg/kg per day up to tens and even hundreds of mg/kg per day. Compositions of the present invention may be co-administered with the chemotherapeutic agent, or may be administered separately, either before and concurrently with the chemotherapy agent. Dosages of the myelosuppressive agent may vary widely, depending on several factors including the body weight of the patient and on the type and amount of chemotherapy agent administered. Suitable dosages, for example, may be up to about 100 $\mu$g/kg or more per day, e.g. from about 3 $\mu$g/kg per day to about 100 $\mu$g/kg per day, with the precise dosage being determined in accordance with the situation at hand. The dosage of myelosuppressive agent will in general be sufficient to increase the percentage of myeloid cells in the slow-cycling phase so as to achieve myeloprotection, and may be administered intravenously, intramuscularly or intraperitoneally, for example.

Representative chemokines which are useful in the various embodiments of the invention include those which suppress myeloid cells, such as Macrophage Inflammatory Protein-2$\alpha$ (MIP-2$\alpha$), Platelet Factor 4 (PF4), Interleukin-8 (IL-8), Macrophage Chemotactic and Activating Factor (MCAF), and Interferon Inducible Protein-10 (IP-10). It will be appreciated that the myeloid-cell-suppressive chemokine to be utilized in the present invention can be any substance, of natural or synthetic origin, which exhibits the properties of a natural myeloid-cell-suppressive chemokine. It is now well established practice to synthesize such chemokines and other such substances by the use of genetically modified microorganisms. It may oftentimes be convenient or even preferred that such processes yield a modified chemokine, that is, a substance that differs as to its structure from the naturally occurring chemokine, but which retains the biological activity of the naturally occurring chemokine. For example, a modified chemokine may contain one or more additional amino acids, at one or both ends of the polypeptide chain; may have an amino acid sequence which differs from that of the naturally occurring chemokine; or may be an active fragment of a naturally-occurring chemokine. Therefore, the term chemokine is used throughout this document to refer to both naturally occurring chemokines as well as synthetically produced substances which share the biological properties of naturally-occurring chemokines, and which may be identical or which may vary somewhat as to structure.

A feature of this invention is the discovery that substantially monomeric preparations of myeloid-cell-suppressive chemokines have a much greater suppressive effect than heretofore known and used preparations substantially comprised of non-monomeric forms of the chemokines. In this regard, additional advantageous chemokine compositions to be used in the present invention will be predominantly comprised (i.e. 50+ wt. %) of monomeric chemokine, more preferably at least about 80%, and most preferably about 90% to about 100%, in order to achieve significant increases in suppressive activity as demonstrated in the specific experimental below.

The following Experimental is provided by way of illustration and not by way of limitation of the invention.

Experimental

General Materials/Methods

Cells and Cell Separation Procedures. Hu bone marrow cells were obtained by aspiration from the posterior iliac crest of healthy volunteers who had given informed consent. Low density cells (LD, <1.077 g/cm$^3$) were retrieved after density cut separation on Ficoll-Hypaque (Pharmacia Fine Chemicals, Piscataway, N.J.). Hu bone marrow was further enriched for myeloid progenitor cells by obtaining fractions of non-adherent low density T-lymphocyte depleted (NADLT$^-$) fluorescence-activated cell-sorted CD34$^{+++}$ HLA-DR$^+$ cells. See, Lu, et al., "Characterization of Adult Human Marrow Hematopoietic Progenitors Highly Enriched by Two-Color Sorting with My10 and Major Histocompatibility (MHC) Class II Monoclonal Antibodies", *J. Immunol.*, Vol. 139, pp. 1823 (1987). A Coulter 753 Flow Cytometry System (Hialeah, Fla.) was used to sort for the highest density of CD34$^{+++}$ cells which represent approximately 1% of the starting population of NALDT$^-$ cells and is most enriched for progenitor cells within the total population of CD34 expressing cells. See, Broxmeyer, et al., "Enhancing and Suppressing Effects of Recombinant Murine Macrophage Inflammatory Proteins on Colony Formation in vitro by Bone Marrow Myeloid Progenitor Cells", supra.

Hu Cytokines. All cytokines were purified. Recombinant MIP-1α, MIP-1β, MIP-2α and MIP-2β were produced using yeast expression vectors (see, Tekamp-Olson et al., "Cloning and Characterization of cDNAs for Murine Macrophage Inflammatory Protein 2 and Its Human Homologues", *J. Exp. Med.*, Vol. 172, pp. 911 (1990)) and were obtained from Chiron Corp. Emeryville, Calif. Recombinant GRO-α was from Immunex Corp., Seattle, Wash. Recombinant preparations of MCAF, RANTES and the 77 and 72 amino acid forms of IL-8 were purchased from Pepro Tech, Inc., Rocky Hills, N.J. The 77 amino acid form of recombinant IL-8 and the natural form of PF4 were purchased from Sigma Chemical Co., St. Louis, Mo. Recombinant NAP-2 was purchased from Bachem Bioscience, Philadelphia, Pa. Recombinant IP-10 was obtained as described below. Recombinant erythropoietin (Epo) was purchased from Amgen Corp., Thousand Oaks, Calif. Recombinant granulocyte-macrophage colony stimulating factor (GM-CSF), IL-3 and Steel Factor (SLF, also called mast cell growth factor, stem cell factor and c-kit ligand) were from Immunex Corp.

Colony Assays. LD and NALDT$^-$ cells were respectfully plated at $10^5$ and $2.5 \times 10^4$ cells/ml in either 0.3% agar culture medium for assessment of CFU-GM or in 0.9% methylcellulose culture medium for assessment of CFU-GEMM and BFU-E as described previously in Broxmeyer, et al., "Enhancing and Suppressing Effects of Recombinant Murine Macrophage Inflammatory Proteins on Colony Formation in vitro by Bone Marrow Myeloid Progenitor Cells", supra; Broxmeyer, et al., "Macrophage Inflammatory Protein (MIP)-1β Abrogates the Capacity of MIP-1α to Suppress Myeloid Progenitor Cell Growth", supra; and Broxmeyer, et al., "Effect of Murine Mast Cell Growth Factor (c-kit Proto-oncogene Ligand) on Colony Formation by Human Marrow Hematopoietic Progenitor Cells", *Blood*, Vol. 77, pp. 2142 (1991). CFU-GM colonies (>40 cells/group) were stimulated by rhuGM-CSF (100 U/ml), alone or in combination with rhuSLF (50 ng/ml) and CFU-GEMM and BFU-E colonies were stimulated by rhuEpo (1–2 U/ml), alone or in combination with rhuSLF (50 ng/ml). NALDT$^-$ CD34$^{+++}$HLA-DR$^+$ cells were plated in methylcellulose with Epo (2 U/ml), SLF (50 ng/ml), IL-3 (200 U/ml) and GM-CSF (200 U/ml) at concentrations ranging from 100 to 400 cells/ml. The concentrations of GM-CSF and Epo used give plateau numbers of colonies when used alone, and SLF synergizes with either Epo or GM-CSF to respectfully enhance the numbers and size of CFU-GEMM/BFU-E and CFU-GM colonies. See, Broxmeyer, et al., "Effect of Murine Mast Cell Growth Factor (c-kit Proto-oncogene Ligand) on Colony Formation by Human Marrow Hematopoietic Progenitor Cells", supra. Colonies were scored after 14 days incubation at lowered (5%) $O_2$ tension, and 5% $CO_2$ in a humidified environment in an ESPEC $N_2$—$O_2$—CO incubator BNP-210 (Taboi ESPEC Corp., South Plainfield, N.J.). Three plates were scored per determination.

Statistics. Levels of significance were determined using student's t distribution (2 tailed test).

Results

Influence of Chemokines on Colony Formation rhu preparations of MIP-1α, MIP-1β, MIP-2α, MIP-2β, IL-8, MCAF, GRO-α, NAP-2, RANTES, and natural hu PF4 were each assessed at concentrations of 10, 25, 50, 100 and 1000 ng/ml for effects on colony formation by $10^5$ low density bone marrow cells/ml. Cells were plated either in the absence of added colony stimulating factors, or in the presence of rhuGM-CSF (100 U/ml) −/+rhuSLF (50 ng/ml) for CFU-GM, and rhuEpo (1 U/ml) −/+rhuSLF (50 ng/ml) for CFU-GEMM and BFU-E. In the absence of added colony stimulating factors, no CFU-GM, BFU-E or CFU-GEMM colonies grew, and none of the chemokines at the concentrations tested stimulated colony formation. Moreover, the chemokines had no significant effect on colony formation of CFU-GM stimulated by maximally effective concentrations of GM-CSF or of BFU-E and CFU-GEMM stimulated by maximal levels of Epo. (For example, the percentage change from control values for each assay in the presence of chemokines ranged from −8 to +10, p>0.05, based on respective control colony numbers of CFU-GM, BFU-E and CFU-GEMM of 25 to 55, 15 to 35 and 1 to 3).

Figure 16A:
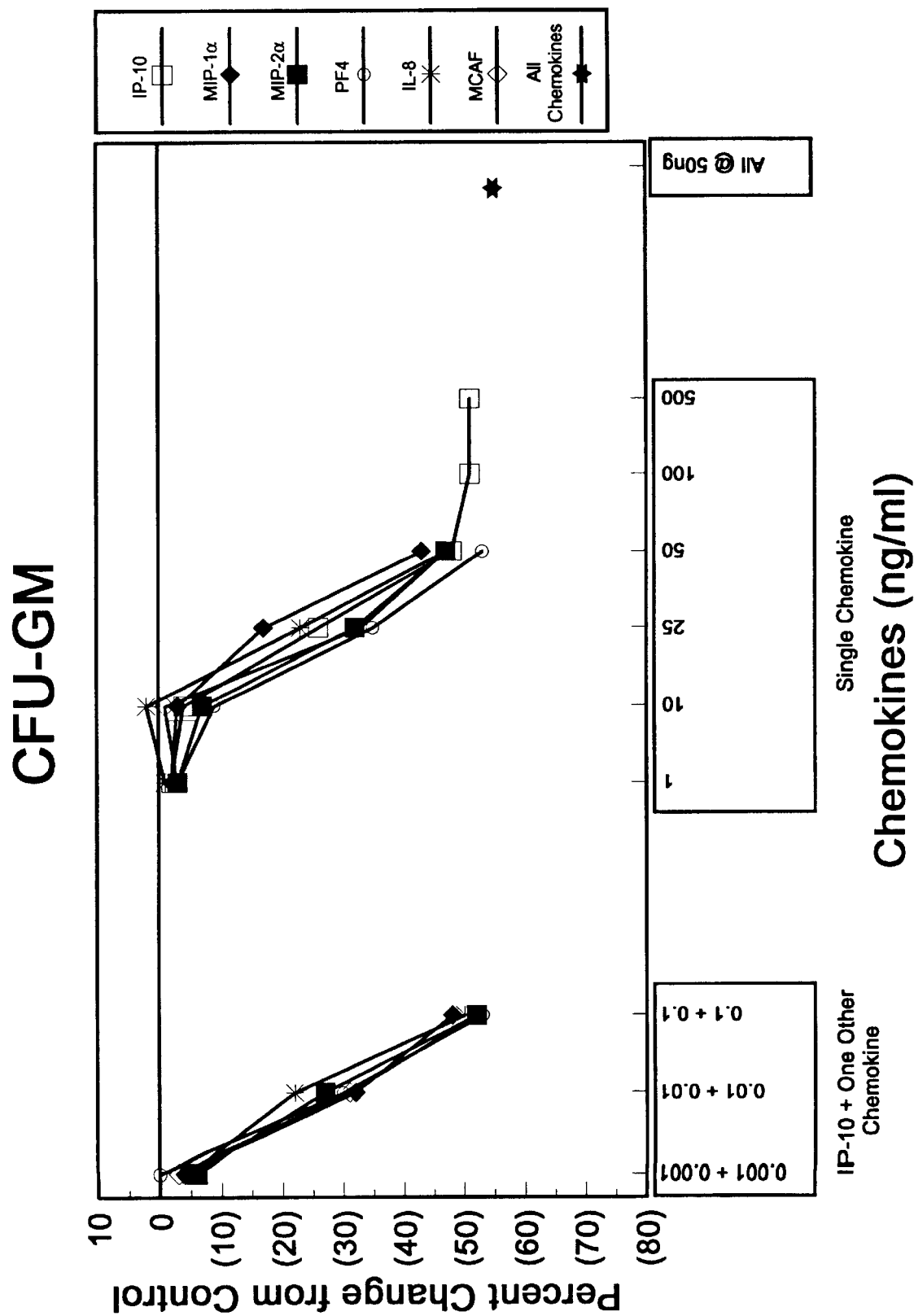
FIGS. 16A, 16B and 16C: Influence of rIP-10 on colony formation.
Figure 16B:
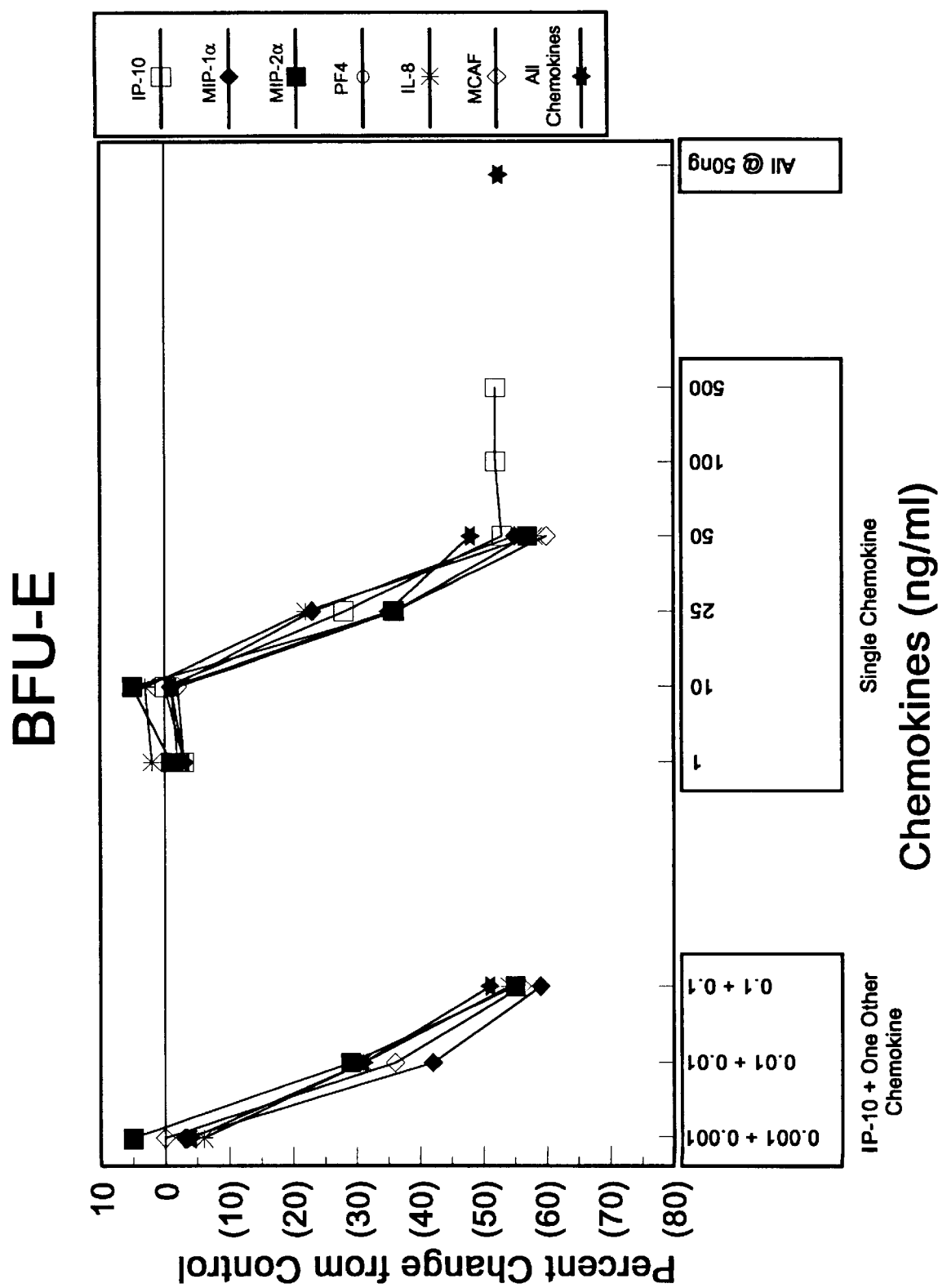
Figure 16C:
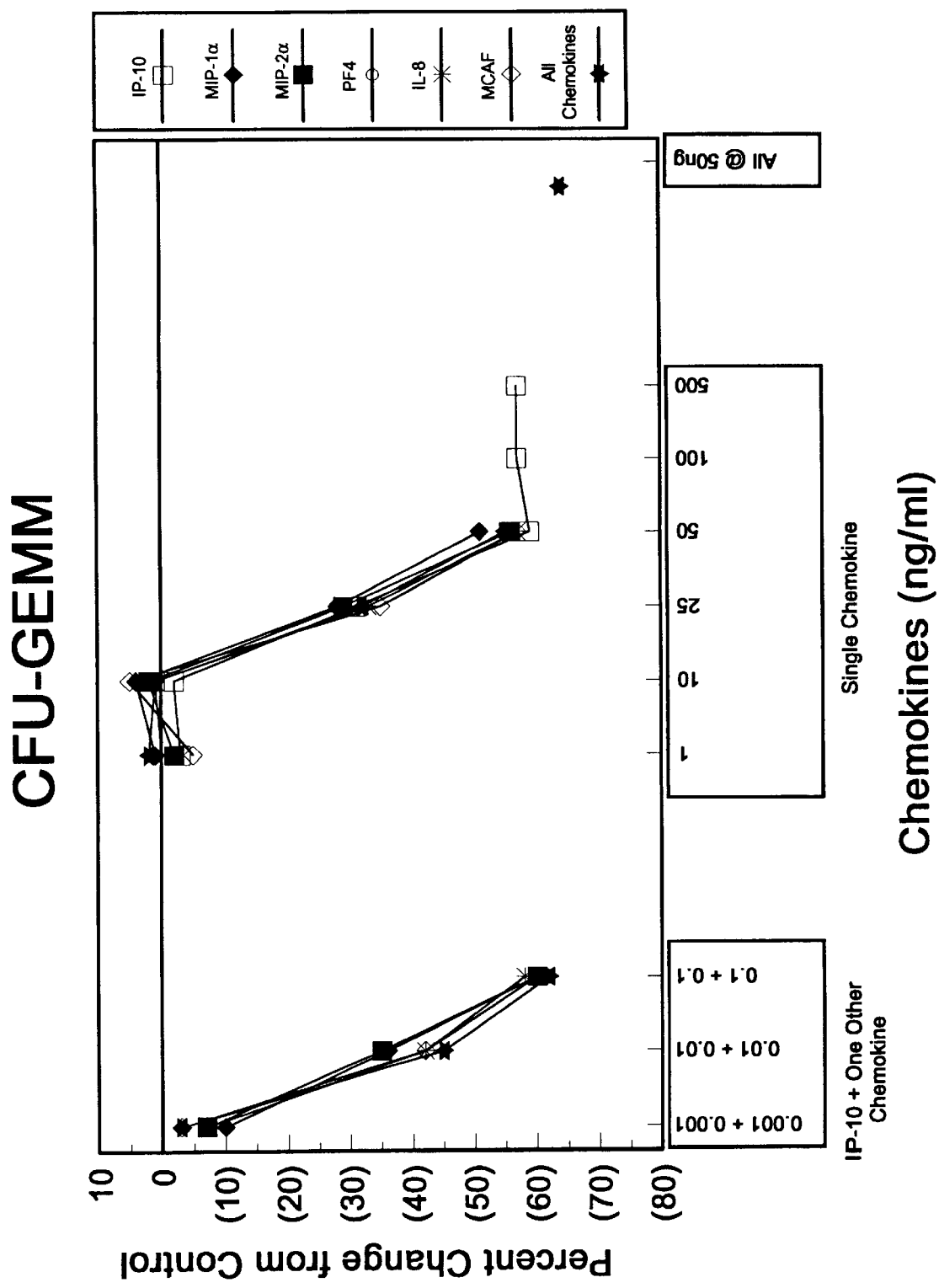

Chemokines were also each assessed at 100 ng for effects on CFU-GM colony formation stimulated by the combination of GM-CSF and SLF (FIG. 1A), and on BFU-E (FIG. 1B) and CFU-GEMM (FIG. 1C) colony formation stimulated by Epo and SLF. MIP-1α, MIP-2α, PF4, IL-8 and MCAF each significantly reduced total colony formation of CFU-GM, BFU-E and CFU-GEMM by about 50% (p<0.01) and completely suppressed the SLF-enhanced colony formation of CFU-GM and BFU-E. The different forms of IL-8, which included the 72 amino acid samples from two different companies or the 77 amino acid sample, were equally suppressive. Maximum suppression was apparent with 100 ng/ml of each cytokine. No greater suppression was noted when concentrations up to 1000 ng/ml were used. The suppressive effects were lost between 25–50 ng/ml. MIP-1β, MIP-2β, GRO-α, NAP-2 and RANTES did not influence colony formation by myeloid progenitors at 100 ng/ml (FIGS. 1A, B, C) or at 1000 ng/ml. Thus, the hu preparations of MIP-1α, MIP-2α, PF4, IL-8 and MCAF have myelosuppressive effects similar to rmuMIP-α, (see, Broxmeyer, et al., "Enhancing and Suppressing Effects of Recombinant Murine Macrophage Inflammatory Proteins on Colony Formation in vitro by Bone Marrow Myeloid Progenitor Cells", supra; and Broxmeyer, et al., "Macrophage Inflammatory Protein (MIP)-1β Abrogates the Capacity of MIP-1α to Suppress Myeloid Progenitor Cell Growth", *J. Immunol.*, Vol. 147, pp. 2586 (1991))

rhuIP-10, prepared as described below, was also assessed alongside MIP-1α, MIP-1β MIP-2α, MIP-2β, IL-8 and MCAF for influence on colony formation. Thus, in a fashion analogous to that described above, the influence of the chemokines at varying concentrations was tested on CFU-GM cells plated in the presence of rhuGM-CSF (100 U/ml) and rhuSLF (50 ng/ml), and on CFU-GEMM and BFU-E cells plated in the presence of rhuEpo (1 U/ml) and rhuSLF (50 ng/ml). The results of this testing using individual chemokines are shown in FIG. 16A–C ("Single Chemokine" data), and demonstrate that IP-10 suppresses colony formation in a fashion similar to the other chemokines.

Effects on Purified Myeloid Progenitor Cells

Figure 2:
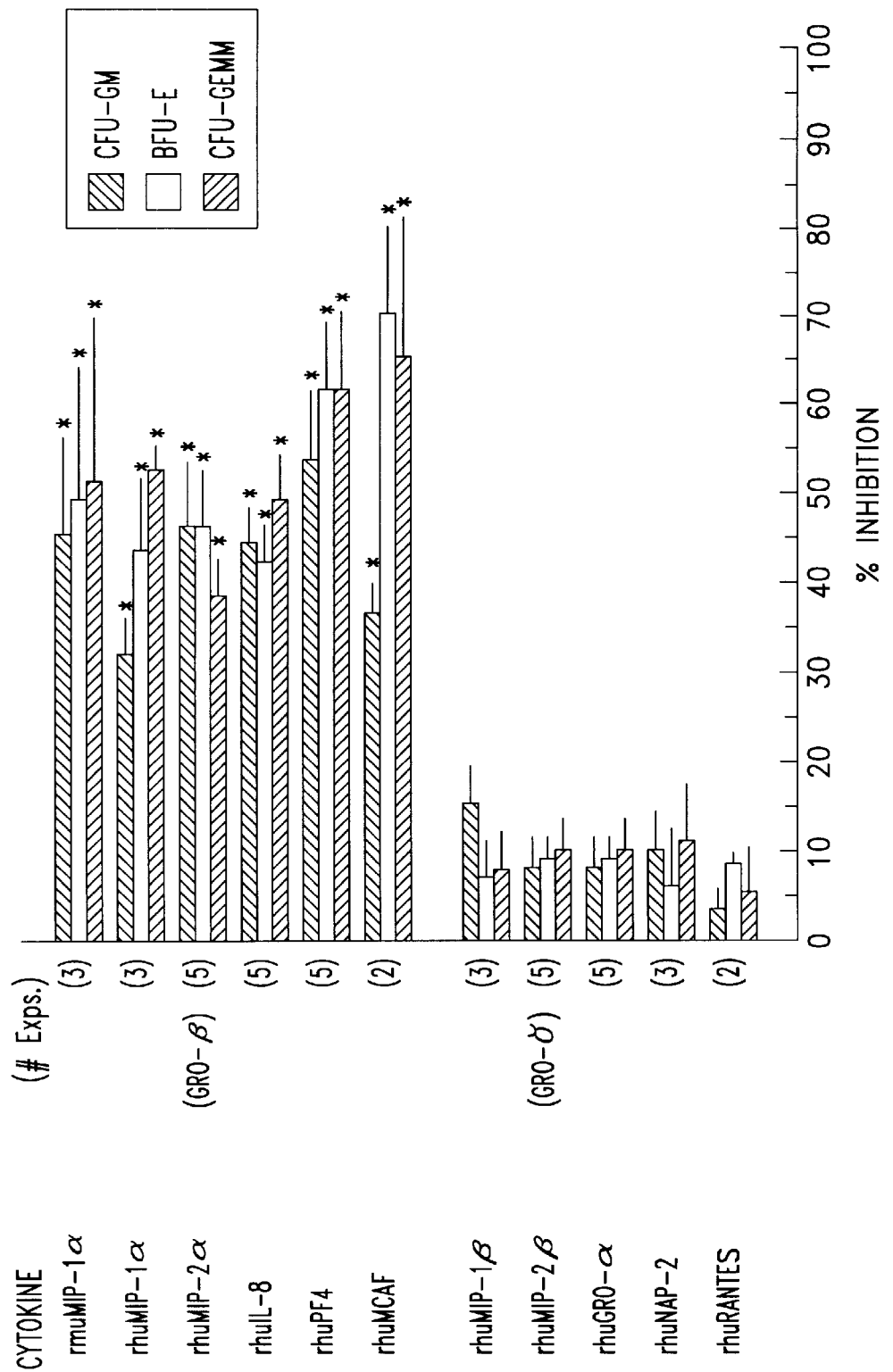
FIG. 2: Percent inhibition of colony formation by highly enriched populations of myeloid progenitor cells present in NALDT$^-$ CD34$^{+++}$ HLA-DR$^+$ normal human bone marrow cells. Cloning efficiencies scored from the same plates for 100 to 400 cells plated/ml for CFU-GM plus BFU-E plus CFU-GEMM averaged 53±7% (mean=/−1 SEM; range: 32 to 77% for 5 experiments). "*" designates p<0.01 compared to growth without chemokines molecules; other values not significantly different, p>0.05.

To evidence whether the effects of the chemokines on colony formation by human bone marrow cells are direct acting on the progenitor cells, each hu chemokine was assessed at 100 ng/ml for effects on colony formation by 100 to 400 NALDT$^-$ CD34$^{+++}$HLA-DR$^+$ cell/ml stimulated by the combination of Epo (2 U/ml), SLF (50 ng/ml), IL-3 (200 U/ml) and GM-CSF (200 U/ml). The highly enriched progenitor cell content of this fraction of cells is demonstrated by the 53±7% cloning efficiency (mean±1 SEM; range 32 to 77% for 5 experiments) for total colonies (CFU-GM, BFU-E and CFU-GEMM), stimulated under these conditions when chemokines were not present. As shown in FIG. 2, rmuMIP-1α as well as the hu preparations of MIP-1α, MIP-1β, IL-8, PF4 and MCAF significantly suppressed colony formation of CFU-GM, BFU-E and CFU-GEMM by 30–70%. MIP-1β, MIP-2β, GRO-α, NAP-2 and RANTES were without effect on these purified cells. Since a highly enriched population of progenitor cells was used, and suppression was similar to that seen using relatively unseparated LD cells (FIG. 1), the results evidence that rhuMIP-1α, rhuMIP-2α, rhuIL-8, huPF4 and rhuMCAF are directly suppressing myeloid progenitor cell proliferation.

Effects on Single Isolated Clonogenic Cells

To further evidence that the effects of the chemokines on colony formation by human bone marrow cells are direct acting on progenitor cells, hu cytokines were assessed for effects on colony formation by single $CD34^{+++}$ cells from normal human bone marrow stimulated by the combination of Epo, SLF, IL-3 and GM-CSF. More particularly, CD34+++. cells obtained $NALDT^-$ cells were separated on a Coulter Epics 753 dual Laser Flow Cytometer and a single cell labeled with anti-CD34 (monoclonal anti-HPCA-1, Becton Dickinson, Mountain View, Calif.) was directly sorted into one well of a 96 well microtiter plate containing 0.1 ml methylcellulose culture medium using an auto-clone device (Coulter) with documentation that one cell was placed into one well. Cultures contained Iscove's Modified Dulbecco's medium, 1.3% methylcellulose, 30% fetal bovine serum (Hyclone Laboratory, Logan Utah) and 0.1 mM hemin (Eastman Kodak Co., Rochester, N.Y.). Serum-depleted cultures contained bovine serum albumin (1 mg/ml), iron-saturated transferrin (300 µg/ml), cholesterol (7.8 µg/ml) and $CaCl_2$ (200 µg/ml) instead of serum. Cells were incubated at 5% $CO_2$, 5% $O_2$ and 37° C. in a humidified chamber for 14 days and were assessed for colony formation by relatively immature subsets of granulocyte-macrophage (CFU-GM), erythroid (BFU-E), multipotential (CFU-GEMM) and high proliferative potential (HPP-CFC) cells, stimulated by a combination of growth-stimulating cytokines. SLF, IL-3 and GM-CSF were used respectively at concentrations of 50 ng, 200 U, and 200 U per ml. Rhu Epo was used at 1 U/ml. rhu H-ferritin and the inactive rhu H-ferritin mutein 222 were gifts from Drs. Paolo Arosio and Sonja Levy, University of Milan, Milan, Italy. TGF-β1 was purchased from Genzyme Co., Cambridge, Mass. rmu MIP-1α was purchased from R & D Systems, Minneapolis, Minn. Suppressive cytokines were used at 200 ng/ml, except for TGF-β1 (5 ng/ml), monomeric rmuMIP-1α (0.5 ng/ml), the active form of MIP-1, rhu H-ferritin ($10^{-10}$M) and the rhu H-ferritin mutein 222 ($10^{-10}$M), an inactive form of H-ferritin. The rmuMIP-1α could be used at lower concentrations (0.5 ng/ml) than the other chemokines (200 ng/ml) because it was entirely in the active monomeric form. The other chemokines were only partially in active form. Cycling status of hematopoietic stem and progenitor cells was estimated as the proportion of stem and progenitor cells in DNA synthesis as described further below. Briefly, the high specific activity (20 Ci/mmol) tritiated thymidine (50 µCi/ml, New England Nuclear, Boston, Mass.) kill technique was used which is based on calculation of the reduction in the number of colonies formed after pulse exposure of cells for 20 min to $^3$H-thymidine as compared with the growth of cells after pulse exposure to control medium. For analysis of the percent cells in S-Phase, three or more plates were scored for colony formation and the results expressed as mean±1SEM. The probability of significant differences between groups in the single cell experiments was determined by $x^2$ test.

Figures 17A, 17B:
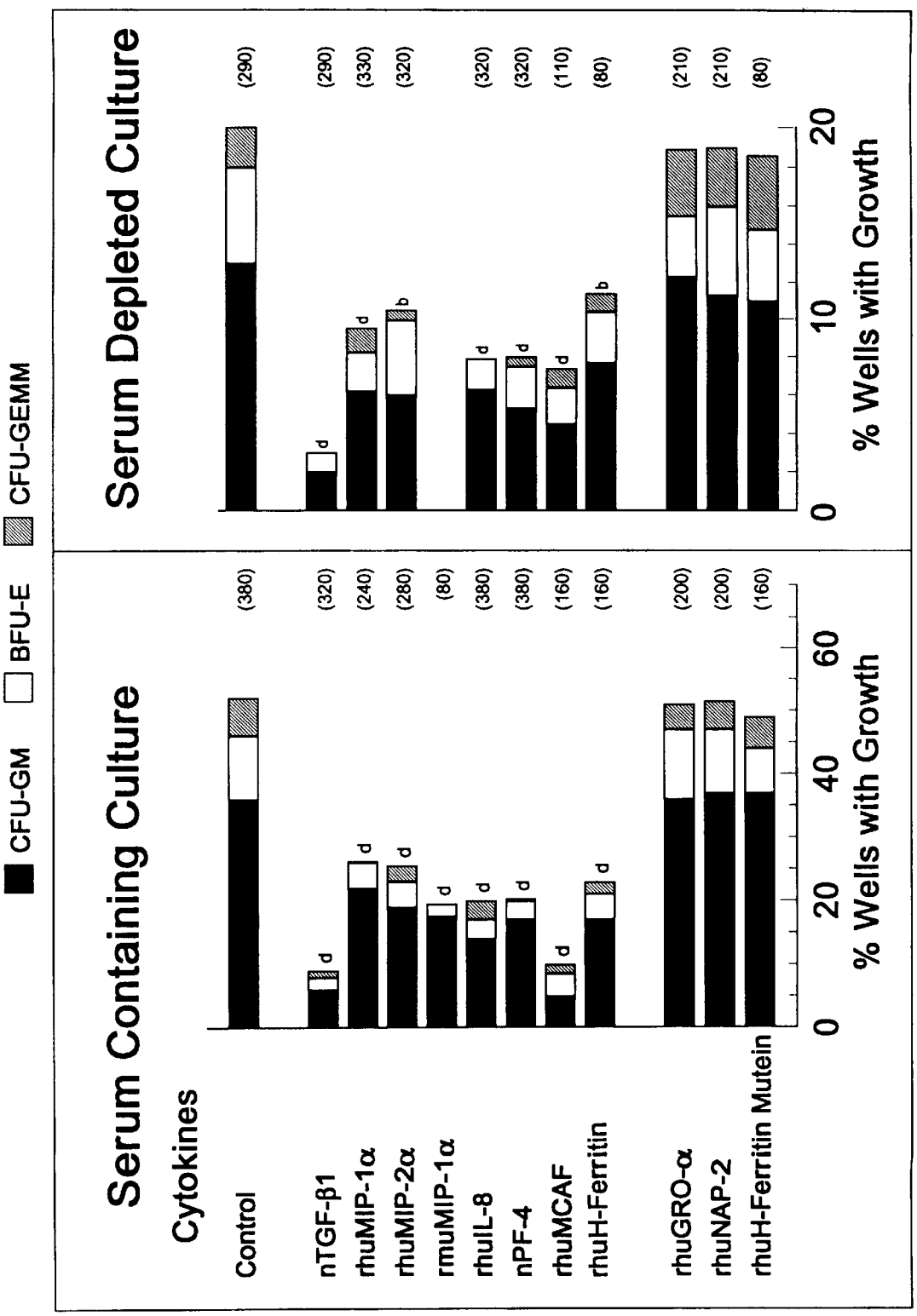
FIG. 17: Influence of suppressive cytokines on colony formation by single CD34+++ cells from normal human bone marrow stimulated by Epo (1 U/ml), SLF (50 ng/ml), IL-3 (200 U/ml) and GM-CSF (200 U/ml) in the presence (A) and absence (B) of serum. The numbers in the parentheses to the right of each bar represent the total number of wells evaluated. The results are from a total of five (serum containing) and three (serum depleted) separate experiments. Significant differences from medium control for total colonies are designated as $^a$p<0.001; $^b$p<0.05.

The results are shown in FIG. 17. Bone marrow (BM) blood $CD34^{+++}$ cells were sorted into single wells in the presence of Epo, SLF, IL-3 and GM-CSF, in the presence (FIG. 17A) or absence (FIG. 17B) of serum, and assessed for their responsiveness to a number of different cytokines with previously demonstrated suppressive activity against low density and more purified bone marrow cells. As shown in FIG. 17, in the absence of suppressive cytokines the percentages of wells with a cell forming a colony for BM (–serum), and BM (+ serum) were respectively 48.6 and 21.4. TGF-β1, rhuMIP-1α, rhuMIP-2α, rmuMIP-1α, rhuIL-8, PF4, rhuMCAF and rhuH-ferritin respectively suppressed growth of total bone marrow colonies growing in the presence of serum (FIG. 17A) by 81.3%, 45.1%, 49.4%, 58.8%, 58.2%, 58.2%, 79.4% and 52.7% (p<0.001) and suppressed growth of total bone marrow colonies growing in the absence of serum (FIG. 17B) by 85.5%, 57.5%, 50.5%, not done, 63.6%, 62.1%, 65.9% and 58.9% (p<0.05 to<0.001). Significant suppression (p at least <0.05) of each colony type was observed with these cytokines. RhuH-ferritin mutein 222 and the chemokines rhuGRO-α and rhuNAP-2, previously shown to be inactive as suppressor molecules, were not suppressive at the level of a single cell growing in the presence (FIG. 17A) or absence (FIG. 17B) of serum (p>0.05). The results of this set of experiments further document that the effects of the cytokines are direct on progenitor cells.

Figure 3A:
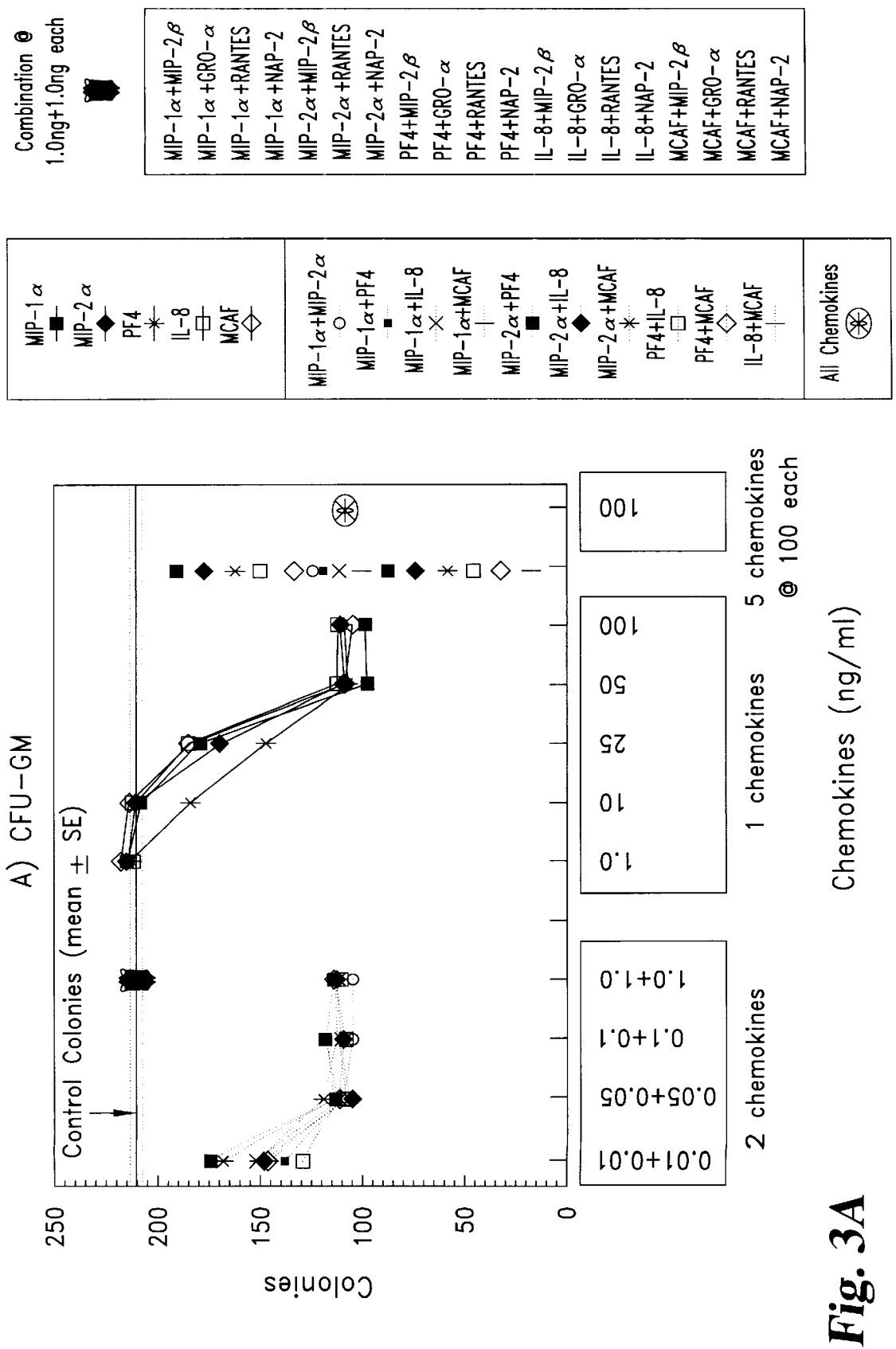
Figure 3B:
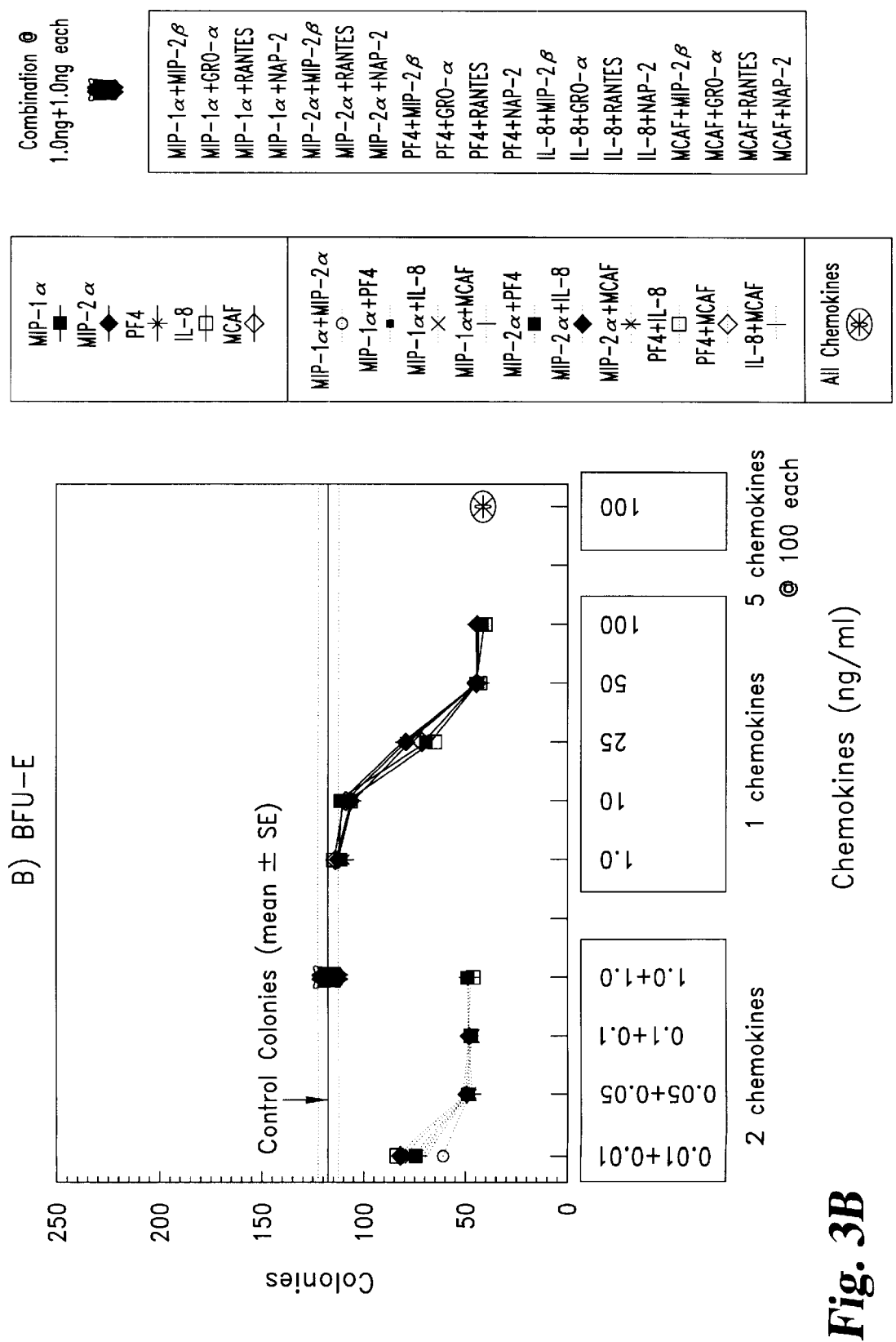
Figure 3C:
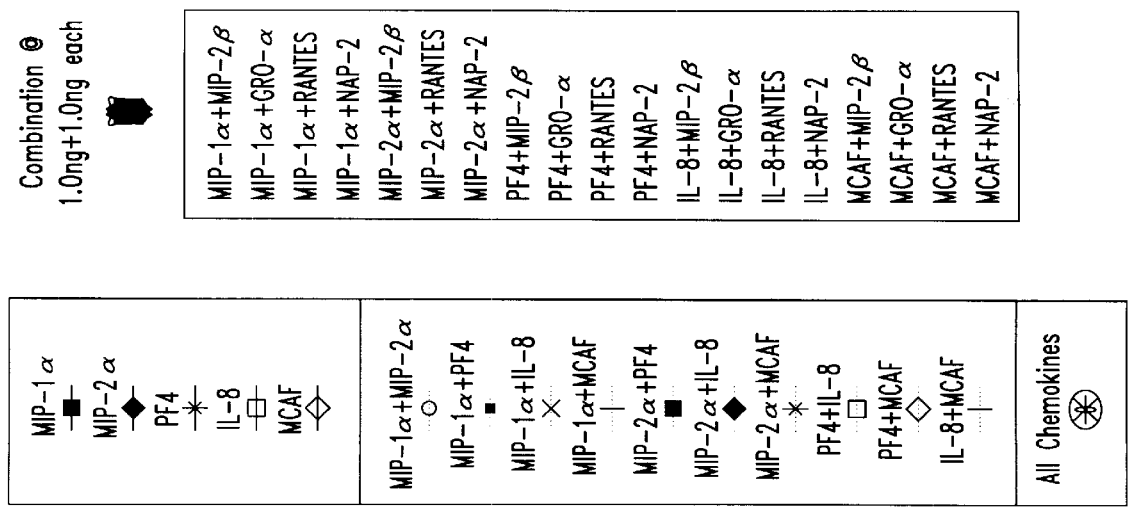
Figure 3C:
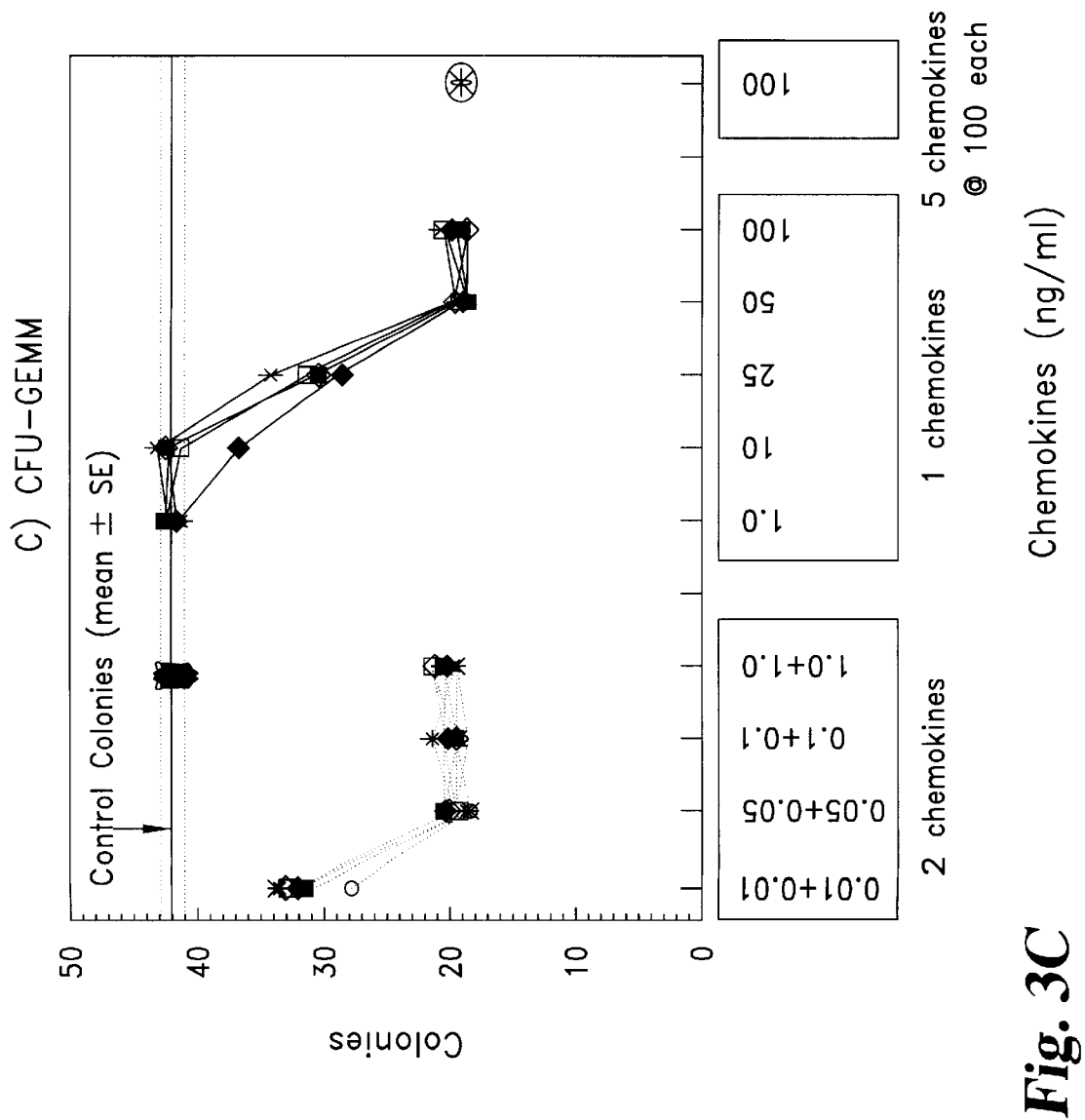

Effects of Combinations of Chemokines at High Concentration: Suppressive Activity In order to determine if greater suppressive activity could be obtained than that noted in FIG. 1, combinations of the chemokines with suppressive activity were first assessed at 100 ng/ml each for effects on colony formation by CFU-GM in LD marrow cells stimulated by rhuGM-CSF (100 U/ml) and rhuSLF (50 ng/ml) (FIG. 3A) and on colony formation by BFU-E (FIG. 3B) and CFU-GEMM (FIG. 3C) in LD marrow cells stimulated by rhuEpo (1 U/ml) and rhuSLF (50 ng/ml). The chemokines were added to the plates prior to adding the cells. As shown, the addition of 100 ng/ml each of MIP-1α, MIP-2α, PF4, IL-8 and MCAF had no greater suppressive effect than that of any one of these chemokines alone. Not shown are data that combinations of two, three or four of these chemokines at 100 ng/ml each also had no greater suppressive effect than that of one of these chemokines.

Effects of Combinations of Chemokines at Low Concentrations: Suppressive Activity The effects on colony formation of low concentrations of combinations of two of each of the ctyokines MIP-1α, MIP-2α, PF4, IL-8 and MCAF were assessed. In a first set of experiments in which the dose response of each cytokine alone was equal to that noted in Table 1, and no suppressive activity was seen at either 10 or 1 ng/ml of each chemokine, the combination of any two of the five suppressive cytokines at 0.1 ng/ml plus 0.1 ng/ml resulted in significant maximal suppression (p<0.001) of colony formation by CFU-GM, BFU-E and CFU-GEMM. In a second set of such experiments shown in FIGS. 3A–C, in which the effects of combinations of cytokines were titrated to lower concentrations, it is apparent that the combination of any two of the five suppressive cytokines, on a weight to weight basis, results in significant suppression with up to 2500 fold less protein than when any of these five cytokines is used alone.

TABLE 1

Dose-Dependent Effects of Supressive Chemokines on Colony Formation by CFU-GM, BFU-E and CFU-GEMM[a]

| Chemokine | Concentration (ng/ml) | % Inhibition of Colony Formation by: | | |
|---|---|---|---|---|
| | | CFU-GM | BFU-E | CFU-GEMM |
| MIP-1α | 100 | 51 ± 2* | 53 ± 2* | 52 ± 3* |
| MIP-1α | 50 | 51 ± 3* | 54 ± 2* | 58 ± 2* |
| MIP-1α | 25 | 23 ± 3** | 27 ± 4** | 30 ± 3** |
| MIP-1α | 10 | 3 ± 2 | 3 ± 3 | 3 ± 2 |
| MIP-1α | 1 | 2 ± 2 | 2 ± 2 | −1 ± 4 |
| MIP-2α | 100 | 50 ± 4* | 50 ± 4* | 55 ± 5* |
| MIP-2α | 50 | 52 ± 4* | 51 ± 5* | 53 ± 3* |
| MIP-2α | 25 | 24 ± 3** | 19 ± 6** | 23 ± 5** |
| MIP-2α | 10 | 3 ± 3 | 4 ± 4 | 6 ± 3 |
| MIP-2α | 1 | 2 ± 2 | 4 ± 2 | −1 ± 6 |
| PF4 | 100 | 52 ± 3* | 50 ± 4* | 53 ± 4* |
| PF4 | 50 | 52 ± 2* | 50 ± 4* | 57 ± 4* |
| PF4 | 25 | 32 ± 5** | 31 ± 2* | 35 ± 9** |
| PF4 | 10 | 10 ± 1 | 10 ± 9 | 13 ± 7 |
| PF4 | 1 | 2 ± 3 | 5 ± 2 | 7 ± 4 |
| IL-8 | 100 | 52 ± 4* | 52 ± 3* | 55 ± 4* |
| IL-8 | 50 | 46 ± 4* | 50 ± 7* | 52 ± 5* |
| IL-8 | 25 | 26 ± 7** | 39 ± 6** | 33 ± 8** |
| IL-8 | 10 | 6 ± 6 | 8 ± 6 | 4 ± 4 |
| IL-8 | 1 | −1 ± 2 | 3 ± 3 | 2 ± 2 |
| MCAF | 100 | 51 ± 1* | 49 ± 4* | 55 ± 5* |
| MCAF | 50 | 47 ± 3* | 50 ± 4* | 53 ± 3* |
| MGAF | 25 | 25 ± 6** | 22 ± 3** | 28 ± 2** |
| MCAF | 0 | 8 ± 4 | 4 ± 2 | ± 6 |
| MCAF | 1 | 0 ± 4 | 1 ± 2 | 0 ± 2 |

[a]The results shown are the average of assays on four separate marrows. Control colony numbers for CFU-GM plated in the presence of GM-CSF plus SLF, and for BFU-E and CFU-GEMM plated in the presence of Epo plus SLF were respectively 121 ± 2, 212 ± 3, 143 ± 2 and 197 ± 3 for CFU-GM, 122 ± 5, 118 ± 6, 115 ± 4, and 56 ± 5 for BFU-E, and 36 ± 2, 42 ± 1, 33 ± 2 and 58 ± 4 for CFU-GEMM per $10^5$ low density marrow cells/ml/plate.
*designates significant decrease, p < 0.001 compared to control values;
**designates significant decrease p < 0.01 compared to control values;
other values were not significantly different from control, p > 0.05.

An assessment was also made whether such synergistic suppression was possible if a low concentration (1.0 ng/ml) of MIP-1α, MIP-2α, PF4, IL-8, or MCAF was added with 1.0 ng/ml of the following chemokines which at high concentrations (up to 1000 ng/ml) had no suppressive activity on their own: MIP-2β, GRO-α, Rantes and NAP-2. From the results shown in FIGS. 3A–C, it is apparent that the combination of low concentrations of the chemokines that do not have suppressive activity at higher concentrations with concentrations of MIP-1α, MIP-2α, PF4, IL-8 and MCAF that each alone do not have suppressive activity, does not result in suppressive activity. Thus, only the chemokines that have suppressive activity alone can act together at low concentrations to synergistically suppress the growth of myeloid progenitor cells. From the results in Table 2, it is also apparent that low concentrations of each of two of the five suppressive chemokines can synergize to suppress colony formation of CFU-GM, BFU-E and CFU-GEMM in a population of CD34+++ sorted marrow cells in which ±88% of the cells are progenitors. These results evidence that the synergistic suppression noted is mediated directly on the progenitors themselves rather than via an action on accessory cells.

Analogous tests were performed in which IP-10 was used at low concentrations in combination with MIP-1α, MIP-2α, PF4, IL-8, or MCAF. The results are given in FIG. 16, and demonstrate that IP-10 also shows synergistic suppressive activity when combined with other suppressive chemokines. The surprising ability of these suppressive chemokine cytokines to synergize with other suppressive cytokines is a feature of the present invention and can be incorporated into a broad range of advantageous compositions and methods related to the suppression of myeloid cells.

TABLE 2

Influence of Chemokines, Alone and in Combination, on Colony Formation by Myeloid Progenitor Cells in Sorted CD34+++ Human Bone Marrow Cells.*

| Chemokine(s) (concentration; ng/ml) | CFU-GM | BFU-E | CFU-GEMM |
|---|---|---|---|
| Control Medium | 176 ± 3 | 30 ± 1 | 15.3 ± 1.8 |
| MIP-1α (50) | 56 ± 5[a] | 5 ± 2[a] | 0.7 ± 0.7[a] |
| MIP-1α (25) | 65 ± 9[a] | 15 ± 2[a] | 2.7 ± 0.7[a] |
| MIP-1α (10) | 85 ± 2[a] | 15 ± 2[b] | 6.7 ± 0.7[c] |
| MIP-1α (1) | 153 ± 10 | 23 ± 3 | 12.0 ± 1.2 |
| MIP-2α (50) | 97 ± 7[a] | 12 ± 1[a] | 4.7 ± 1.3[c] |
| MIP-2α (25) | 112 ± 8[a] | 15 ± 1[a] | 7.3 ± 1.3[d] |
| MIP-2α (10) | 140 ± 7[c] | 18 ± 1[b] | 9.0 ± 1.7 |
| MIP-2α (1) | 170 ± 5 | 27 ± 2 | 13.3 ± 0.7 |
| PF4 (50) | 110 ± 1[a] | 14 ± 2[a] | 6.7 ± 1.3[d] |
| PF4 (25) | 125 ± 7[b] | 18 ± 1[a] | 8.7 ± 1.3 |
| PF4 (10) | 147 ± 2[c] | 22 ± 3[d] | 10.7 ± 1.3 |
| PF4 (1) | 167 ± 6 | 26 ± 1 | 12.7 ± 1.8 |
| IL-8 (50) | 98 ± 6[a] | 14 ± 1[a] | 5.3 ± 0.7[c] |
| IL-8 (25) | 116 ± 1[a] | 17 ± 2[a] | 8.0 ± 1.2[d] |
| IL-8 (10) | 139 ± 3[a] | 21 ± 2[c] | 10.7 ± 2.9 |
| IL-8 (1) | 156 ± 13 | 27 ± 3 | 12.0 ± 2.3 |
| MCAF (50) | 58 ± 5[a] | 10 ± 2[a] | 0[a] |
| MCAF (25) | 67 ± 3[a] | 19 ± 3[a] | 0.7 ± 0.7[a] |
| MCAF (10) | 82 ± 5[a] | 18 ± 1[a] | 5.3 ± 1.8[d] |
| MCAF (1) | 127 ± 7[c] | 23 ± 2 | 8.7 ± 1.3 |
| MIP-1α (1) + MIP-2α (1) | 34 ± 2[a] | 5 ± 1[a] | 0[a] |
| MIP-1α (0.1) + MIP-2α (0.1) | 63 ± 7[a] | 9 ± 1[a] | 4.7 ± 0.7[b] |
| MIP-1α (1) + PF4 (1) | 37 ± 1[a] | 9 ± 2[a] | 0.7 ± 0.7[a] |
| MIP-1α (0.1) + PF4 (0.1) | 59 ± 5[a] | 10 ± 3[a] | 1.7 ± 1.7[a] |
| MIP-1α (1) + IL-8 (1) | 27 ± 6[a] | 5 ± 1[a] | 0.7 ± 0.7[a] |
| MIP-1α (0.1) + IL-8 (0.1) | 47 ± 3[a] | 13 ± 2[a] | 2.0 ± 1.1[a] |
| MIP-1α (1) + MCAF (1) | 31 ± 4[a] | 13 ± 3[a] | 2.0 ± 1.2[a] |
| MIP-1α (0.1) + MCAF (0.1) | 85 ± 2[a] | 17 ± 2[a] | 6.7 ± 0.7[c] |
| MIP-2α (1) + PF4 (1) | 26 ± 3[a] | 11 ± 2[a] | 0[a] |
| MIP-2α (0.1) + PF4 (0.1) | 34 ± 3[a] | 19 ± 4[a] | 3.3 ± 1.3[c] |
| MIP-2α (1) + IL-8 (1) | 56 ± 4[a] | 22 ± 2[d] | 8.7 ± 2.4 |
| MIP-2α (0.1) + IL-8 (0.1) | 97 ± 5[a] | 25 ± 2 | 10.7 ± 2.9 |
| MIP-2α (1) + MCAF (1) | 48 ± 5[a] | 13 ± 2[a] | 6.7 ± 1.8[d] |
| MIP-2α (0.1) + MCAF (0.1) | 90 ± 2[b] | 21 ± 1[b] | 8.7 ± 1.3[e] |
| PF4 (1) + IL-8 (1) | 45 ± 3[a] | 15 ± 1[a] | 0[a] |
| PF4 (0.1) + IL-8 (0.1) | 67 ± 5[a] | 17 ± 1[a] | 7.3 ± 0.7[c] |
| PF4 (1) + MCAF (1) | 35 ± 3[a] | 15 ± 3[a] | 3.3 ± 0.7[b] |
| PF4 (0.1) + MCAF (0.1) | 58 ± 6[a] | 20 ± 1[b] | 9.3 ± 0.7[d] |
| IL-8 (1) + MCAF (1) | 39 ± 4[a] | 13 ± 2[a] | 2.7 ± 0.7[b] |
| IL-8 (0.1) + MCAF (0.1) | 76 ± 5[a] | 22 ± 2[c] | 6.7 ± 0.7[c] |

*250 NALDT ™ CD34+++ human bone marrow cells plated in the presence of Epo (1 U/ml), SLF (50 ng/ml) and rhuIL-3 (200 U/ml), and in the absence and presence of chemokines were scored for CFU-GM colonies (≧40 cells/group) plus clusters (<40 cells/group), and BFU-E and CFU-GEMM colonies after 14 days of incubation. The cloning efficiency for growth in the absence of chemokines for this experiment in which all colonies were scored from the same plates was 88.4% (176 ± 3 CFU-GM plus 30 ± 1 BFU-E plus 15.3 ± 1.8 CFU-GEMM for 250 cells plated).
[a]Significant difference from control medium, p < 0.001;
[b]p < 0.005;
[c]p < 0.01;
[d]p < 0.03;
[e]p < 0.05.

Effects of Combinations of Chemokines: Blocking Activity

Figure 4:
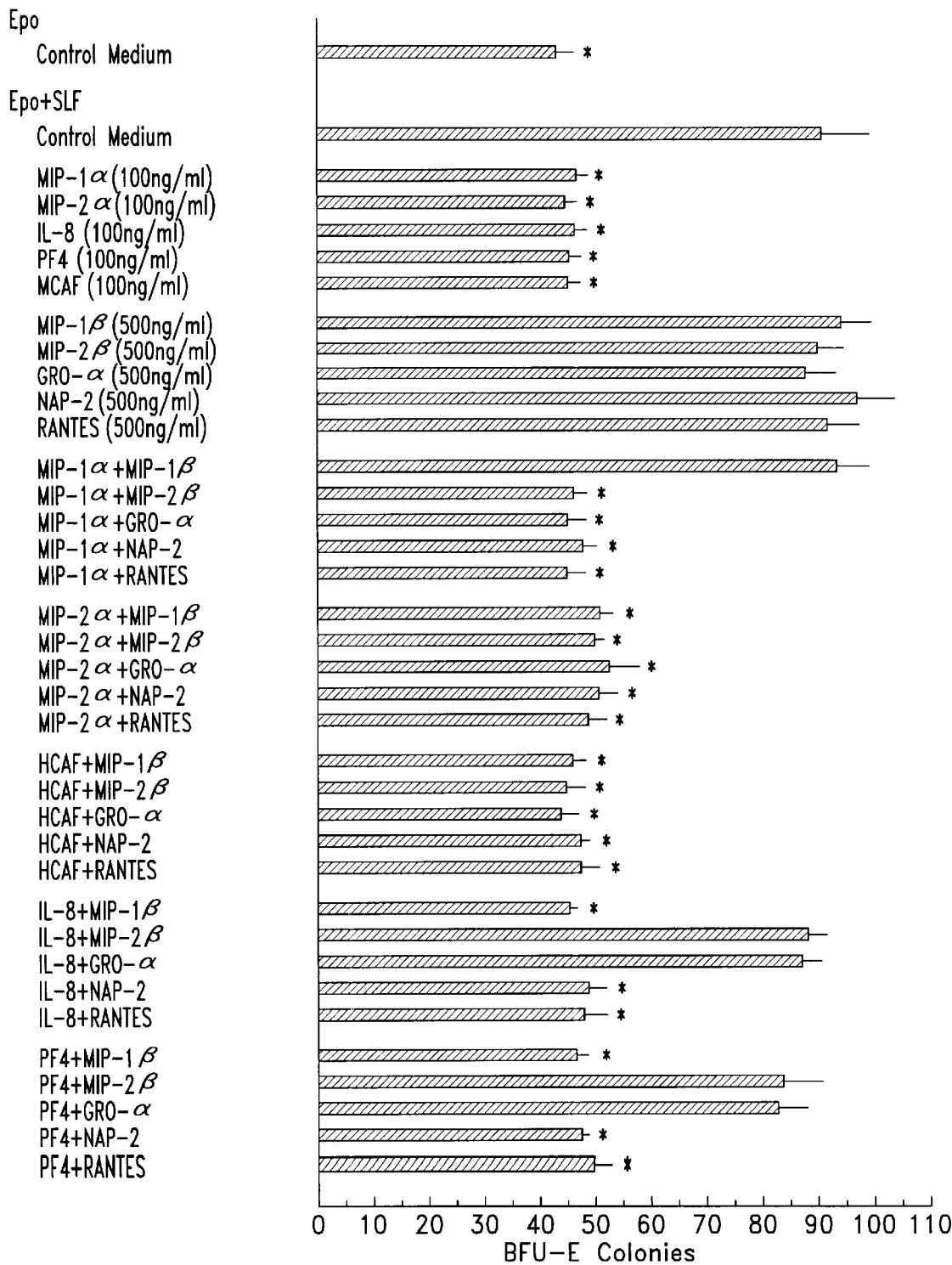
FIG. 4: Influence of combinations of suppressive and non-suppressive chemokines on colony formation by BFU-E present in $10^5$ low density normal human bone marrow cells/ml. Chemokines were added to plates prior to adding cells. "*" designates significant decrease (p<0.001) compared to cells grown in the presence of Epo plus SLF; other values not significantly different from control of Epo plus SLF.

An assessment was made of the effects on colony formation of 5-fold excess amounts of the hu cytokines that did not demonstrate suppressive activities (500 ng/ml of either MIP-1β, MIP-2β, GRO-α, NAP-2 and RANTES) when added with cytokines with suppressive activity (100 ng/ml of either MIP-1α, MIP-2α, PF4, IL-8 and MCAF) (FIG. 4, one of 2 reproducible experiments using BFU-E-colony formation as the test assay). The chemokines were added together in the plates prior to addition of the cells. MIP-1β blocked the suppressive effects of MIP-1α. MIP-2β and GRO-α blocked the suppressive effects of IL-8 and PF4. At least at the ratios of chemokines assessed (5:1), MIP-1β did not block the suppressive effects of MIP-2α, IL-8, PF4 of MCAF; MIP-2β and GRO-α did not block the suppressive effects of MIP-1α, MIP-2α, or MCAF. NAP-2 or RANTES did not block the suppressive effects of MIP-1α, MIP-2α, IL-8, PF4 or MCAF. Similar effects were also noted in two experiments each using colony formation of CFU-GM or CFU-GEMM as a test assay.

Figure 5:
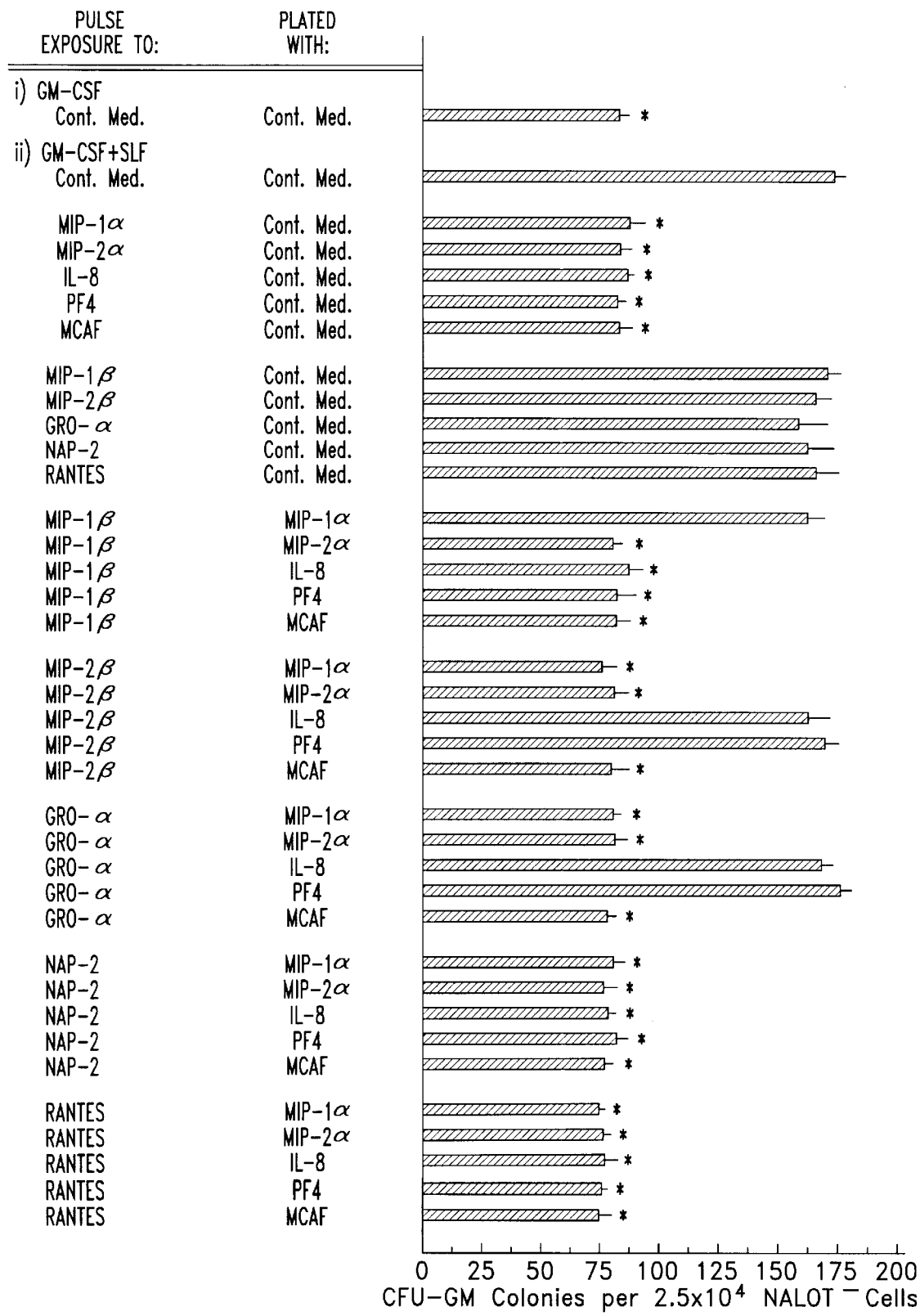
FIG. 5: Influence of pulse exposure of NALDT⁻ normal human bone marrow cells to chemokines on effects of subsequent exposure of these cells to other chemokines. "*" designates significant decrease, p<0.01, compared to cells grown in the presence of GM-CSF plus SLF; other values not significantly different from control of GM-CSF plus SLF.

Also assessed were the effects on colony formation of pulse exposure of NALDT⁻ bone marrow cells to the various hu chemokines in terms of the suppressive and blocking activities of these molecules. As shown in FIG. 5 (one of two reproducible experiments using colony formation of CFU-GM as the test assay system), pulse exposure of cells to MIP-1α, MIP-2α, IL-8, PF4 and MCAF for 1 hour at 4° C. with 100 ng chemokine/$10^5$ cells prior to washing cells 2× and plating in the presence of GM-CSF (100 U/ml) and SLF (50 ng/ml) resulted in about 50% inhibition of total colony formation and in complete suppression of the SLF-enhanced colony formation. Not shown in this figure is that after cells had been pulsed with either MIP-1α, MIP-2α, IL-8, PF4 or MCAF, colony numbers were not further changed by the subsequent addition to the plates of 100 ng/ml MIP-1α, MIP-2α, IL-8, PF4 or MCAF or 500 ng/ml of MIP-1β, MIP-2β, GRO-α, NAP-2, or RANTES. Pulse exposure of cells to MIP-1β, MIP-2β, GRO-α, NAP-2, or RANTES, at 500 ng/$10^5$ cells, had no significant effect (p>0.05) on cells stimulated with GM-CSF and SLF (FIG. 5). However, pulse exposure of cells to MIP-1β blocked the suppressive effect of subsequently added MIP-1α to the plates, and pulse exposure of cells to MIP-2β or GRO-α each blocked the suppressive effects of subsequently added IL-8 or PF4 to the plates. Similar results were seen in two experiments in which colony formation by BFU-E or CFU-GEMM served as the test assay system. The results of the pulsing experiments (FIG. 5) thus reproduce the effects seen when combinations of chemokines were added directly to the plates without pulsing of the cells (FIG. 4). These effects are consistent with receptor-mediated events.

Effects of Monomeric vs. Polymerized Chemokines: Suppressive Activity

Figure 6:
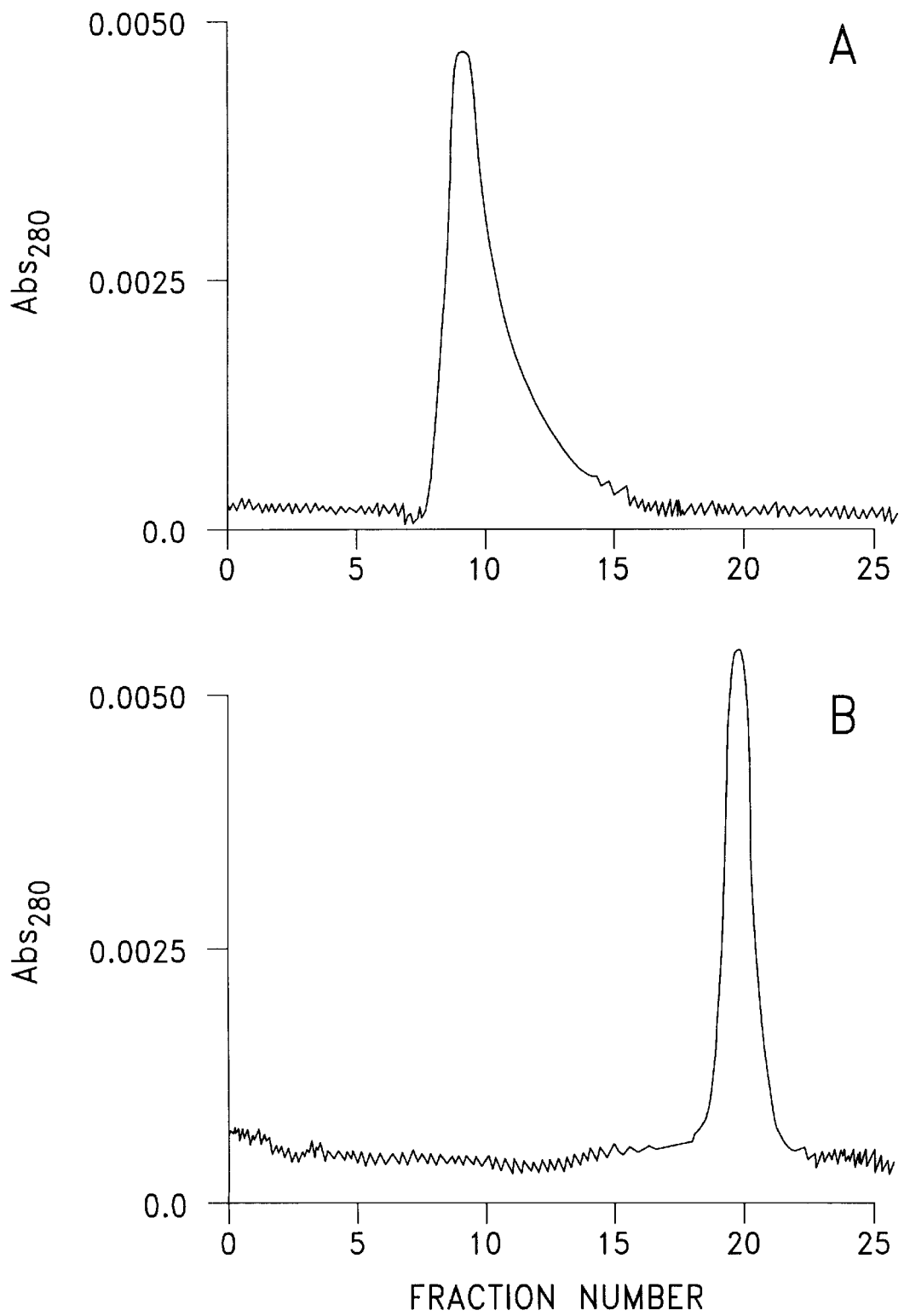
FIGS. 6A, 6B and 6C: Gel filtration chromatography and quantitation of MIP-1α. Shown are representative elution profiles of rmuMIP-1α from a stock solution of ACN.
Figure 6:
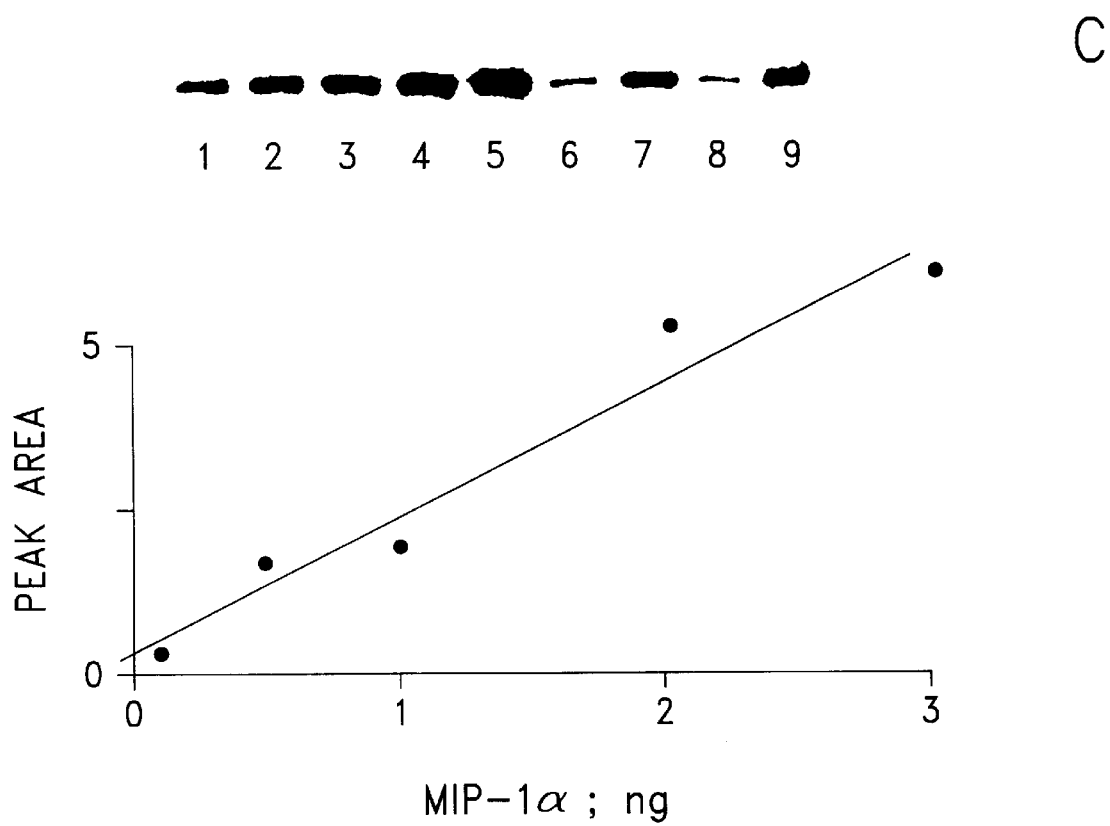

The suppressive effects of monomeric versus polymerized forms of chemokine were assessed. RhuMIP-1α was purchased from R&D Systems (Minneapolis, Minn.) in 30% acetonitrile and 0.1% trifluoroacetitc acid (ACN) without protein carriers. After gel filtration chromatography on a Superose-12 column in this buffer, rmuMIP-1α was in monomeric form with an approximate molecular weight of 8 KD (FIG. 6B). However, when MIP-1α, in ACN, was diluted 1:20 with phosphate buffered saline (PBS) to a final concentration of greater than 20 ng/ml and assessed by gel filtration chromatography in PBS, >99.7% of the recovered protein eluted in polymerized form of about 650 KD (FIG. 6A). Treatment with 1M NaCl did not dissociate the molecule. However, treatment with 2% sodium dodecyl sulphate (SDS) at 100° C. for 20 min. in the presence of 5% 2-mercaptoethanol completely dissociated the molecule into 8 KD monomeric form (FIG. 6C). A standard curve for the SDS-dissociated MIP-1α as assessed by immunoblotting with rabbit anti rmuMIP-1α is shown in FIG. 6C. Because of the polymerized nature of MIP-1α in PBS, immunoblotting of SDS-polyacrylamide gel electrophoresis (PAGE)-separated MIP-1α probably allows a more accurate estimate of its actual concentration than obtainable by ELISA or radioimmunoassay assay.

Figure 7:
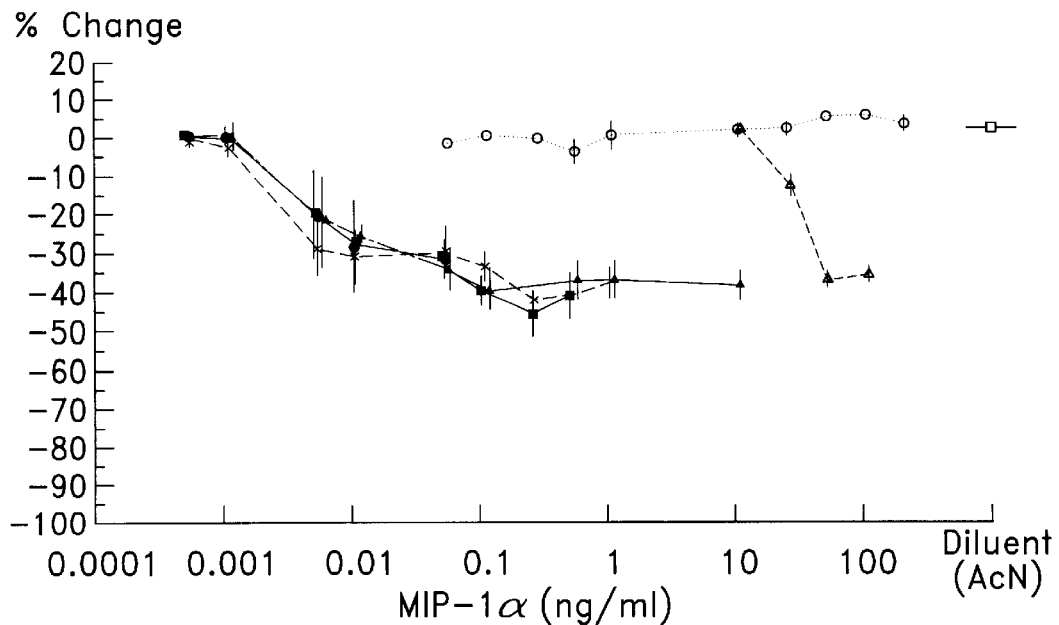
FIG. 7: Influence of purified monomeric and purified polymerized rmuMIP-1α on proliferation of mouse marrow CFU-GM. The axis for MIP-1α concentration is log scale. MIP-1α preparations were assayed for effects on colony formation by $7.5\times10^4$ bone marrow cells per ml from $BDF_1$ mice (Jackson Laboratories, Bar Harbot, MEO plated in 0.3% agar-culture medium in the presence of 100 U/ml rmuGM-CSF and 50 ng/ml rmuSLF Immunex Corp. Seattle Wash.). Colonies (>40 cells/group) containing neutrophilic granulocytes and/or monocytes, macrophages were sorted (3 plates/determination) after 6–7 days incubation at 5% $CO_2$ in lowered (5%) $O_2$ tension. Results are expressed as man percentage change±1 SEM from control (McCoy's) medium for: MIP-1α from a stock solution an ACN diluted in PBS to a final concentration of >20 ng/ml (... Δ...; 7 experiments), monomeric MIP-1α from a stock solution in ACN diluted in PBS to a final concentration of >20 ng/ml which was separated by gel filtration (FIG. 1A) (---*---; 4–8 experiments; including 2 experiments in which monomeric MIP-α from the column was left in PBS collection medium (<5 ng/ml) at 4° C. for up to 3 weeks), polymerized MIP-1αwhich formed in PBS at a final concentration of >20 ng/ml and was separated by gel filtration (FIG. 1A) (... o ...; 3–7 experiments; including 2 experiments in which poly-merized MIP-1α from the column was left in PBS collection medium (>350 ng/ml) at 4° C. for up to 3 weeks), MIP-1α from a stock solution in ACN diluted in PBS to a final concentration of ≦5 ng/ml (____■____); 3–4 experiments), separated MIP-1α polymer placed into ACN solution and incubated overnight prior to dilution in PBS to a final concentration of ≦5 ng/ml (_ _ _ _Δ_ _ _ _; 2–4 experiments), and ACN diluent alone (____□____: 8 experiments with dilutions of ACN found in MIP-preparations assayed for activity). Control numbers of colonies for the 8 experiments ranged from 67±3 to 137±12.
Figure 9:
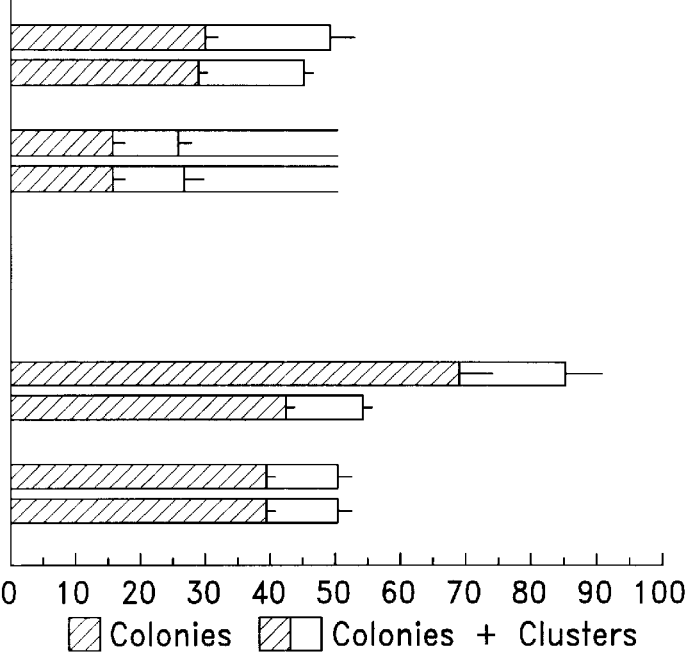
FIGS. 9A and 9B: Influence of CFU-GM cell cycle on responsiveness of cells to inhibition by rmuMIP-1α.
Figure 9:
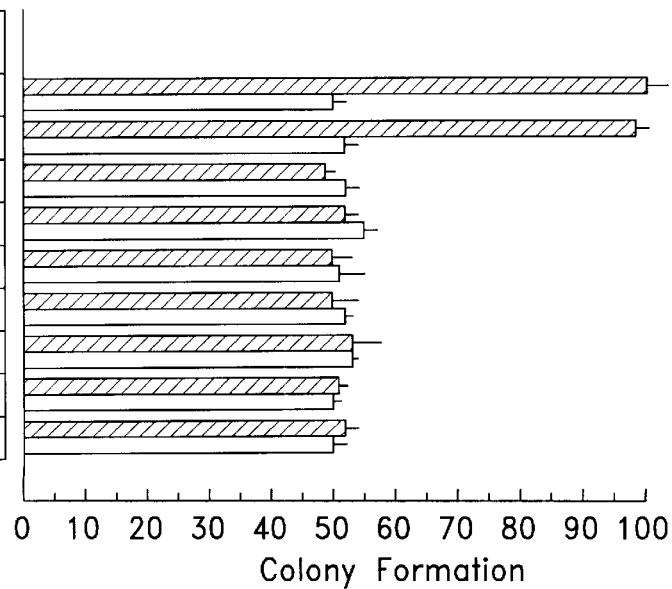
Figures 10A, 10B:
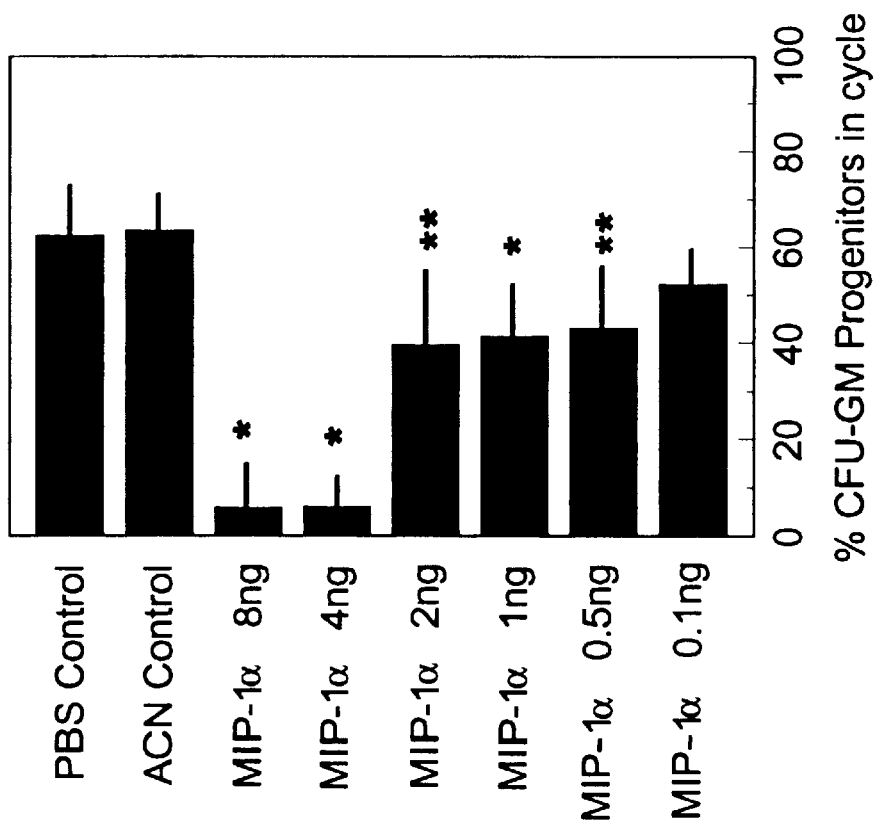
FIG. 10: Influence of varying dosages of monomeric rmuMIP-1α on percentage of CFU-GM in cycle in the bone marrow and spleen of C3H/HeJ mice 24 hrs after a single injection i.v. of MIP-1α. Results are averages of 3 experiments in which a total of 6–9 mice were individually assessed per group. The % CFU-GM in cycle are based on colony number of cells treated with McCoy's medium which ranged from 27 to 58 for bone marrow and 22 to 43 for spleen. Significant % change from diluent control: *p<0.001; p<0.005; *p<0.05.
Figure 11B:
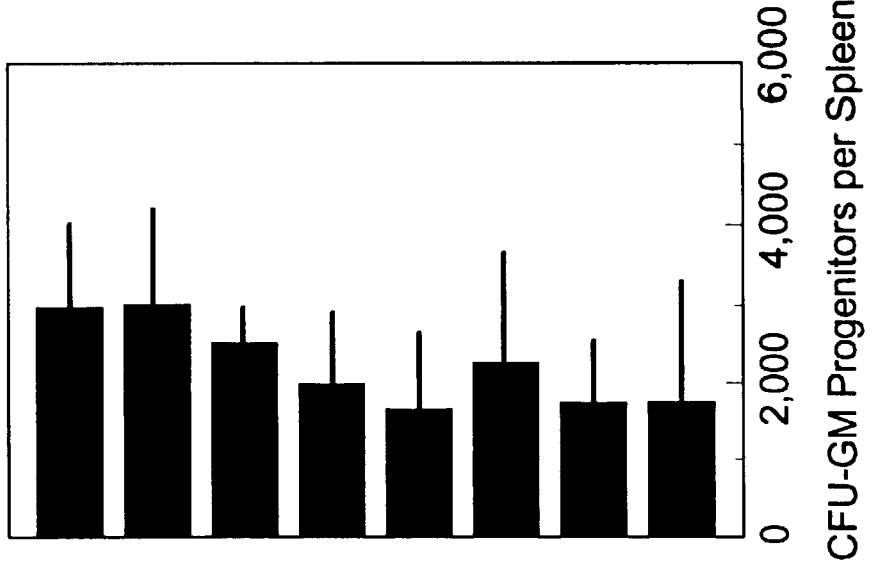
FIG. 11: Influence of varying dosages of momomeric rmuMIP-1α on absolute numbers of CFU-GM in the bone marrow and spleen of C3H/HeJ mice 24 hours after a single injection i.v. of MIP-1α. Significant % change from diluent control: *p<0.001; **p<0.05.
Figure 11A:
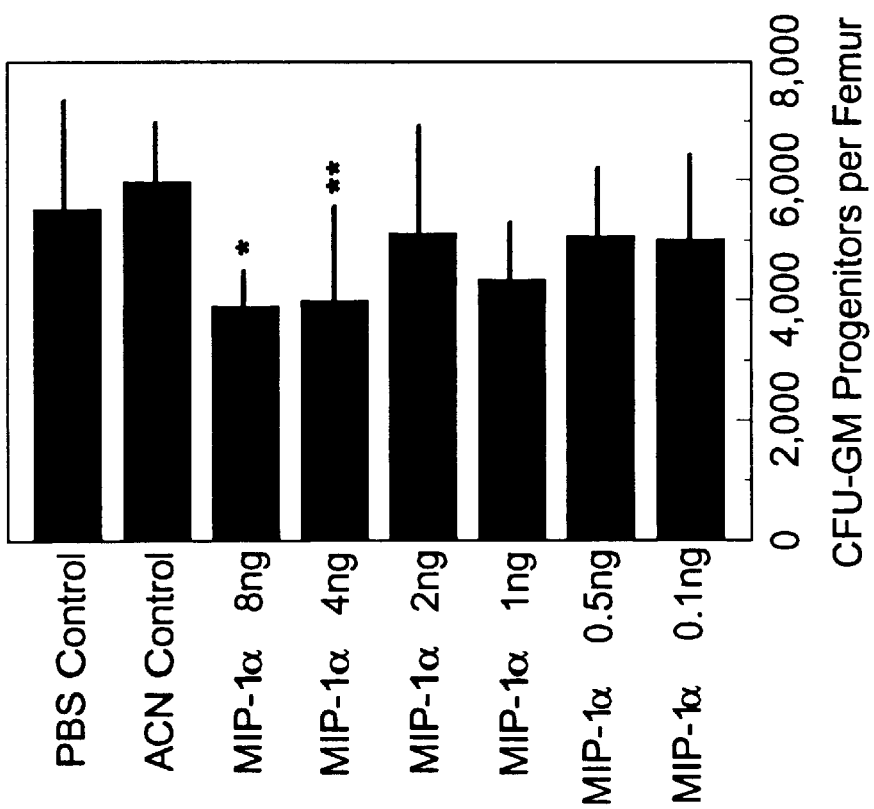
Figure 12A:
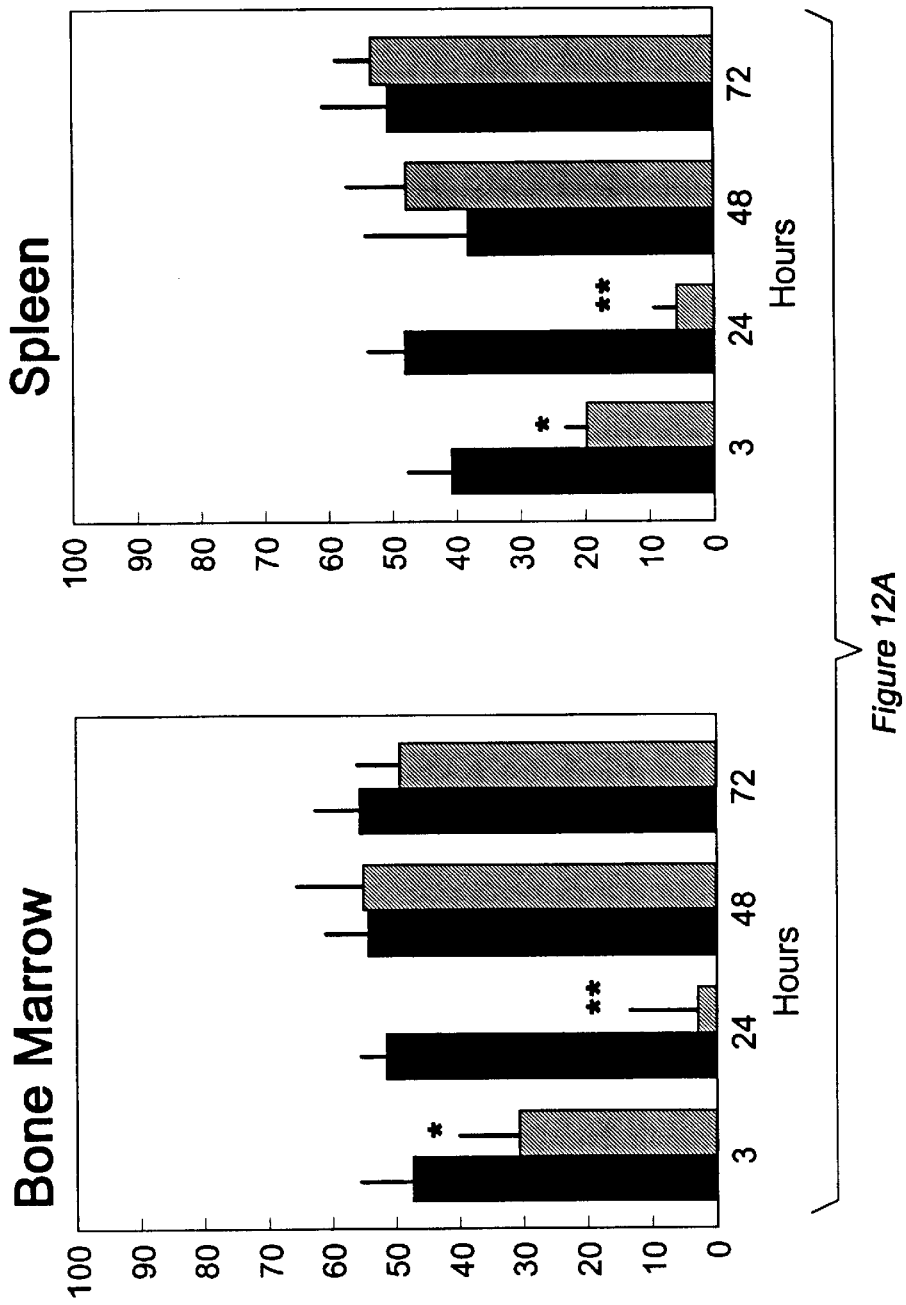
Figure 12B:
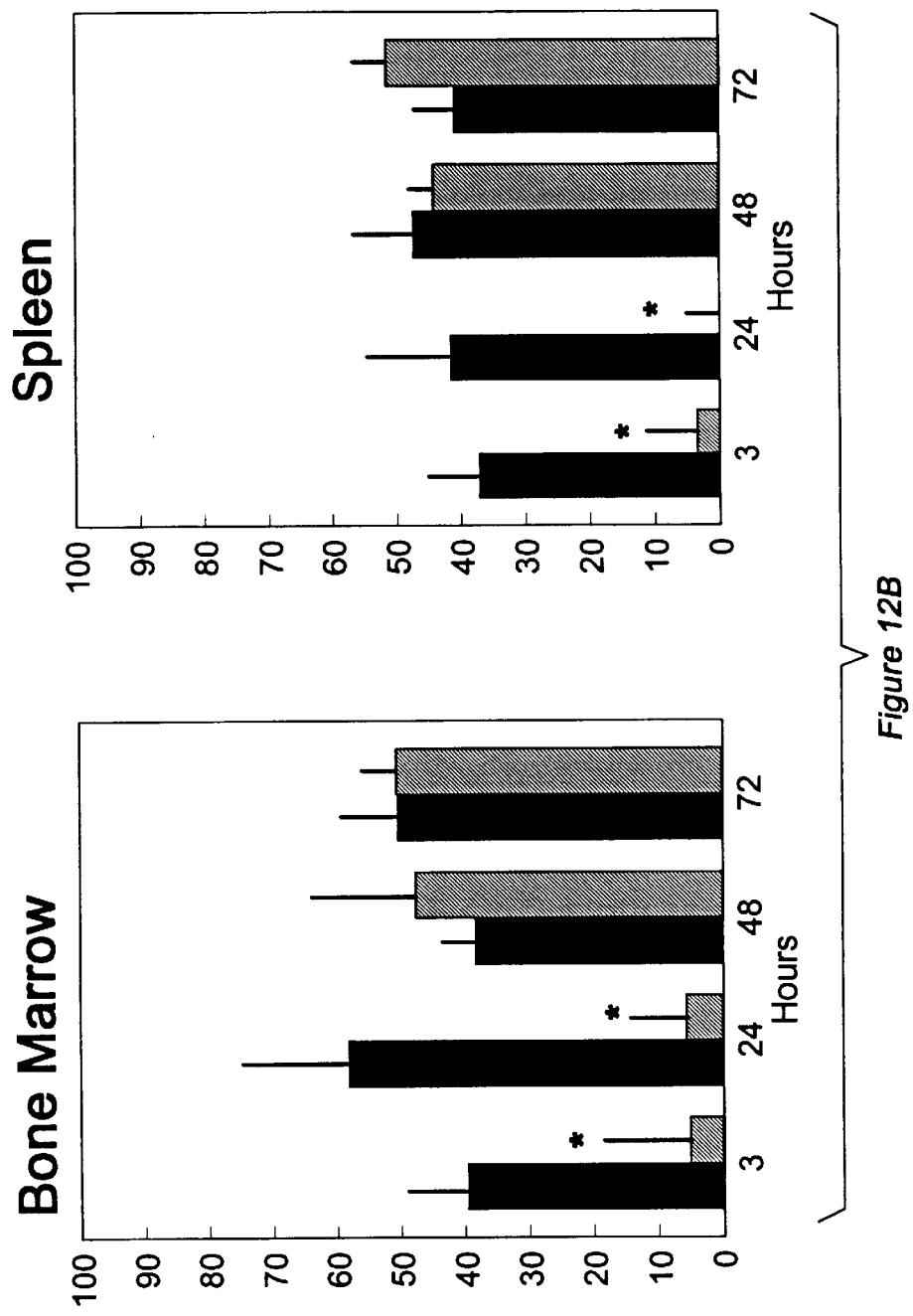
Figure 12C:
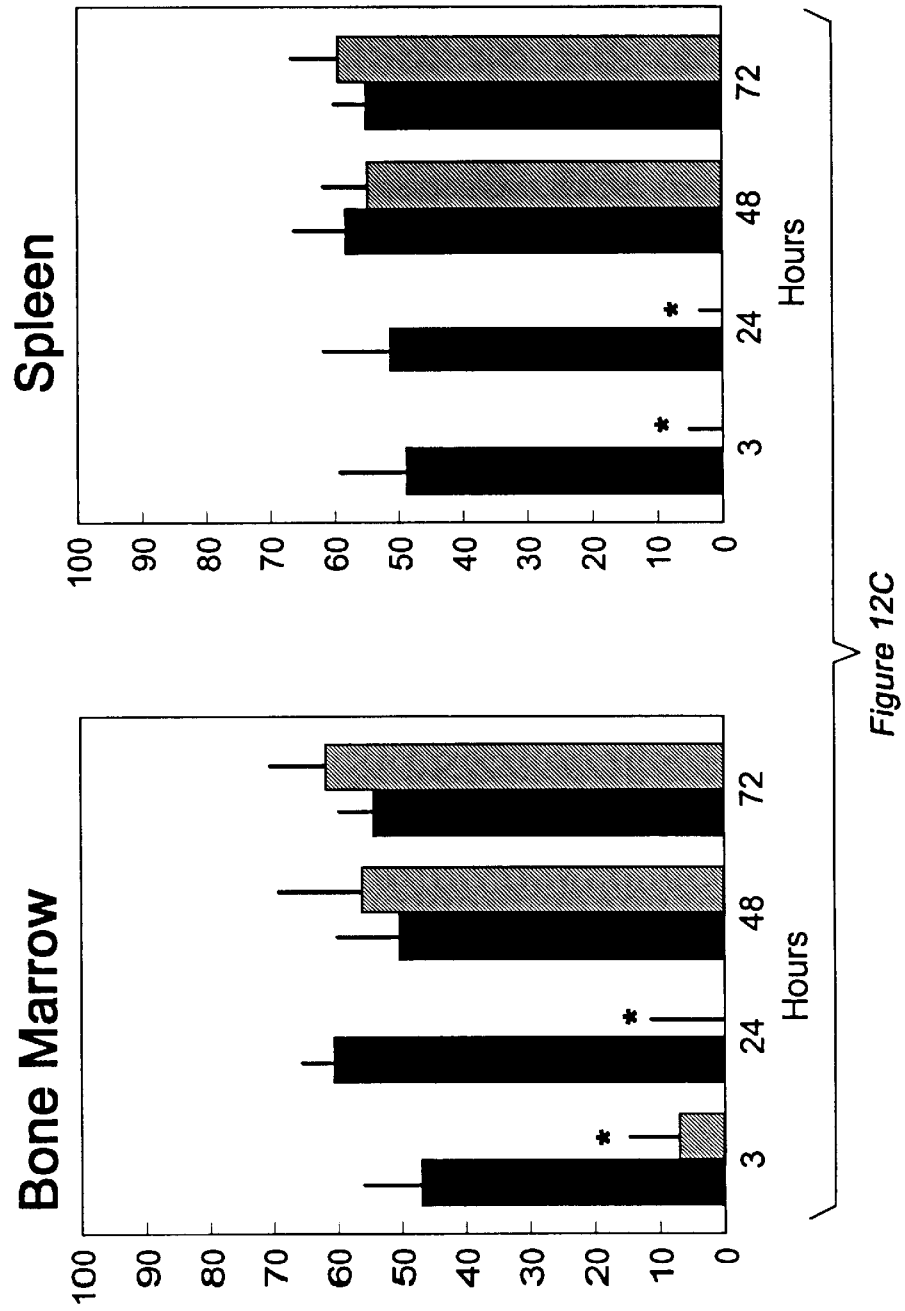
Figure 13A:
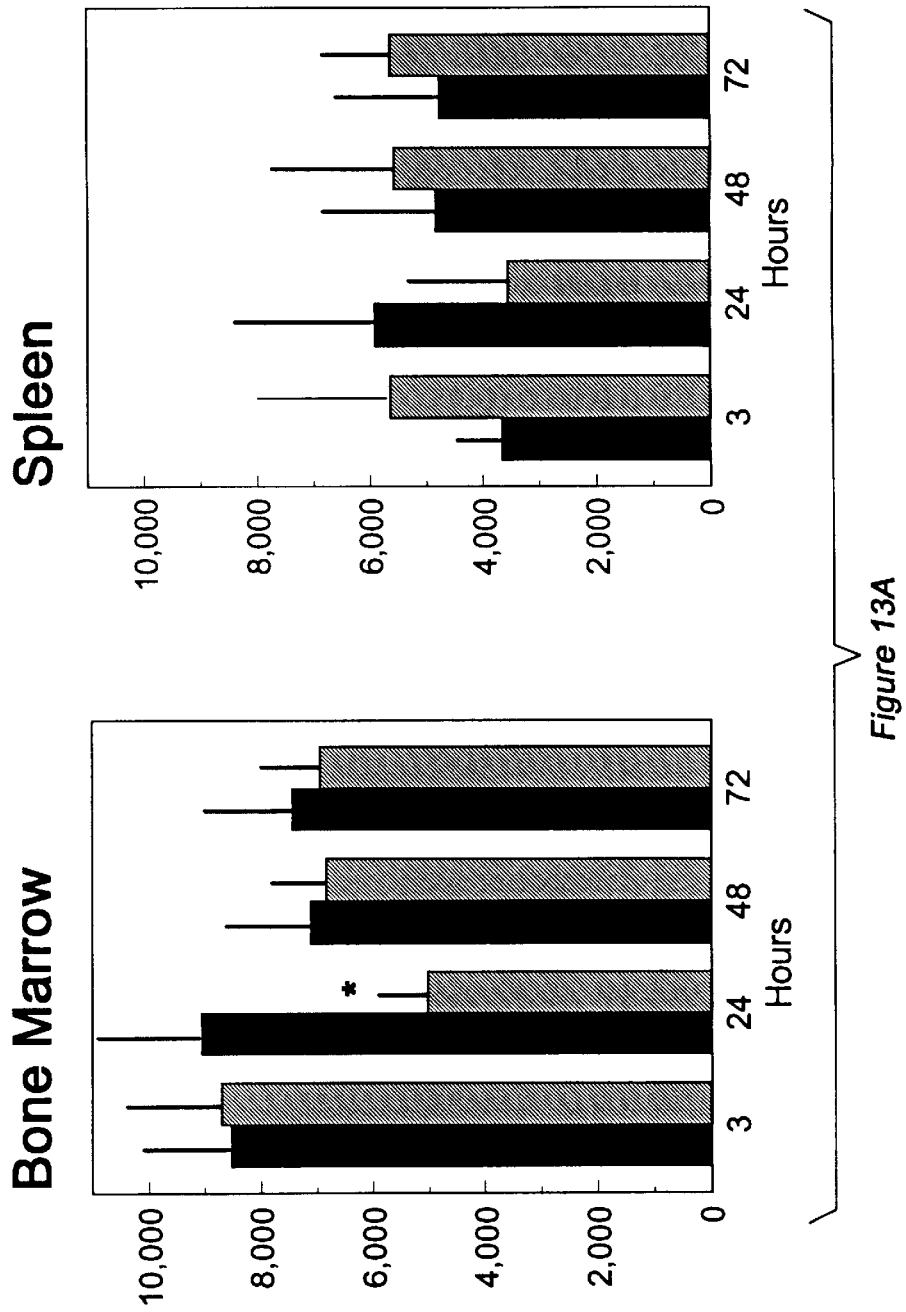
Figure 13B:
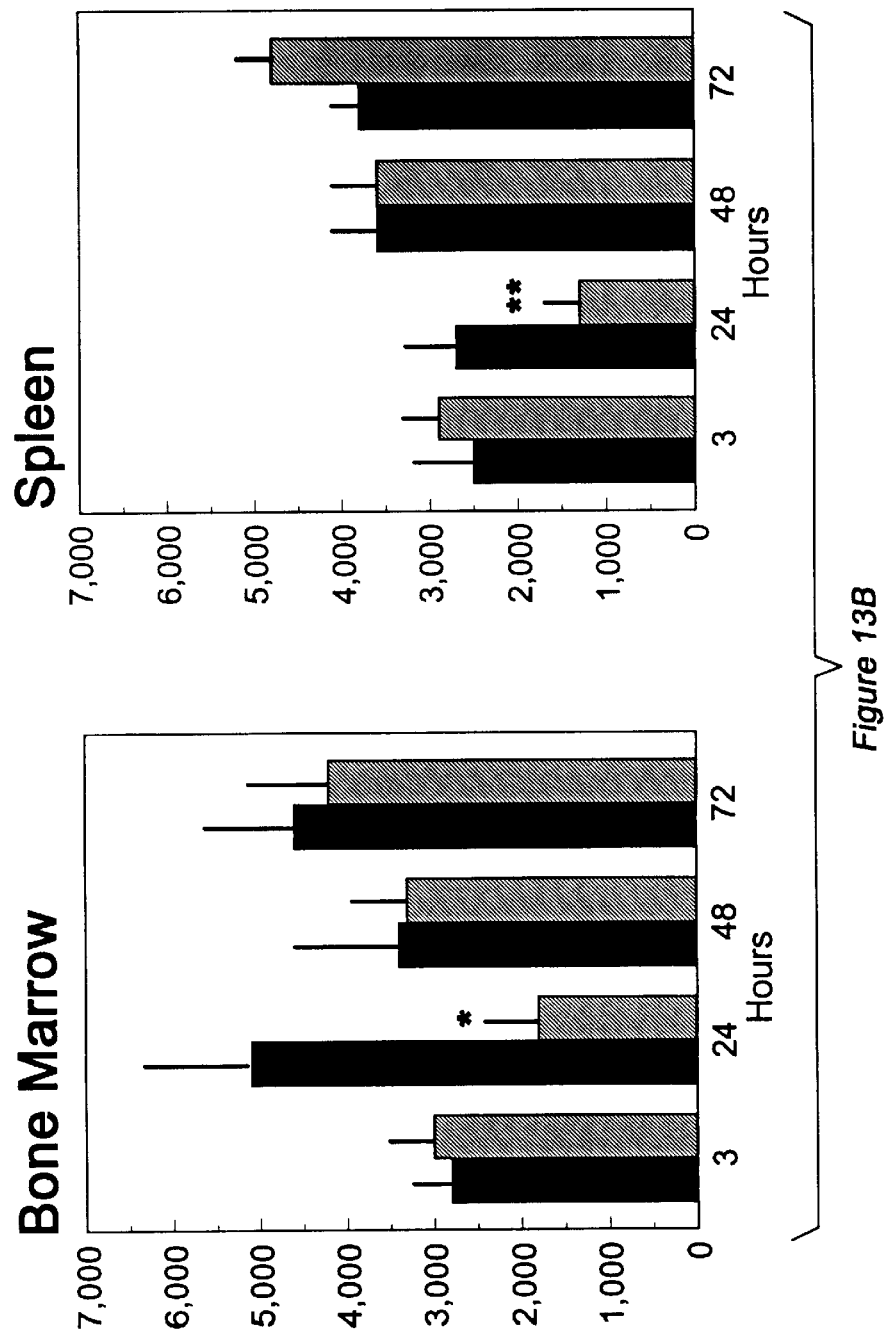
Figure 13C:
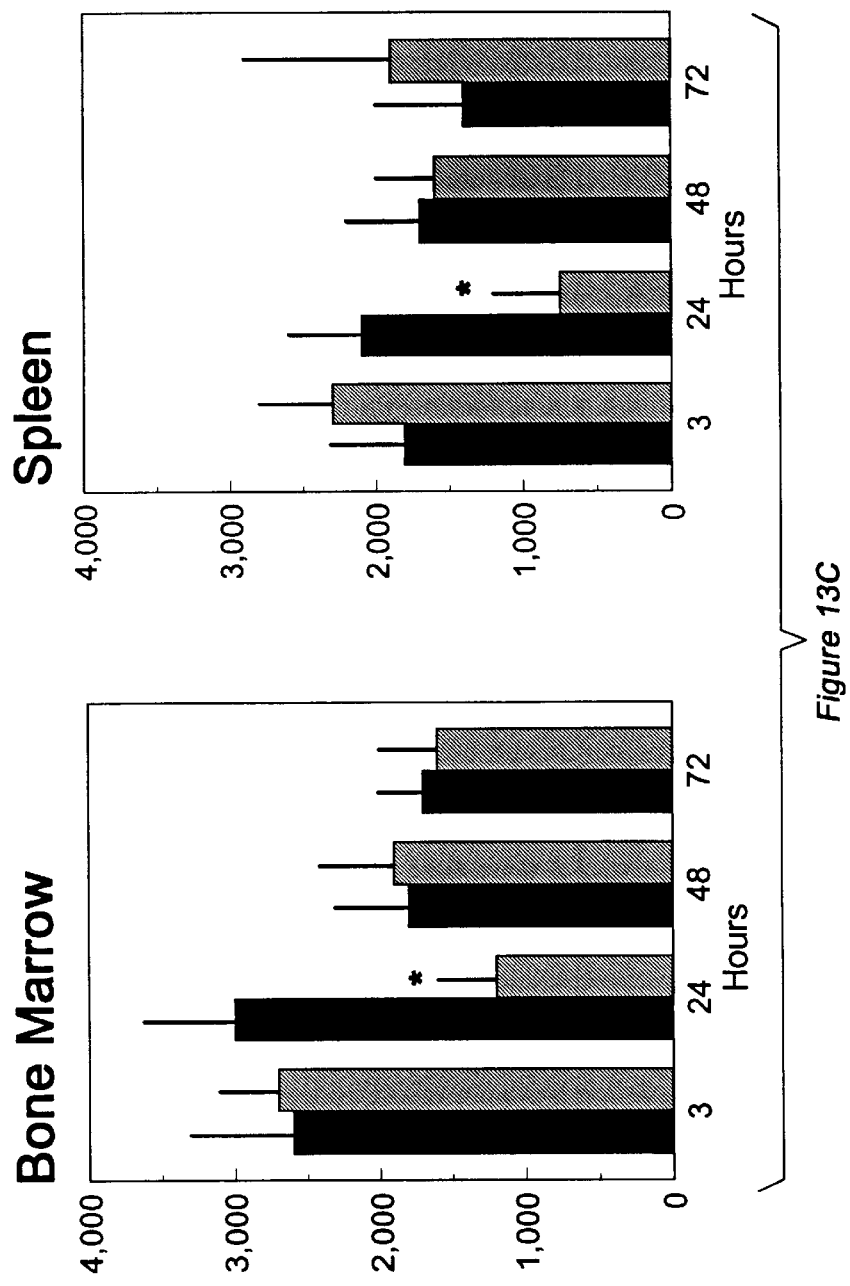
Figure 14A:
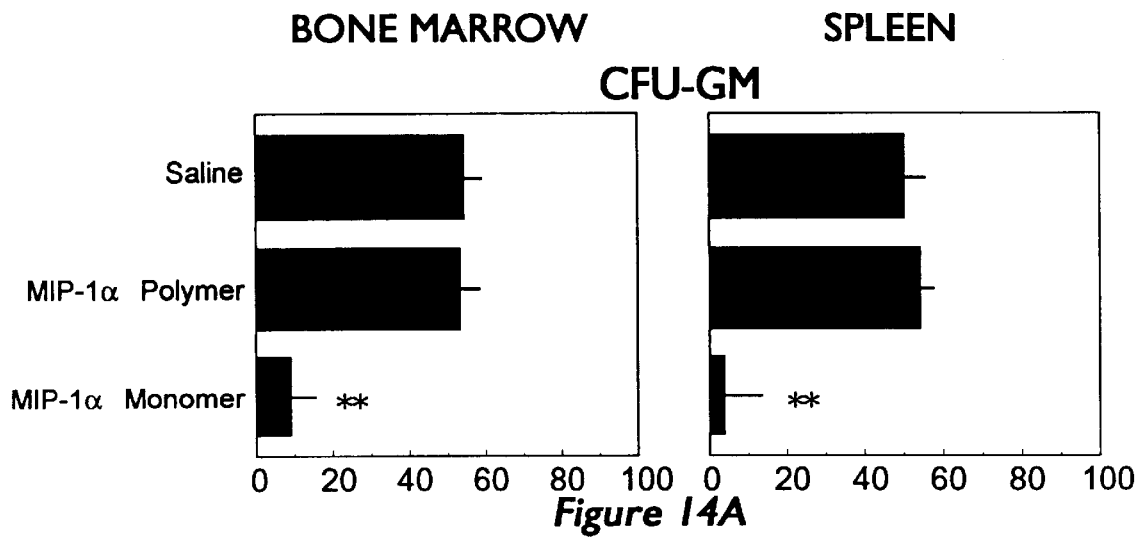
FIG. 14: Comparative influences of monomeric (8 ng) and polymerized (200 ng) rmuMIP-1α on the percentage of myeloid progenitors in cycle in the bone marrow and spleen of C3H/HeJ mice 24 hrs after a single injection i.v. of MIP-1α. Results are averages of 1 experiment in which a total of 5 mice were individually assessed per group. The % progenitors in cycle are based on colony numbers of cells treated with McCoy's medium which ranged from 53–83 for marrow and 74–96 for splenic CFU-GM, from 6–11 for marrow and 7–18 for splenic CFU-GEMM, and from 15–24 for marrow and 32–73 for splenic BFU-E. Significant % change from saline control, **p<0.001; other numbers are not significantly different from control, p>0.05.
Figure 14B:
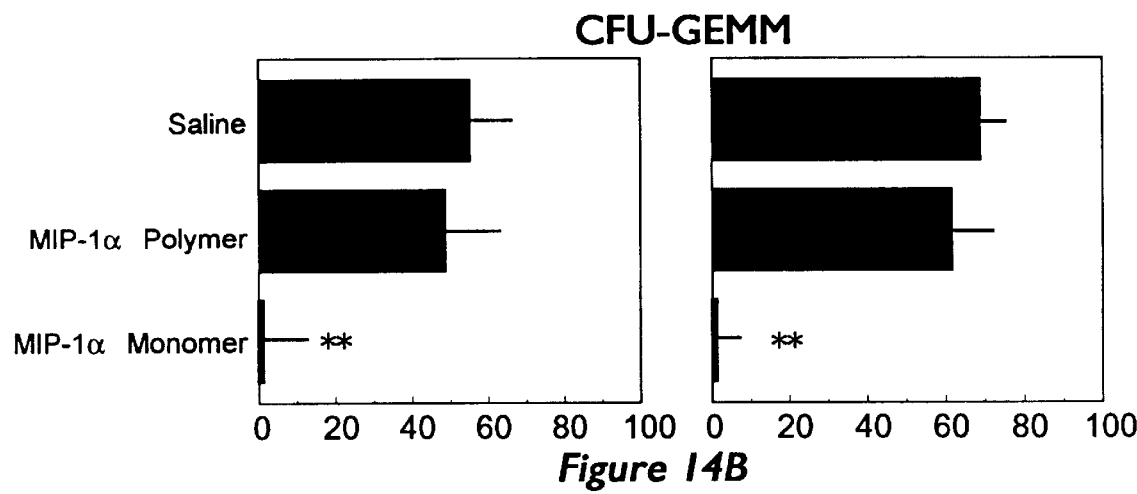
Figure 14C:
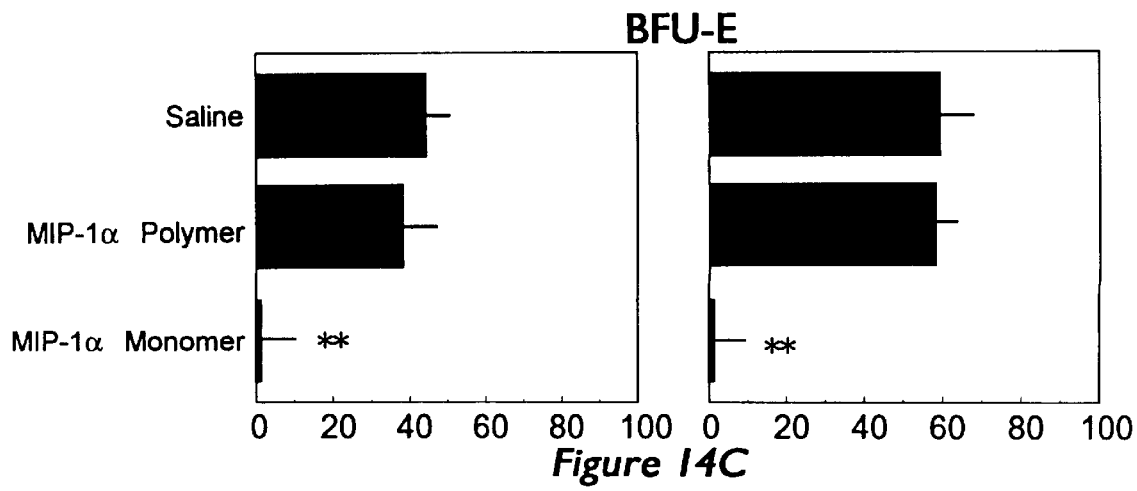
Figure 15A:
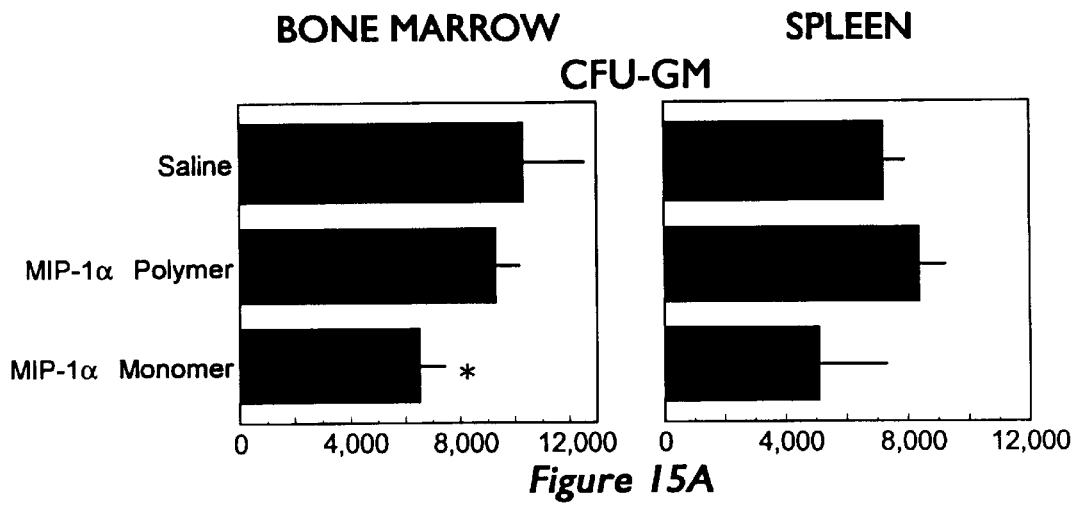
FIG. 15: Comparative influences of monomeric (8 ng) and polymerized (200 ng) rmuMIP-1α on the absolute numbers of BFU-E, CFU-GEMM and BFU-E in the marrow and spleen of C3H/H3J mice 24 hrs after a single injection i.v. of MIP-1α. These are the same mice assessed in FIG. 5. Significant % change from saline control: *p<0.005; **p <0.001; other numbers are not significantly different from control, p>0.05.
Figure 15B:
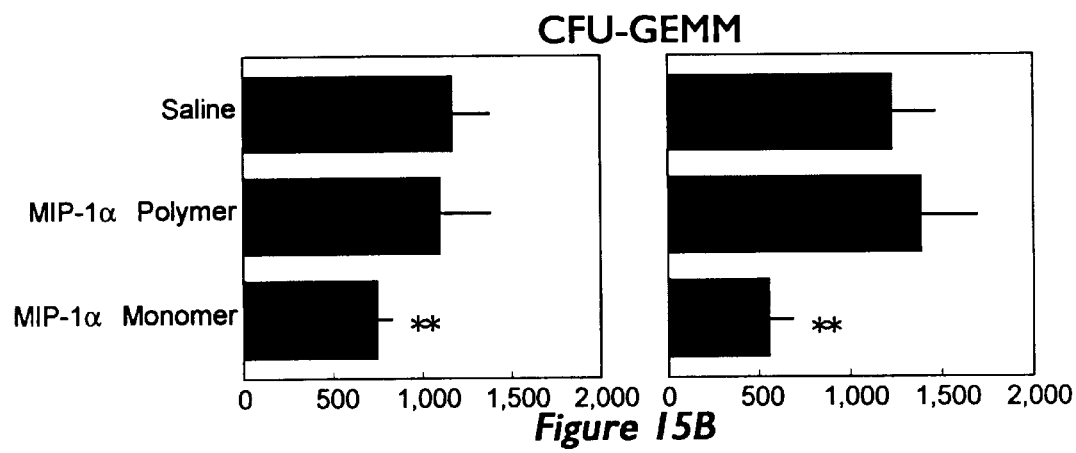
Figure 15C:
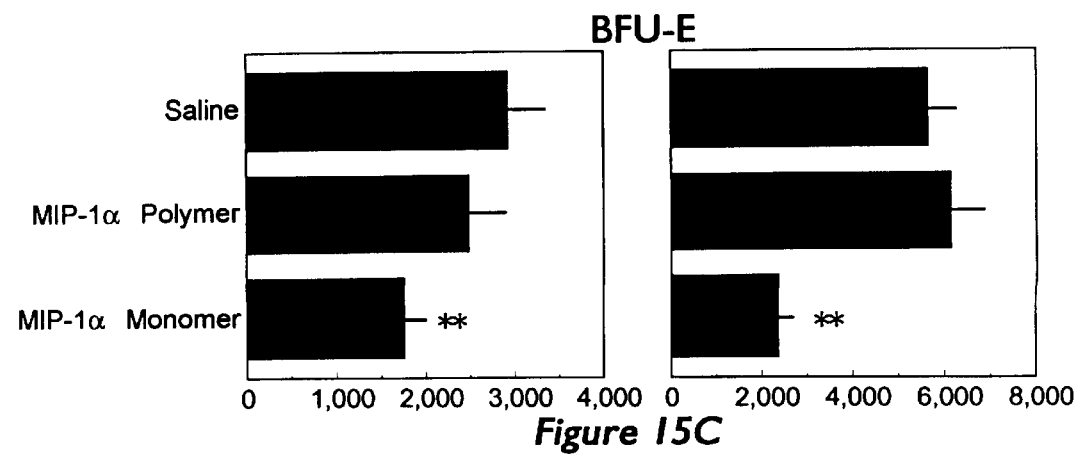

Preparations of rmuMIP-1α were assessed for suppressive activity on colony formation by CFU-GM in $BDF_1$ bone marrow cell cultures stimulated by GM-CSF plus SLF (FIG. 7). MIP-1α diluted in PBS to >20 ng/ml suppressed total colony formation by about 40% at 50 to 100 ng/ml (p <1; two tailed student's t test). Activity was lost at ≦10 ng/ml, and up to 1000 ng/ml was no more suppressive than 100 ng/ml. MIP-1α does not suppress colony formation stimulated by only GM-CSF, and inhibition was actually 100% of the enhanced number of colonies seen with cells stimulated by GM-CSF plus SLF compared to GM-CSF alone (this phenomenon is seen in FIG. 9A).

After separation of the MIP-1α diluted in PBS (FIG. 6A), the monomeric form (too little to be detected by UV absorption) was the only active form. The monomer was suppressive at concentrations to 0.005 ng/ml (p<0.01). Separated MIP-1α polymer, up to 300 ng/ml, was not active (p>0.1). Three weeks after storage at 4° C., the separated monomeric MIP-1α in PBS was still as active as that assayed immediately after collection, and the separated polymerized MIP-1α was still inactive (FIG. 7). Rechromatography demonstrated that the monomer remained monomer and the polymer remained polymer. Since monomer was separated at low concentration, this suggested that the physical stability of both forms of MIP-1α might relate to the concentration of MIP-1α in PBS. When MIP-1α in ACN was diluted into PBS at a final concentration ≦5 ng/ml, the curve for suppression was superimposeible with that of the separated monomeric form of MIP-1α (FIG. 7). Incubation of separated MIP-1α polymer in ACN for about 18 hours at 4° C. resulted in the reappearance of monomeric MIP-1α and active suppressive activity (FIG. 7).

Monomeric and polymerized rmuMIP-α fractions were also assessed for effects on colony formation of normal hu bone marrow cells. Separated MIP-1α polymer had no significant effect on colony formation at 50 to 200 ng/ml (+2 to −5% change from control values of 58±4 CFU-GM colonies/$10^5$ cells stimulated with rhuGM-CSF and rhuSLF; p>0.1). Separated MIP-1α monomer, at the lowest concentration assessed, 0.5 ng/ml, suppressed colony formation by 53% (p<0.001). Monomeric MIP-1α (0.5 ng/ml) also suppressed by 44 to 54% colony formation of hu marrow BFU-E and CFU-GEMM (p<0.0001; control colonies: 79±6 BFU-E, 26±3 CFU-GEMM, stimulated by rhuEpo and rhuSLF). Separated MIP-1α polymer, at 50 to 200 ng/ml, had no effect on colony formation by BFU-E or CFU-GEMM. Monomeric MIP-1α was without effect on hu colony formation by CFU-GEMM stimulated with only rhuGM-CSF and by BFU-E and CFU-GEMM stimulated with only rhuEpo.

Figure 8:
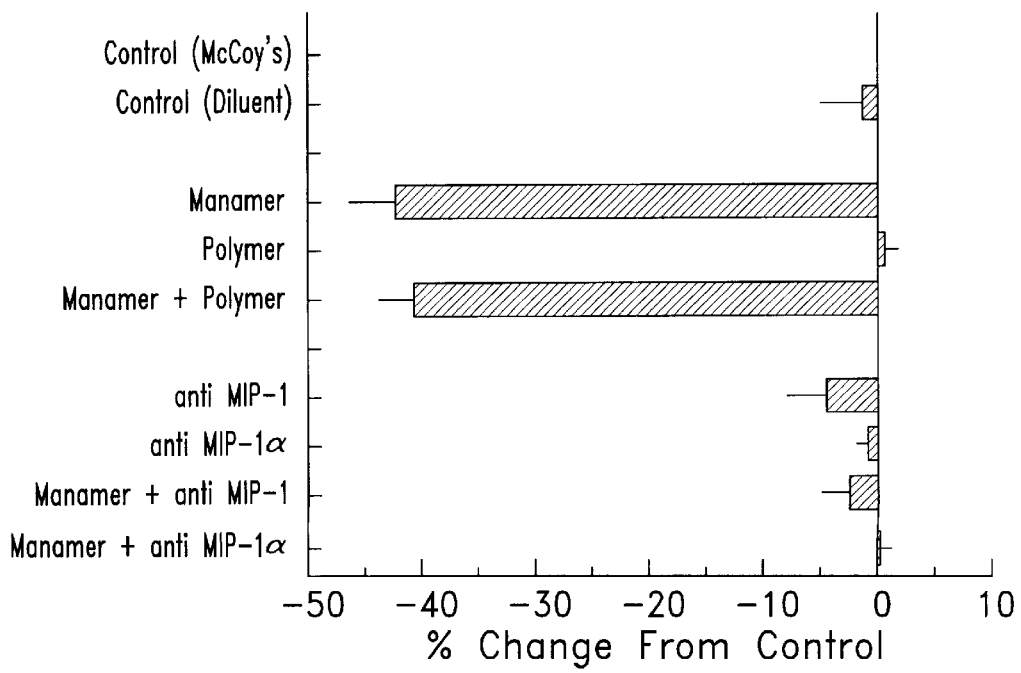
FIG. 8: Influence of separated rmuMIP-1α polymer and anti-MIP-1α on myelosuppression by monomeric rmuMIP-1α on mouse marrow CFU-GM. Results of 4 experiments are expressed as mean percentage change±1 SEM of colony formation compared to control (McCoy's) medium. Assays were performed as in FIG. 2 and percentage changes are based on control colony numbers of 83±4, 137±12, 121±4 and 91±5. Monomeric and polymerized rmuMIP-1α were obtained after column separation as in part A of FIG. 1 and were assayed, at monomer to polymer concentrations (ng/ml) of 0.1:50.0, 0.4 to 300.0, 2.4 to 81.0 and 0.005:12.5 (respective monomer:polymer ratios of 1:500, 1:750, 1:34 and 1:2500). For antibody neutralization studies, amounts of monomeric rmuMIP-1α which yielded final concentrations of 0.4 to 2.4 ng/ml MIP-1α in the test plates were preincubated with either control (McCoy's) medium or the purified immunoglobin fractions of polyclonal rabbit anti-natural muMIP-1 or rabbit anti-rmuMIP-α for 1 hour at room temperature.

As seen in FIG. 8, the separated polymerized form of rmuMIP-1α, even at a polymer to monomer ratio of 2500 to 1, did not block the suppressive activity of the monomer. Moreover, the suppressive activity of the monomeric MIP-1α was completely neutralized by preincubation of monomeric MIP-1α with both the polyclonal antibodies against the natural muMIP-1, which recognizes MIP-1α, and against the rmuMIP-1α (FIG. 8). This substantiates the identity of MIP-1α as the sole suppressive agent in the preparation.

To evaluate whether monomeric MIP-1α acted on the DNA synthesis (S)-phase of the cell cycle, monomeric MIP-α was assessed for effects on colony formation of mouse marrow cells in which the cells were first pulse-treated with high specific activity tritiated thymidine ($^3$HTdr) to remove cells in S-phase of the cell cycle prior to addition of MIP-α to the cultures (FIG. 9A). While CFU-GM that formed colonies in the presence of GM-CSF, or GM-CSF plus SLF, each had about 40–50% of cells in cycle at the start of the culture, only the CFU-GM stimulated by GM-CSF plus SLF were suppressed by MIP-1α. Addition of MIP-1α to cells stimulated with GM-CSF plus SLF that had survived pretreatment with $^3$HTdr, namely cells not in S-phase, did not influence colony formation. These results evidenced that MIP-1α initiates its suppressive effects during S-phase of the cell cycle. Even though the specific activity of the MIP-α used here is about 1000 fold increased compared to that reported previously, (see, Graham et al., *Nature*, Vol. 344, pp. 442 (1990); Broxmeyer et al., *Blood*, Vol. 76, pp. 1110 (1990); Broxmeyer et al., *J. Immunol.*, Vol. 147, pp. 2586 (1991); and Bodine et al., *Blood*, Vol. 78, pp. 914 (1991), suppression is still restricted to the relatively immature populations of progenitors. S-phase specificity was more rigorously substantiated by results in FIG. 9B (cells were stimulated with GM-CSF plus SLF). Suppression was the same whether cells were plated in MIP-1α or pulsed with $^3$HTdr or MIP-1α, pulsed with $^3$HTdr followed by pulsing with MIP-1α or pulsed with MIP-1α followed by pulsing with $^3$HTdr. Addition of MIP-1α to cells pulsed with these combinations did not further decrease colony numbers.

Figure 18A:
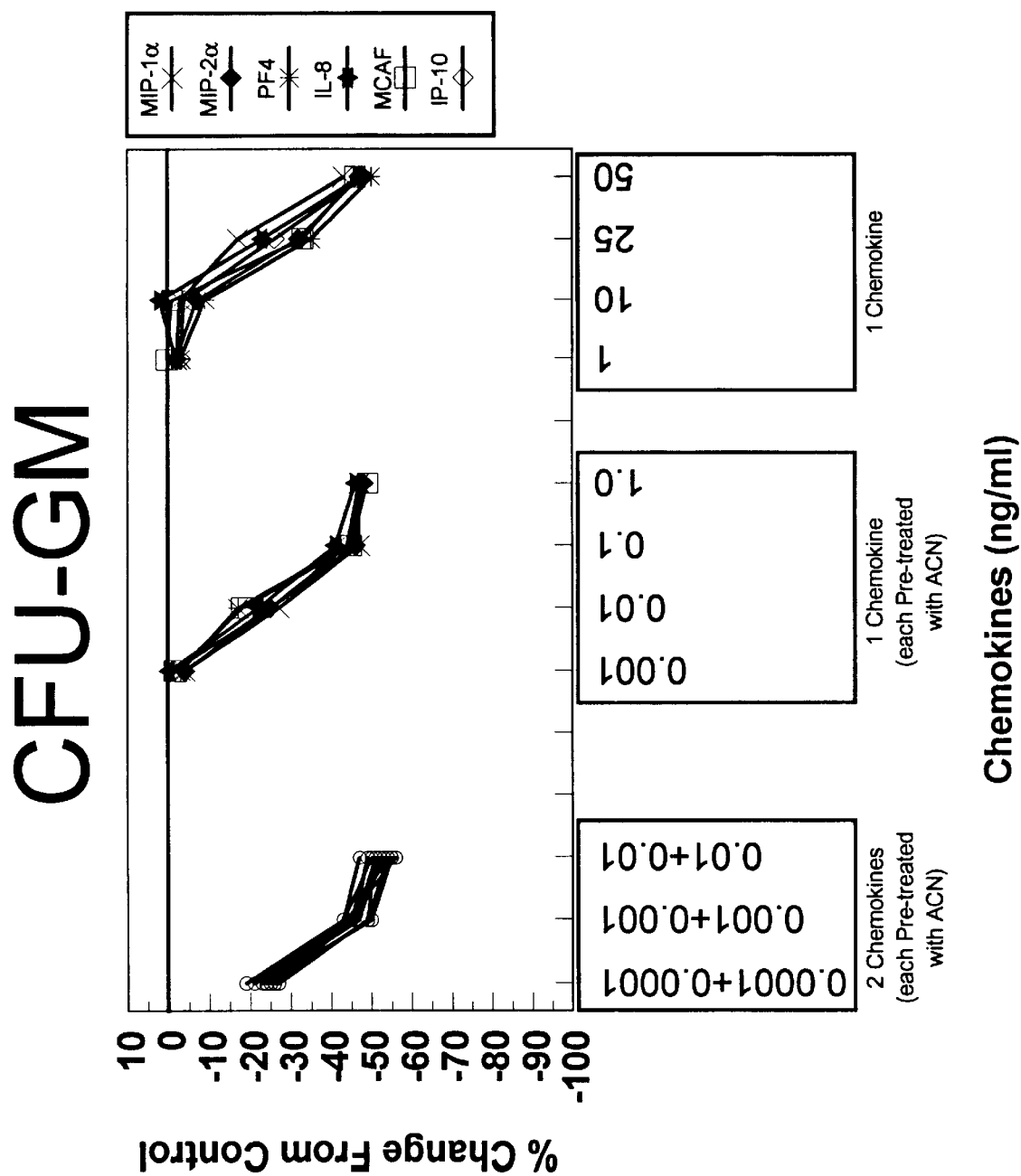
FIGS. 18A, 18B and 18C: Influence of pretreatment of chemokines with ACN on colony formation by FIG. 18A) CFU-GM, FIG. 18B) BFU-E, and FIG. 18C) CFU-GEMM in low density bone marrow cells stimulated by GM-CSF and SLF for CFU-GM, and by Epo and SLF for BFU-E and CFU-GEMM. Compared are effects of each untreated chemokine alone (right portion of each graph) with that of each ACN-treated chemokine alone (middle portion of each graph) with that of the combination of each of two ACN-treated chemokines (left portion of each graph). The key for symbols of effects of each individual chemokine is to the far right of each graph. Results are expressed as mean percentage change from control+/−SEM for 3 complete experiments for BFU-E and CFU-GEMM using single untreated chemokines, for 5 complete experiments for CFU-GM and 2 complete experiments for BFU-E and CFU-GEMM using single ACN-treated chemokines, and for 3 complete experiments for CFU-GM and 1 complete experiment for BFU-E and CFU-GEMM using combinations of ACN-treated chemokines. The symbols in the graph are each inclusive of the mean plus SEM bars. Control numbers of CFU-GM colonies were: 107±5, 66±2, 59±2 and 52±3. Control numbers of BFU-E colonies were 20±1, 16±2, and 105±2. Control numbers of CFU-GEMM colonies were 54±3, 53±2, and 37±3.
Figure 18B:
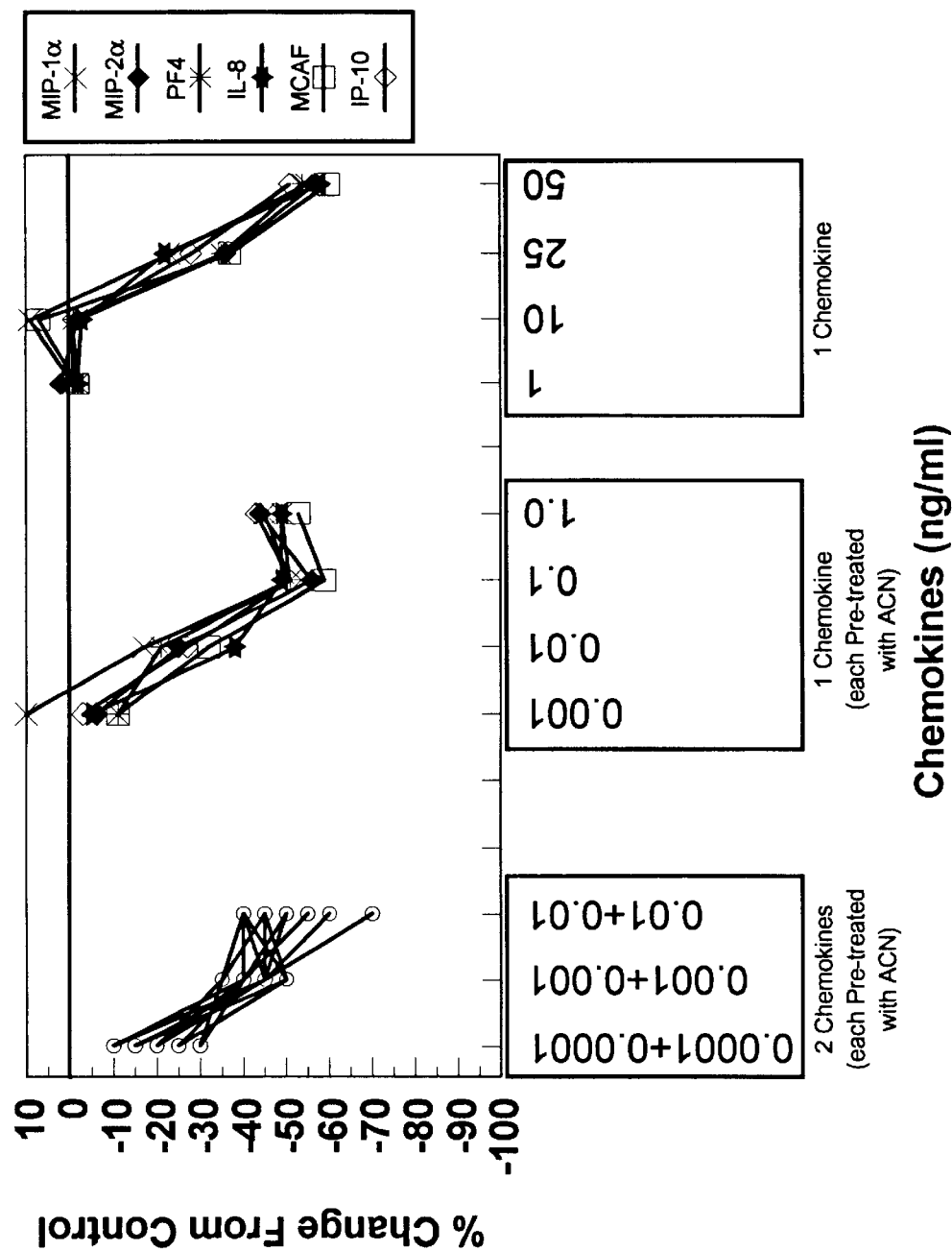
Figure 18C:
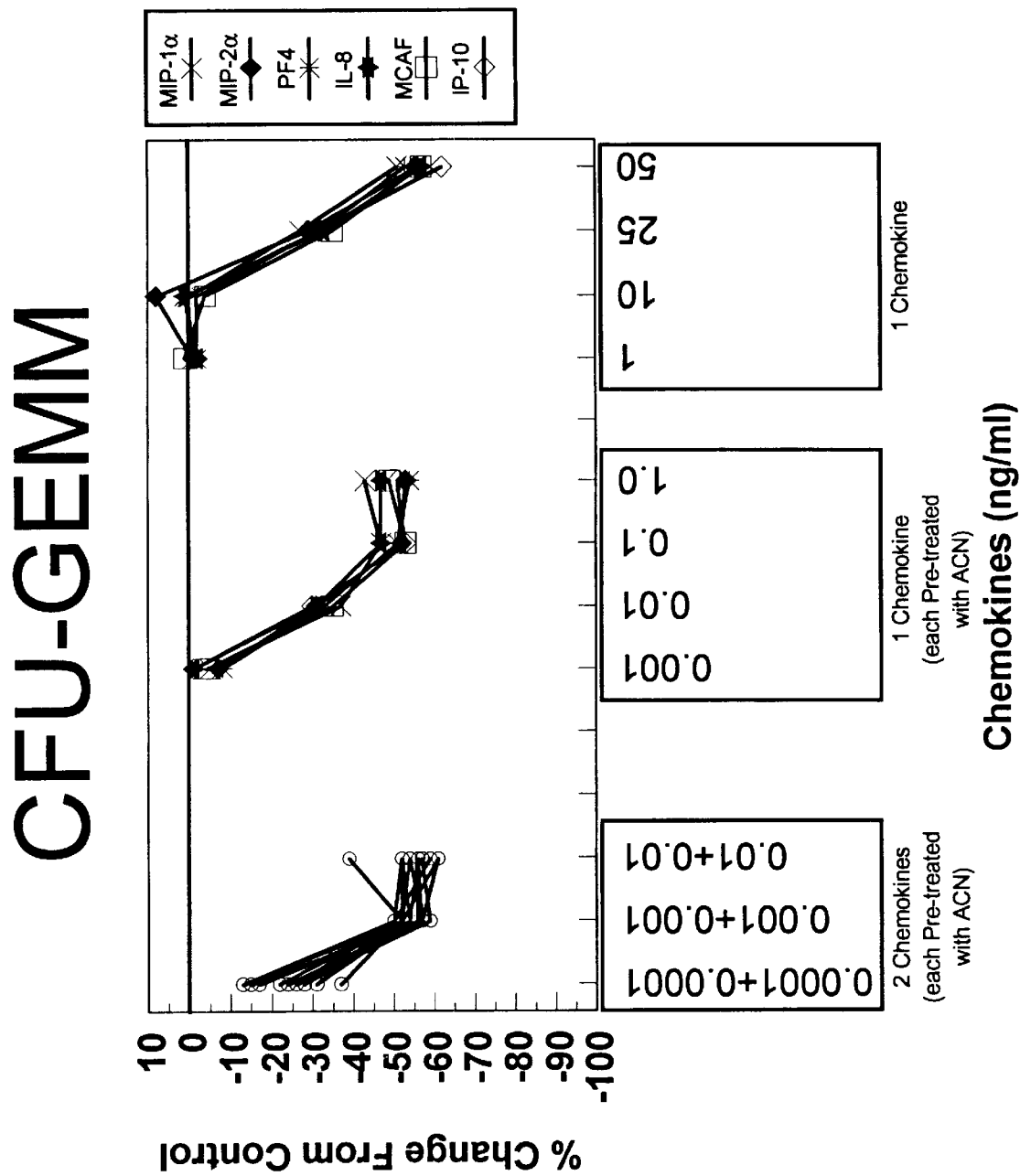

In testing analogous to that described above for monomeric MIP-1α, monomeric forms of IL-8, MCAF, PF4 and IP-10 showed much higher suppressive activity than their corresponding non-monomeric forms (see Table 3). Further testing using combinations of two or more chemokines each in monomeric form revealed that monomeric chemokines also synergize and, on a weight to weight basis, result in significant suppression with far less protein than when combinations of their non-monomeric forms are used. (see FIG. 18).

These results demonstrate that monomeric forms of chemokines such as MIP-1α, MIP-2α, PF4, IL-8, IP-10 and MCAF are suppressive and can be used in amounts far lower than their corresponding forms substantially comprised of their polymers.

Furthermore, the in vivo methodology in mice of Maze et al., *J. Immunol* 149:1004 (1992), was used to determine that the specific activity of the chemokines is also increased in vivo when the chemokines are administered in monomeric form. Thus, when mice (C3H/HeJ mice, Jackson Laboratories, Bar Harbor, Me.) were used in in vivo testing as described in R. Maze e al., supra, except using a substantially monomeric MIP-1α preparation, myelosuppressive effects in vivo were also demonstrated, and this suppression with monomeric chemokine was seen in vivo with 2500-fold less, on a weight-weight basis, than the MIP-1α material used in previous reports (see, Maze, et al., supra, Dunlop, et al., supra, and Lord, et al., supra.

The results of this in vivo testing of MIP-1α as well as similar testing of other MIP-1α-family chemokines are detailed in FIGS. 10–15 and Table 4. As can be seen, the chemokine preparations had high suppressive activity in vivo, both in terms of suppression of numbers of progenitors and the percent of progenitors in the S-Phase.

TABLE 3

Influence of Chemokines Separated by Gel Filtration on Superose-12 Columns (Pharmacia) on Colony Formation by CFU-GM in Normal Human Bone Marrow Cells.

| | | Colonies ± 1 SEM (% Change from Control) | | | |
|---|---|---|---|---|---|
| Chemokine | Dilution Assayed | Monomeric[b] | Non-monomeric | Non-monomeric | Non-monomeric |
| Control Diluent = PBS | | 94 ± 7 | | | |
| IL-8 | Undil. | 41 ± 3 (−56)[a] | 93 ± 5 (−1)[c] | | |
| | 1:10 | 59 ± 1 (−37)[a] | 90 ± 3 (−4) | | |
| | 1:100 | 94 ± 5 (0) | | | |
| MCAF | Undil | 41 ± 3 (−56)[a] | 86 ± 3 (−9)[c] | | |
| | 1:10 | 62 ± 2 (−34)[a] | 94 ± 5 (0) | | |
| | 1:100 | 88 ± 4 (−6) | | | |
| PF4 | Undil | 41 ± 2 (−56)[a] | 85 ± 6 (−10)[c] | | |
| | 1:10 | 52 ± 2 (−45)[a] | 92 ± 2 (−2) | | |
| | 1:100 | 69 ± 2 (−27)[a] | | | |
| IP-10 | Undil | 50 ± 5 (47)[a] | 88 ± 3 (−6)[c] | 92 ± 4 (−2)[d] | 85 ± 6 (−10)[e] |
| | 1:10 | 56 ± 1 (−40)[a] | 88 ± 4 (−6) | 94 ± 4 (0) | 96 ± 5 (+2) |
| | 1:100 | 91 ± 6 (−3) | | | |

Results are expressed per $10^5$ low density bone marrow cells plated in presence of 100 μ/ml rhuGM-CSF plus 50 ng/ml rhuSLF after 14 days incubation of cells at 5% $CO_2$, 5% $O_2$ in a humidifed chamber.
Chemokine sample was assayed at 0.1 ml per 1 ml culture medium at designated dilutions.
[a]Significant change from control diluent, p < 0.01; other numbers not significantly different from control.
[b]Chemokines were considered to be monomeric if they eluted at a molecular weight consistent with a monomeric form. This was an approximate range of 8–12 Kd for rhuIL-8, rhuMCAF and rhuPF4 and rhuIP-10.
[c]Elution of chemokine at approximate molecular weight consistent with that of dimer.
[d]Elution of IP-10 at approximate molecular weight ranging from 25,000–100,000 (Oligomer?).
[e]Elution of IP-10 at approximate molecular weight greater than 100,000 (polymer?).

TABLE 4

Comparative Influences In Vivo of Purified Human Chemokines on Absolute Numbers and Cycling Rates of Myeloid Progenitor Cells in the Marrow of C3H/HeJ Mice.[a]

| | Progenitors Per Femur × $10^{-3}$ | | | Percent Progenitors in S-Phase | | |
|---|---|---|---|---|---|---|
| Chemokine | CFU-GM | BFU-E | CFU-GEMM | CFU-GM | BFU-E | CFU-GEMM |
| Control Diluent | 15.3 ± 1.7 | 4.5 ± 0.5 | 2.1 ± 0.2 | 51 ± 9 | 57 ± 4 | 68 ± 3 |
| MIP-1α | 9.7 ± 1.1[b] | 2.2 ± 0.3[b] | 0.7 ± 0.2[b] | −3 ± 4[c] | 7 ± 2[c] | 5 ± 5[c] |
| MIP-2α | 10.3 ± 1.7[b] | 1.8 ± 0.2[b] | 0.4 ± 0.1[b] | 12 ± 3[c] | 1 ± 5[c] | 9 ± 12[c] |
| PF4 | 9.4 ± 0.5[b] | 2.3 ± 0.3[b] | 0.7 ± 0.1[b] | 3 ± 2[c] | 0.2 ± 2[c] | −1 ± 4[c] |
| IL-8 | 8.8 ± 0.9[b] | 2.7 ± 0.3[b] | 1.0 ± 0.1[b] | 4 ± 7[c] | −0.4 ± 2[c] | −2 ± 5[c] |
| MCAF | 8.8 ± 0.8[b] | 2.8 ± 0.2[b] | 0.9 ± 0.1[b] | 4 ± 3[c] | −8 ± 3[c] | 3 ± 8[c] |
| IP-10 | 8.8 ± 0.4[b] | 2.6 ± 0.4[b] | 1.0 ± 0.2[b] | −1 ± 1[c] | 1 ± 6[c] | −6 ± 6[c] |

TABLE 4-continued

Comparative Influences In Vivo of Purified Human Chemokines on Absolute Numbers and Cycling Rates of Myeloid Progenitor Cells in the Marrow of C3H/HeJ Mice.[a]

| Chemokine | Progenitors Per Femur × $10^{-3}$ | | | Percent Progenitors in S-Phase | | |
|---|---|---|---|---|---|---|
| | CFU-GM | BFU-E | CFU-GEMM | CFU-GM | BFU-E | CFU-GEMM |
| MIP-2β | 17.5 ± 1.4 | 5.9 ± 0.7 | 2.6 ± 0.4 | 59 ± 3 | 59 ± 2 | 65 ± 7 |
| GRO-α | 13.1 ± 1.2 | 5.1 ± 0.7 | 2.5 ± 0.2 | 55 ± 2 | 59 ± 6 | 70 ± 6 |
| RANTES | 13.1 ± 0.6 | 5.9 ± 0.7 | 1.9 ± 0.3 | 56 ± 2 | 51 ± 1 | 64 ± 3 |

[a]Mice were injected i.v. with 0.2 ml of control diluent or 8 ng/ml of ACN-treated chemokines. Mice were sacrificed 24 hrs later. These studies were done exactly as reported in Maize et al. J. Immunol. 149: 1004, 1992 for recombinant murine MIP-1α. Results shown are mean ± 1 SEM for 2 experiments in which a total of 7, 6 and 3 mice were individually assessed respectively for (control diluent), (rhuMIP-1α, rhuPF4, rhuIL-8, rhuMCAF, rhuIP-10) and (rhuMIP-2α, rhuMIP-2β, rhuGRO-α rhuRANTES). The percent progenitors in S-phase are based on control colony numbers of cells treated without tritiated thymidine that ranged from 37–118, 8–42 and 3–18 repsectively for CFU-GM, BFU-E and CFU-GEMM.
[b]Significant % change compared to control, $p < 0.05$
[c]Significant % change compared to control, $p < 0.001$ Preparation of rhuIP-10

Cloning of IP-10

The cloning of IP-10 cDNA and the affinity purification of antibodies against residues 10–98 (anti-IP-10), and 77–98 (anti-22) of IP-10 have been described elsewhere (Luster et al., 1985, Luster et al., 1987). Below is a brief description of the procedures.

Cell Culture

Human endothelial cells were isolated from umbilical cord veins (Jaffe et al., Culture of human endothelial cells derived from umbilical veins. Identification by morphologic and immunologic criteria, J. Clin. Invest. 52:2745 (1973)) and grown in M199 medium supplemented with 20% heat-inactivated human serum, penicillin (100 U/ml), and streptomycin (100 μg/ml). All the studies were performed on second-passage human umbilical cord endothelial cells (HUVE). A primary keratinocyte cell line isolated from human foreskin was obtained from Clonetics Corporation (Boulder, Colo.) and maintained in a defined keratinocyte growth medium (Tsao et al., Clonal growth of normal human epidermal keratinocytes in a defined medium, J. Cell. Physiol. 110:219 (1983). PBMC were isolated from venous blood fractionated on a Ficoll-Hypaque gradient. Monocytes were isolated from these PBMC by Percoll gradient fractionation (Wright et al., Tumor-promoting phorbol esters stimulate C3b and C3b' receptor-mediated phagocytosis in cultured human monocytes, J. Exp. Med. 156:1149 (1982)) and maintained in α-modified Eagle's medium (αMEM) supplemented with 10% heat-inactivated autologous human serum or FCS, penicillin, and streptomycin. FS4 cells were grown in αMEM supplemented with 10% FCS, penicillin, and streptomycin.

All induction experiments were performed in the regular cell growth media, using cells just before reaching confluence. Monocytes were induced at $10^6$ cells/ml in Teflon dishes.

IFN-γ

This was a highly purified recombinant protein synthesized in E. coli generously provided by Genentech, Inc., San Francisco, Calif. The endotoxin levels were determined in a limulus amoebocyte lysate assay before shipping. The human rIFN-γ had a specific activity of 2–4×$10^7$ U/mg as determined in a human lung carcinoma A549 inhibition assay using the encephalomyocarditis virus.

Peptide Synthesis

The peptide was synthesized by the solid-phase method (Barany et al., Solid phase peptide synthesis, In The Peptides. Vol. II. E. Gross and J. Meinhoper, editors, Academic Press, New York. 1–284 (1979)) using chloromethylated, 1% crosslinked, styrene-divinylbenzene copolymer (Merrified Resin). Deprotection was followed by a coupling program that used the symmetric anhydrides of the appropriate Boc amino acids (Bachem Inc., Torrance, Calif.; or Peninsula Laboratories, Inc., Belmont, Calif.) (Yamashiro and Li, 1978). The side-chain functionalities were protected by benzyl-type protecting groups. The peptide was cleaved from the resin and deprotected by treatment with liquid HF-anisole at ~0° C. (Scotchler et al., Cleavage of single amino acid residues from purified resin with hydrogen chloride and hydrogen fluoride, J. Org. Chem. 35:3151 (1970)). The peptide was purified by gel-permeation chromatography, ion-exchange chromatography, and reverse-phase HPLC. The final product was homogeneous by analytical reverse-phase HPLC.

The peptide was glutaraldehyde coupled to keyhole limpet hemocyanin (KLH) (Pfaff et al., Antibodies against a preselected peptide recognize and neutralize foot and mouth disease virus, EMBO (Eur. Mol. Biol. Organ.) J. 1:869 (1982)). 2 μg of peptide was dissolved 10 μl of $H_2O$ and added to 15 ng KLH in 2 ml 0.1 M PBS. Glutaraldehyde (21 mM) was added over 1 h at room temperature. The mixture was allowed to stand overnight at room temperature and then was dialyzed against PBS.

~100 μg of protein in CFA was used to immunize two 8-wk-old female New Zealand white rabbits. The rabbits were boosted twice at 1-month intervals with the same amount of protein in IFA. 10 days after the second boost, the rabbit was bled and serum was isolated and used for Western blotting and immunoprecipitation.

E. coli Expression and Production of Antiserum

A 576-bp Xba I-Eco RI derived from the IP-10 cDNA plasmid pIFNγ-31.7 (4) was cloned into the fusion expression vector pB4[+] (Matsuura et al., Baculovirus expression vectors: the requirements for high level expression of proteins, including glycoproteins, J Gen Virol, 68:1233 (1987)). The pB4[+] vector contains the gene for the influenza viral protein NSI. The plasmid was transformed into the E. coli strain AR58, which is a λ lysogen containing a temperature-sensitive mutation in the CI gene (CI857). The resulting strain, harboring the recombinant expression plasmid, produced a fusion protein at the nonpermissive temperature that consisted of 81 amino acids of NSI and 72 amino acids of IP-10.

A 325-bp Fnu4H fragment derived from the IP-10 cDNA plasmid pIFNγ 31.7 was cloned into the nonfusion expression vector pT17. This recombinant plasmid was transformed into the *E. coli* strain AR58, which upon temperature induction synthesized 88 amino acids of the IP-10 protein.

Bacterial cells were grown in L-broth at 30° C. to an $OD_{650}$ of 0.3, then shifted to 42° C. for 1 h of growth. The bacterial cells were pelleted by centrifugation and resuspended in 1/20 vol of PBS. The cells were lysed by sonication and subjected to centrifugation at 10,000 rpm for 5 min. The pellet, which included the recombinant proteins and cellular envelopes, was suspended in sample buffer and subjected to preparative SDS-PAGE. The gel was stained with Coomassie Brilliant Blue R for 1 min and immediately washed five times in deionized water. The faintly stained band was excised from the gel with a razor blade and minced. The gel pieces were soaked for 24 h in 50 mM Tris, pH 7.5, containing 0.15 M NaCl and 0.1% SDS. The amount of eluted protein recovered was estimated by comparison to protein standards (Bio-Rad Laboratories, Richmond, Calif.) after SDS-PAGE. This treatment of the sample resulted in a preparation highly enriched for recombinant proteins.

~100 μg of protein in CFA was used to immunize an 8-wk-old female New Zealand white rabbit. The rabbit was boosted twice at 1-month intervals with the same amount of protein in IFA. 10 days after the second boost, the rabbit was bled and serum was isolated and used for Western blotting and immunoprecipitation.

IgG was isolated from serum by protein A-Sepharose affinity chromatography (Pharmacia Fine Chemicals, Piscataway, N.J.). 1 mg of the gel-purified recombinant protein was coupled to cyanogen bromide-activated Sepharose 4B (Pharmacia Fine Chemicals). 100–200 mg IgG was affinity purified on the recombinant protein column. The bound IgG was eluted with 1 M glycine-HCl, pH 2.8, quickly neutralized with 2 M Tris, and dialyzed against PBS. The affinity-purified antiserum was used for immunoprecipitation, immunofluorescence, and immunohistochemistry.

Pulse-chase Experiments

HUVE cell monolayers (~$10^6$ cells) were washed twice with PBS and maintained for 30 min in oMEM lacking methionine but containing 200 mM glutamine. Cells were then pulsed for 30 min in this cell-starvation medium supplemented with [$^{35}$S]methionine (500 μCi/ml). After removal of the pulse medium, the cells were washed twice with PBS and then incubated with cell growth medium supplemented with unlabeled methionine (5 mM) for the chase periods indicated. At the completion of the chase, the monolayers were washed twice with PBS and scraped into an SDS solution (0.5% SDS, 50 mM Tris, pH 7.4, 100 mM NaCl, 2 mM EDTA). After being heated for 2 min at 100° C., the samples were frozen at -20° C. For immunoprecipitation, the samples were again heated for 2 min at 100° C., sonicated for 2 min, and adjusted to contain 0.2 U/ml aprotinin (Sigma Chemical Co., St. Louis, Mo.), and 1 mM PMSF (Sigma Chemical Co.). Affinity-purified antibodies were added to a final concentration of 5 μg/ml and the immunoprecipitation was continued as described below.

Immunoblotting

*E. coli* cells or human cell lysates (prepared as described) were dissolved in sample buffer (2% SDS/0.0625 M Tris, pH 7.4/10% glycerol/0.01% bromphenol blue/and 5% 2-ME), boiled for 5 min, and fractionated by SDS-PAGE using slab gels of 12.5 and 15% acrylamide. Prestained protein molecular weight standards (Bethesda Research Laboratories, Gaithersburg, Md.) were used to calculate apparent molecular weights. Protein was transferred electrophoretically to nitrocellulose (Schleicher & Schuell, Inc., Keene, N.H.). All of the following steps were performed in Tris-buffered saline (TBS; 50 mM Tris, pH 7.5, 2 mM EDTA, 0.15 M NaCl), 0.5% NP-40, and 0% FCS. The nitrocellulose filter was first treated overnight in 5% nonfat dry milk, followed by incubation for 2 h with a 1:1,000 dilution of antiserum. The nitrocellulose was washed and reacted for 1 h with $10^6$ cpm/ml of $^{125}$I Staphylococcus protein A (Amersham Corp., Amersham, Arlington Heights, Ill.). After extensive washing in TBS+0.5% NP-40, the filter was exposed to x-ray film at -70° C. in the presence of an intensifying screen.

Immunoprecipitation

~$10^6$ cells were lysed in PBS containing 1% NP-40, 0.2 U/ml aprotinin, 1 mM PMSF, and 0.1% diisopropylfluorophosphate (Sigma Chemical Co.). Nuclei and debris were removed by centrifugation at 14,000 g for 5 min. The lysate was adjusted to 0.2% SDS and boiled for 5 min at 100° C. The lysate was further clarified by centrifugation at 45,000 g, 15 min at 4° C. The supernatant was passed through a 0.45-μm millex filter and further clarified by centrifugation at 45,000 g, 15 min at 4° C. Affinity-purified antibodies were added to a final concentration of 5 μg/ml to both lysate and supernatant. The solution was incubated at room temperature for 4–16 h. Antigen-antibody complexes were precipitated by incubation with protein A-Sepharose for 2 h at room temperature.

The immunoabsorbed protein A-Sepharose beads were collected by centrifugation, washed twice in buffer that contained 0.6 M NaCl, 0.0125 M $KPO_4$, pH 7.4, and 0.02% $NaN_3$ (HSA buffer), twice at room temperature with a mixed detergent solution (0.05% NP40, 0.1% SDS, 0.3 M NaCl, and 10 mM Tris-HCl, pH 8.6), once again with HSA buffer, and finally, once in PBS. The antigen-antibody complexes were released from the beads by incubation at 100° C. for 2 min in 2× PAGE sample buffer.

$NH_2$-Terminal Sequence Determination

Human keratinocytes were biosynthetically labeled with [$^3$H]leucine and [$^{35}$S]cystein for 8 h. Radiolabeled IP-10 was purified from the keratinocyte media by immunoprecipitation and SDS-PAGE. The gels were dried down without fixing or staining. The IP-10 protein was located in the gel by autoradiography, electroeluted from the gel, and concentrated by precipitation (Schragger et al., Tricine-sodium dodecyl sulfate polyacrylamide gel electrophoresis for the separation of proteins in the range from 1 to 100 kDa, *Anal Biochem*, 166:368 (1987)). Samples were subjected to automated Edman degradation in Gas Phase Sequencer (Model 470A; Applied Biosystems, Inc., Foster City, Calif.). The amino acid derivative obtained at each cycle was dissolved in 20% acetonitrile and transferred to 10 ml of Aquasol for scintillation counting.

ELISA

The antipeptide antisera were checked for their ability to react with the synthetic peptide by an ELISA assay. Microtiter plates were coated with peptide (100 ng/well) in a sodium carbonate buffer, pH 9.6, and then saturated with 3% BSA, PBS, 0.1% Tween 20. 100 μl of antipeptide antisera dilutions from $10^{-2}$ to $10^{-7}$ were placed in the wells and incubated for 2 h. After extensive washing in PBS/0.05% Tween, the plates were incubated for 2 h with peroxidase-labeled affinity-purified goat anti-rabbit IgG. The wells were then washed and the substrate O-phenylenediamine (100 μl of 10 mg/25 ml in 0.05 M citrate phosphate buffer, pH 5) was added. The reaction was allowed to proceed for 10 min at room temperature and was stopped by addition of 50 ml of 2.5 M $H_2SO_4$. Absorbance was read at 410 nm in an automatic plate reader (Minireader II; Dynatech Laboratories, Inc., Alexandria, Va.). Positive ELISA readings were obtained at dilutions of 10-7 after boosting with peptide conjugate. The purified peptide was attached to CNBr-activated Sepharose 4B. This matrix was used to affinity purify the rabbit antipeptide antiserum. The affinity-purified antibodies were used for Western blotting and immunoprecipitation experiments.

RNA Isolation and Blotting

Total cellular RNA was isolated by the guanidinium isothiocyanate-cesium chloride method (Dreyfuss et al., Physical changes in cytoplasmioc messenger ribonucleoproteins in cells treated with inhibitors of mRNA transcription, *Mol Cell Biol* 4, 415–423 (1984)). RNA was fractionated on a 1% agarose gel containing 2.2 M formaldehyde (Irie, A highly sensitive silver staining for detection of proteins in polyacrylamide gels, *Biochemistry* (Japan), 52:411 (1980)) and transferred to nitrocellulose (Michaels et al, Inexpensive method for air-drying polyacrylamide electrophoresis gels, BioTechniques, 11:466 (1991)) and hybridized with a random primed (Towbin et al., Electrophoretic transfer of proteins from polyacrylamide gels to nitrocellulose sheets: Procedure and some applications, *Proc Natl Acad Sci USA*, 76:4350 (1979)) IP-10 cDNA probe (pIFNγ-31.7). Hybridization was performed at 40° C. for 16 h in a solution containing 50% formamide, 10% dextran sulfate, 5×SSC (1×SSC: 0.15 M sodium chloride, 0.015 M sodium citrate), 1×Denhardt's (0.02% polyvinyl-pyrrolidone, 0.02% Ficoll, and 0.02% BSA), and 200 μg/ml of sonicated herring sperm DNA. The filters were washed at 50° C. in 0.1×SSC containing 0.1% SDS and exposed at −70° C. to Kodak XAR film in the presence of one intensifying screen (Cronex Lightning Plus).

Expression in Insect Cells

Wild type baculovirus, Sf9 insect cells, and transfer vector pVL1392 (Webb and Summers, 1990) were provided by MD Summers (Texas A&M University, College Station, Tex.). Transfer vector pAcYM1 (Matsuura et. al., 1987) was provided by D. Bishop (NERC Institute of Virology, Oxford, UK). The Pst-1 fragment of the IP-10 cDNA was cloned in the Pst-1 site of pVL1392, and yielded recombinant baculoviruses 8555 and 9094. For elimination of its 5' untranslated sequences, the IP-10 cDNA was digested with Nla 3, the 375 nucleotide fragment was purified, ligated to GATCCATG, restricted with BamH1, and cloned into the BamHl site of pAcYM1, generating recombinant baculoviruses A213 and A221. Standard techniques were performed for isolation of recombinant baculoviruses (Webb et al., Expression of proteins using recombinant baculoviruses, *Technique* 2: 173 (1990); Sambrook et al., Molecular cloning: A laboratory manual. Second edition. Cold Spring Harbor Laboratory Press (1989)). All junctions between recombinant transfer vectors and IP-10 cDNA were sequenced (Sanger et al., DNA sequencing with chain-terminating inhibitors, *Proc Natl Acad Sci USA*, 74:5463 (1977) to exclude cloning artifacts. For production of rIP-10, Sf9 cells were infected with A221 (20 PFU/cell), 6-day supernatants were cleared at 100,000 G for 1 h at 4° C., dialyzed against 40 mM Na Phosphate pH 7.2, and loaded on a 15 ml Sepharose-S FPLC column. Proteins were eluted with a linear gradient of 0.0–2.0 M NaCl in 40 mM Na Phosphate pH 7.2 (150 ml), fractions containing rIP-10 were identified with a dot blot immunoassay (Sarris et al., Immunofluorescent localization and immunochemical determination of Cyclophilin-A with specific rabbit antisera, Transplantation, 54:904 (1992)) using anti-IP-10, and were loaded on a reverse-phase C4 HPLC column. Adsorbed rIP-10 was eluted with a gradient of 25% acetonitrile-50% propanol-25% $H_2O$ in 0.1% TFA, lyophilized and resuspended in endotoxin-free PBS.

Using two primers, A (GGATCCATGGTACCTCTCTCTAGAACC) (Sequence ID No.1) as 5' and B (GGATCCATGGTTAAGGAGATCTTTTAGA) (Sequence ID No.2) as 3' primer, a cDNA coding for f(22-98) was amplified (Saiki et al., Primer-directed enzymatic amplification of DNA with a thermostable DNA polymerase, *Science*, 239:487 (1988)). This segment, f(22-98) is a fragment lacking the signal peptide and extending from valine 22 to proline 98 of IP-10. With C (GGATCCATGGTTATGGATTCAGACATCTCTT) (Sequence ID No.3) as 3' and A as the 5' primer a cDNA coding for f(22-76) was also amplified. This segment encodes a fragment extending from valine 22 to proline 76 and lacking the signal peptide and the last 22 residues of IP-10, but retaining all 4 cysteine residues and approximating the previously reported secreted form of IP-10 (Luster et al., Biochemical characterization of a g Interferon-inducible cytokine (IP-10), *J Exp Med*, 166:1084 (1987)). The PCR products were restriction digested with Ncol and cloned in the Ncol site of pET-3d (provided by F. Studier, Brookhaven National Laboratories, New York) eliminating all amino acid residues of f10 (Studier et al., Use of T7 polymerase to direct expression of cloned genes, *Methods in Enzymology*, 185:60 (1990)), and expressing the rIP-10 fragments as nonfusion proteins with an added methionine at the amino terminus. The regions adjacent to and including the IP-10 cDNA were sequenced (Sanger et al., supra.) to exclude PCR and cloning errors. Lysogens BL21(DE3) transformed with recombinant plasmids were induced with 0.4 mM isopropylthiogalactoside (Studier et al., supra.), recombinant f(22-98) was purified (Lindley et al., Synthesis and expression in *Escherichia coli* of the gene encoding monocyte-derived neutrophil-activating factor: Biological equivalence between natural and recombinant neutrophil-activating factor, *Proc Natl Acad Sci USA*, 85:9199 (1988)) from refractile bodies (Marston), dialysed against Ca/Mg-free PBS, and stored in 1 ml aliquots at −70° C. Protein concentration was measured by dye binding (Bradford, A rapid and sensitive method for the quantitation of microgram quantities of protein utilizing the principle of protein-dye binding, *Anal Biochem*, 72:248. (1976)). Antiserum AS522 was raised against purified recombinant f(22-98) as described (Luster et al., supra.).

Natural human IP-10 was concentrated by TCA precipitation of serum-free media from primary human keratinocytes after 24 h induction by rIFN-g (Luster et al., supra.).

Expression of Recombinant IP-10

The gene encoding IP-10 was inserted into various baculoviral vectors for expression in eukaryotic cells. This expression resulted in processed IP-10 which was compared to a bacterially expressed fragment of IP-10 which lacks the putative signal sequence and with natural IP-10 from keratinocytes.

Materials

All chemicals were reagent grade. Protein molecular weight markers were from BRL (Gaithersburg, Md.). Ficoll-Hypaque, Protein A-Sepharose, and S-Sepharose were from Pharmacia (Piscataway, N.J.). EX-CELL-400 was from JR Scientific (Woodland, Calif.). The 4.6×150 mm C4 reverse phase column was from Vydac (Hesperia, Calif.). The Rapid-Ag Silver protein staining kit was from ICN (Cleveland, Ohio). rIFN-/ was a gift from Dr G. Garotta (Hoffman-LaRoche, Basel Switzerland). Human rMIP-1a and rMIP-2a were gifts of Dr B. Sherry (Picower Institute, Manhasset, N.Y.). Human rGM-CSF, human rIL-3 and human rSLF were gifts of the Immunex Corporation (Seattle, Wash.). Human rEPO was purchased from Amgen (Thousand Oaks, Calif.), human platelet Factor 4 (PF4) and rIL-8 from Sigma (St Louis, Mo.), and human rMCAF from Repro Tech Inc, Rocky Hills, N.J.

Results

Recombinant baculoviruses 8555, 9094, A213 and A221 express rIP-10 as a nonfusion protein. In baculovirus 8555 the initiating codon, ATG of the polyhedrin gene is mutated to ATT, and protein synthesis starts 118 nucleotides downstream, at the initiating ATG of the IP-10 cDNA. In baculovirus 9094 the IP-10 was inserted in the same location but in reverse orientation. In A221 and A213 the initiating ATG of the polyhedrin gene is destroyed by deletion of nucleotides 2–751 of its coding region, and protein synthesis starts 8 nucleotides downstream at the initiating ATG of IP-10. Most 3'-untranslated sequences of the IP-10 were deleted from A213 and A221.

Analysis of protein synthesis after infection by 8555 and A221 demonstrated a major new band of 9.9 kDa, similar in size to IP-10 without the signal sequence (10.0 kDa), and a minor band of 11.9 kDa, similar in size to IP-10 with the signal sequence (12.4 kDa). Neither band was detected in uninfected cells or in cells infected with 9094 or with wild type virus. The 9.9 kDa but not the 11.9 kDa band was detected in supernatants of infected cells by autoradiography. Non-immune serum did not precipitate any proteins from cells infected with A221, but anti-IP-10 and anti-22 precipitated both bands. Western blotting with anti-IP-10 and anti-22 detected both bands in cells, but only the 10 kDa band in the media.

In order to precisely define the $M_r$ of baculovirus IP-10, f(22-98) and f(22-76) were used as molecular weight markers. These studies demonstrated that f(22-98) and IP-10 derived from either keratinocytes or baculovirus co-migrated at 10.2 kDa, and were recognized by anti-IP-10 and anti-22. Alternatively, f(22-76) migrated with an apparent $M_r$ of 6.2 kDa, and was recognized by anti-IP-10 but not by anti-22. The reactions of antiserum AS522 and anti-IP-10 in immunoprecipitations and western blots were identical.

Levels of rIP-10 were 5–10 times higher after infection with A213 and A221 than after infection with 8555, and were not affected by FCS reaching 9% of the total protein in the supernatant of cells grown in EXCELL-400. anti-IP-10 and a dot blot immunoassay were used to purify rIP-10 from supernatants of infected cells, and a major HPLC peak was obtained which ran as a single band on SDS-PAGE co-migrating with purified bacterial f(22-98). The faint bands near the top of the gels correspond in size to keratins, and were seen in unloaded lanes and in lanes loaded only with sample buffer. Western blotting confirmed that the purified band represented rIP-10, because it reacted with anti-IP-10 and anti-22 during all stages of purification.

Aminoterminal sequencing of baculovirus rIP-10 demonstrated a major amino terminal sequence of VPLSRTVROT (66%) and a minor sequence of RTVROT (34%), both matching the sequence of IP-10 secreted by keratinocytes (Luster et al., supra.). Sequencing of f(22-98) demonstrated a single sequence of MVPLSRTVROTOISISNQPVN matching the sequence of secreted IP-10 (Luster et al., supra.) with an additional aminoterminal methionine. The yield of purified rIP-10 was 0.5 µg/ml of supernatant in the baculovirus system and 5 µg/ml from the bacterial culture.

Purification of IP-10

Proteins were separated on 10–20% gradient PAGE in the presence of 0.2% SDS with 0.75 M Tris-HCl, pH 8.45, in the stacking gel; 1.0 M Tris-HCl, pH 8.45, in the separating gel; 0.2 M Tris HCl, pH 8.9 in the anode reservoir; and 0.1 M Tris-0.1 M Tricine in the cathode reservoir (Schragger et al., supra.). Protein gels were stained with silver (Irie, supra), and quantitated by densitometry. Western blots were performed on Immobilon-P (Sarris et al., supra; Towbin et. al., Electrophoretic transfer of proteins from polyacrylamide gels to nitrocellulose sheets: Procedure and some applications, *Proc Natl Acad Sci USA*, 76:4350 (1979)). rIP-10 was immunoprecipitated from Sf9 cells labeled with [$^{35}$S]-methionine after boiling in 500 µl of 0.2% SDS, 50 mM Tris-HCl, pH 7.5, and the sequential addition of NP-40 (final concentration of 1%), affinity purified antibodies (final concentration 5 µg/ml), and Protein-A beads (Sarris and Palade, 1982). The $M_r$ of IP-10 was estimated from the mobilities of marker proteins of 43-14.3 kDa. Aminoterminal sequencing was performed as described (Hewick et. al., A gas-liquid solid phase peptide and protein sequenator. J Biol Chem, 256:7990 (1981); Tempst et al., Examination of automated polypeptide sequencing using standard phenyl isothiocyanate reagent and subpicomole high-performance liquid chromatographic analysis, *Anal Biochem*, 183:290 (1989)).

All publications cited herein are hereby incorporated by reference in their entirety as if fully set forth.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. A process for suppressing myeloid cells in a mammal, comprising:
   administering to a mammal for which such suppression is desired a combination of two or more myeloid-cell-suppressive chemokines, wherein said two or more myeloid-cell-suppressive chemokines exhibit synergism in the suppression of proliferation of myeloid cells when said combination is administered to said mammal; and
   wherein said two or more myeloid-cell-suppressive chemokines comprise monomeric form chemokines.

2. The process of claim 1 wherein said synergistic combination includes at least one chemokine selected from the group consisting of Macrophage Inflammatory Protein-1α, Macrophage Inflammatory Protein-2α (MIP-2α), Platelet Factor 4 (PF4), Interleukin-8 (IL-8) and Macrophage Chemotactic and Activating Factor (MCAF).

3. The process of claim 1 wherein said combination comprises MIP-1α.

4. The process of claim 1 wherein said combination comprises MIP-2α.

5. The process of claim 1 wherein said combination comprises PF4.

6. The process of claim 1 wherein said combination comprises IL-8.

7. The process of claim 1 wherein said combination comprises MCAF.

8. A process for suppressing myeloid cells in a mammal, comprising:
   administering to a mammal for which such suppression is desired at least one myeloid-cell-suppressive chemokine at a concentration sufficient to maintain said at least one chemokine predominantly in monomeric form.

9. The process of claim 8 which includes administering at least one chemokine selected from the group consisting of Macrophage Inflammatory Protein-1α, Macrophage Inflammatory Protein-2α (MIP-2α), Platelet Factor 4 (PF4), Interleukin-8 (IL-8) and Macrophage Chemotactic and Activating Factor (MCAF).

10. The process of claim 8 which comprises administering MIP-1α.

11. The process of claim 8 which comprises administering MIP-2α.

12. The process of claim 8 which comprises administering PF4.

13. The process of claim 8 which comprises administering IL-8.

14. The process of claim 8 which comprises administering the MCAF.

15. A process for suppressing myeloid cells in a mammal, comprising:
   administering to a mammal for which such suppression is desired an effective amount of at least one chemokine selected from the group consisting of Macrophage Inflammatory Protein-2α (MIP-2α), Platelet Factor 4 (PF4), Interleukin-8 (IL-8) and Macrophage Chemotactic and Activating Factor (MCAF); and,
   wherein said at least one chemokine comprises monomeric form chemokine.

16. The process of claim 15 which comprises administering the chemokine MIP-2α.

17. The process of claim 15 which comprises administering the chemokine PF4.

18. The process of claim 15 which comprises administering IL-8.

19. The process of claim 15 which comprises administering the chemokine MCAF.

20. A process for suppressing myeloid cells in a mammal, comprising:
   administering to a mammal for which such suppression is desired a combination of two or more-myeloid-cellsuppressive chemokines selected from the group consisting of MIP1α, MIP2α, PF4, IL-8 and MCAF, wherein said two or more myeloid-cell-suppressive chemokines exhibit synergism in the suppression of proliferation of myeloid cells when said combination is administered to said mammal; and wherein said two or more myeloid-cell-suppressive chemokines comprise monomeric form chemokines.

21. A process for suppressing myeloid cells in a mammal, comprising:

administering to a mammal for which such suppression is desired at least one myeloid-cell-suppressive chemokine at a concentration sufficient to maintain said at least one chemokine predominantly in monomeric form, wherein said chemokine is selected form the group consisting of MIP1α, MIP2α, PF4, IL-8 and MCAF.

22. The process of claim 21, wherein said chemokine is MIP1α.

* * * * *